(12) United States Patent
Thiele et al.

(10) Patent No.: US 10,005,869 B2
(45) Date of Patent: Jun. 26, 2018

(54) POLYMERISATION INITIATORS

(71) Applicant: Trinseo Europe GmbH, Horgen (CH)

(72) Inventors: Sven K. H. Thiele, Horgen (CH);
Christian Döring, Horgen (CH);
Michael Rössle, Horgen (CH); Daniel Heidenreich, Horgen (CH)

(73) Assignee: TRINSEO EUROPE GMBH, Horgen (CH)

( * ) Notice: Subject to any disclaimer, the term of this patent is extended or adjusted under 35 U.S.C. 154(b) by 0 days. days.

(21) Appl. No.: 14/904,972

(22) PCT Filed: Jul. 22, 2013

(86) PCT No.: PCT/EP2013/065399
§ 371 (c)(1),
(2) Date: Jan. 14, 2016

(87) PCT Pub. No.: WO2015/010710
PCT Pub. Date: Jan. 29, 2015

(65) Prior Publication Data
US 2016/0159956 A1 Jun. 9, 2016

(51) Int. Cl.
| | | |
|---|---|---|
| C08F 236/10 | (2006.01) |
| C08F 4/46 | (2006.01) |
| C08F 4/48 | (2006.01) |
| C08F 36/08 | (2006.01) |
| C08F 212/08 | (2006.01) |
| C07F 1/02 | (2006.01) |
| C07F 7/10 | (2006.01) |
| C08C 19/22 | (2006.01) |
| C08C 19/25 | (2006.01) |
| C08C 19/44 | (2006.01) |
| C08L 21/00 | (2006.01) |
| C08L 47/00 | (2006.01) |
| C08F 36/06 | (2006.01) |

(52) U.S. Cl.
CPC .............. *C08F 236/10* (2013.01); *C07F 1/02* (2013.01); *C07F 7/10* (2013.01); *C08C 19/22* (2013.01); *C08C 19/25* (2013.01); *C08C 19/44* (2013.01); *C08F 4/468* (2013.01); *C08F 4/488* (2013.01); *C08F 36/06* (2013.01); *C08F 36/08* (2013.01); *C08L 21/00* (2013.01); *C08L 47/00* (2013.01); *C08F 212/08* (2013.01); *C08L 2205/025* (2013.01)

(58) Field of Classification Search
CPC ........ C08F 236/10; C08F 4/468; C08F 4/488; C08F 36/08; C08F 212/08; C07F 1/02; C07F 7/10; C08C 19/22; C08C 19/25; C08C 19/44; C08L 21/00; C08L 47/00
USPC ...................................................... 524/188
See application file for complete search history.

(56) References Cited

U.S. PATENT DOCUMENTS

| | | |
|---|---|---|
| 3,078,254 A | 2/1963 | Westmeyer |
| 3,244,664 A | 4/1966 | Zelinski |
| 3,281,383 A | 10/1966 | Zelinski |
| 3,629,213 A | 12/1971 | Onishi |
| 3,692,874 A | 9/1972 | Farrar |
| 3,951,936 A | 4/1976 | Hanlon |
| 3,978,103 A | 8/1976 | Meyer-Simon |
| 4,048,206 A | 9/1977 | Voronkov |
| 4,172,190 A | 10/1979 | Tung et al. |
| 4,182,818 A | 1/1980 | Tung et al. |
| 4,200,718 A | 4/1980 | Tung et al. |
| 4,365,103 A | 12/1982 | Chang et al. |
| 4,474,908 A | 10/1984 | Wagner |
| 4,616,069 A | 10/1986 | Watanabe |
| 4,689,368 A | 8/1987 | Jenkins |
| 4,713,458 A | 12/1987 | Frazier et al. |
| 4,931,376 A | 6/1990 | Ikematsu |
| 4,982,029 A | 1/1991 | Chang |
| 5,017,636 A | 5/1991 | Hattori et al. |
| 5,047,484 A | 9/1991 | Tung |

(Continued)

FOREIGN PATENT DOCUMENTS

| | | |
|---|---|---|
| AU | B-81618/94 | 6/1995 |
| CN | 1145367 A | 3/1997 |

(Continued)

OTHER PUBLICATIONS

Hadjichristidis et al., "Macromolecular architectures by living and controlled/living polymerizations", Progress in Polymer Science, Nov. 29, 2006, Pergamon Press, Oxford, GB, vol. 31, No. 12, pp. 1068-1132, http://dx.doi.org/10.1016/j.progpolymsci.2006.07.002, NPL Reference No. XP005783269, ISSN: 0079-6700, DOI: 10.1016/J.Progpolymsci.2006.07.002.
PCT/EP2013/065399 International Search Report dated Sep. 19, 2013 (1 page).
PCT/EP2013/065399 Written Opinion dated Sep. 19, 2013 (5 pages).
Bae, Young Cheol et al., "Coupling Reaction of Living Polyisobutylene using Bis(diphenylethenyl) Compounds as Coupling Agents", ACS Symposium Series, 1997, Chapter 16, pp. 198-212.

(Continued)

*Primary Examiner* — Ling Siu Choi
*Assistant Examiner* — Ronald Grinsted
(74) *Attorney, Agent, or Firm* — Eric D. Babych; Brinks Gilson & Lione

(57) ABSTRACT

The invention relates to polymers obtainable by using novel polymerization initiator compounds and optionally chain end modifying agents. The invention further relates to a method of making the initiator compounds and the corresponding polymers, including chain end-modified polymers. The invention, also relates to polymer compositions comprising the polymer of the invention, and further components such, as extender oils, fillers, etc., and to corresponding vulcanized polymer compositions and articles comprising vulcanized parts made from, the vulcanized polymer composition.

21 Claims, No Drawings

(56) References Cited

U.S. PATENT DOCUMENTS

| | | | |
|---|---|---|---|
| 5,071,920 | A | 12/1991 | Tung |
| 5,086,136 | A | 2/1992 | Takashima |
| 5,089,574 | A | 2/1992 | Castner |
| 5,112,910 | A | 5/1992 | Piejkjo et al. |
| 5,134,199 | A | 7/1992 | Hattori |
| 5,448,002 | A | 9/1995 | Castner |
| 5,462,994 | A | 10/1995 | Lo et al. |
| 5,561,210 | A | 10/1996 | Roy |
| 5,736,612 | A | 4/1998 | Van Dongen et al. |
| 5,750,055 | A | 5/1998 | Van Der Steen et al. |
| 5,753,579 | A | 5/1998 | Jalics |
| 5,753,761 | A | 5/1998 | Sandstrom |
| 5,834,573 | A | 11/1998 | Castner |
| 6,018,007 | A | 1/2000 | Lynch |
| 6,103,842 | A | 8/2000 | Halasa |
| 6,184,168 | B1 | 2/2001 | Lynch |
| 6,229,036 | B1 | 5/2001 | Batz-Sohn |
| 6,310,152 | B1 | 10/2001 | Castner |
| 6,489,415 | B2 | 12/2002 | Liang |
| 6,562,923 | B1 | 5/2003 | Robert et al. |
| 6,617,406 | B2 | 9/2003 | Castner |
| 6,627,715 | B2 | 9/2003 | Halasa |
| 6,693,160 | B1 | 2/2004 | Halasa |
| 6,777,569 | B1 | 8/2004 | Westmeyer |
| 6,984,687 | B2 * | 1/2006 | Henning ............... C08K 5/01 |
| | | | 524/474 |
| 8,236,882 | B2 | 8/2012 | Klockman |
| 8,865,829 | B2 | 10/2014 | Nebhani |
| 2002/0086961 | A1 | 7/2002 | Hsu et al. |
| 2003/0065114 | A1 | 4/2003 | Castner |
| 2003/0153698 | A1 | 8/2003 | Halasa |
| 2005/0124740 | A1 | 6/2005 | Klockman |
| 2005/0159513 | A1 | 7/2005 | Henning |
| 2013/0090423 | A1 | 4/2013 | Qin et al. |
| 2013/0131263 | A1 | 5/2013 | Nebhani |

FOREIGN PATENT DOCUMENTS

| | | |
|---|---|---|
| DE | 29 38 658 A1 | 4/1981 |
| DE | 37 11920 A1 | 10/1988 |
| EP | 0 283 359 A1 | 9/1988 |
| EP | 0 316 857 A2 | 5/1989 |
| EP | 0 413 294 A2 | 2/1991 |
| EP | 0 472 749 A1 | 3/1992 |
| EP | 0 659 787 A1 | 12/1995 |
| EP | 0 690 075 A1 | 1/1996 |
| EP | 0 924 214 | 6/1999 |
| EP | 0 964 008 | 12/1999 |
| EP | 1 367 069 | 12/2003 |
| EP | 1 367 069 A1 | 12/2003 |
| EP | 2 518 104 A1 | 10/2012 |
| JP | S5219192 A | 2/1977 |
| JP | S 54-063186 A | 5/1979 |
| JP | H01-135847 A | 5/1989 |
| JP | H 11147910 A | 6/1999 |
| JP | H 11301794 | 11/1999 |
| JP | 2012-097145 A | 5/2012 |
| JP | 2012-177085 A | 9/2012 |
| RU | 2260600 C1 | 9/2005 |
| WO | WO 2007/047943 | 4/2007 |
| WO | WO 2009/057412 A1 | 5/2009 |
| WO | WO 2009/148932 | 12/2009 |
| WO | WO 2011/002830 A2 | 1/2011 |
| WO | WO 2011/008501 A2 | 1/2011 |
| WO | WO 2011/047220 A1 | 4/2011 |
| WO | WO 2002/20623 A1 | 3/2012 |
| WO | WO 2013/057308 A1 | 5/2012 |
| WO | WO 2012/111697 A1 | 8/2012 |
| WO | WO 2013/046850 A1 | 4/2013 |

OTHER PUBLICATIONS

Bae, Young Cheol et al., "Addition Reaction of Living Polyisobutylene to "Double" Diphenylethylenes, Synthesis of 1,1-Diphenylethylene-Functionalized Polyisobutylene Macromonomers", Macromolecules, 1998, vol. 31, pp. 9379-9383.

Bae, Y. C. et al., "Carbocationic Coupling Reactions of Living Polyisobutylene Using Coupling Agents", Polymer Preprints, 1996, vol. 37, pp. 369-370.

Bandermann, Friedhelm et al., "Bifunctional anionic initiators: A critical study and overview", Makromol. Chem., 1985, vol. 186), pp. 2017-2024.

Bastelberger, Thomas et al. "Electron Transfer and Carbanionic Addition Reactions with Divinylidene Compounds", Makromol. Chem, Symp, 28$^{th}$ 1982, pp. 199.

Bastelberger, Thomas et al. "New divinylidene compounds and their reaction with electron transfer reagents", Makromol. Chem, 1984, vol. 185, pp. 1565-1582.

Broske, A. D. et al., "Investigation of Difunctional Organolthium Initiators", Polymer Preprints, 1984, 25 (2), pp. 85-87.

Broske, A. D. et al., "Investigations of Hydrocarbon Soluble Difunctional Organolithium Initiators Based zupon 1.3-Bis(Phenyl Ethrnyle) Benzene", Recent Adv. Anionic Polym., Proc. Int. Symp.. 1987, pp. 363-380.

Broske, A. D. et al., "Synthesis of Block Copolymers via Difunctional Initiation", Polymer Preprints, 1985, vol. 26 (1), pp. 241-243.

Cambrea, Lee R. et al., "A New Room-Temperature Liquid, High Performance Tricyanate Ester", Journal of Polymer Science: Part A: Polymer Chemistry, 2010, vol. 48, pp. 4547-4554.

Elmaieh, D et al., "Reactions of 1,1-Diarylethyienes with Selenium Compounds", J. Chem. Soc., 1971, vol. 15, pp. 2637-2640.

He, Junpo, "Synthesis of Star, Dendritic and Globular (CO) Polymers by Aionic Polymerization", Polymer Preprints, 2010, vol. 51(1), pp. 188-190.

Higashihara, Tomoya et al. "Successive Synthesis of Well-defined Star-Branched Polymers by a New Iterative Approach Involving Coupling and Transformation Reactions", Macromolecules, 2005, vol. 38 (11), pp. 4577-4587.

Hoecker, Hartwig et al., "Polycombination Reactions Propagated by Electron Transfer: A new Type of Polymerization Reaction", J Polym. Sci. Symposium No. 54, 1976, pp. 361-371.

Hong, K. L. et al., "Synthesis of Model Graft Copolymers With Regularly Spaced Trifunctional or Tetrafunctional Branch Points", Polymer Preprints, 1999, vol. 40 (2), pp. 104-105.

Ikker, Andreas et al. "Coupling of polystyryllithium with divinyl compounds", New Polymeric Mater., 1993, vol. 4 (1), pp. 35-51.

Lattermann, et al. "Darstellung and Charakterisierung von einigen neuen Bis(1-phenylvinyl)-Verbindungen", Die Makromolekulare Chemie, 1974, vol. 175, pp. 2865-2874.

Lee, Jae S. et al., "Synthesis and Characterization of Well-defined, Regularly Branched Polystyrenes Utilizing Multifunctional Initiators", Macromolecules, 2005, vol. 38, pp. 5381-5392.

Leitz, Edgar et al. "Kinetics of the Addition Reaction of sec-Butyllithium onto Bis(1-phenylyinyl)benzenes", Makromol. Chem., 1983, vol. 184, pp. 1893-1899.

Lepoittevin, Benedicte et al. "Synthesis and Characterization of Ring-Shaped Polystyrenes", Macromolecules, 2000, vol. 33, pp. 8218-8224.

Lepoittevin, Benedicte et al., "Synthesis of High-molecular-weight Cyclic and Multicyclic Polystyrenes", Polym. Adv. Technol., 2002, vol. 13, pp. 771-776.

Liu, Ming et al., "Synthesis of Amphiphilic Miktoarm Star Copolymer A$_2$B$_2$ of Polystyrene and Poly(Ethylene Oxide)", Polymer Preprints, 2004, vol. 45(2), pp. 555-556.

Lo, G. Y. et al. "Diene Triblock Polymers with Styrene-Alpha-Methylstyrene Copolymers as End Blocks", Polymer Preprints, 1985, vol. 26(2), pp. 16-17.

Lo, G. Y. et al. "Studies on Dilithium Initiators. 4. Effect of Structure Variations". Macromolecules, 1994, vol. 27, pp. 2241-2248.

Ma, Jingjing, "Synthesis of Well-Defined Macrocyclic Block Copolymers Using Living Coupling Agent Method", Macromol. Symp., 1995, vol. 91, pp. 41-49.

Pispas, Stergios et al. "Micellization of Model Graft Copolymers of the H and π Type in Dilute Solution", Macromolecules, 1996, vol. 29), pp. 7378-7385.

(56) References Cited

OTHER PUBLICATIONS

Quirk, Roderic P. et al., "Anionic Synthesis of Block and Star-Branched Polymers via 1,1-Diphenylethylene-Functionalized Macromonomers", Polymer Preprints, 1996, vol. 37, pp. 402-403.
Quirk, Roderic P. et al. "Anionic Synthesis of Functionalized Cyclic Macro-Molecules Using a Living Coupling Agent", Polymer Preprints, 1988, vol. 29, pp. 10-11.
Quirk, Roderic P. et al., "Anionic Synthesis of Functionalized Cyclic Polybutadinenes With High 1,4-Minrostructure", From Polymer Preprints. American Chemical Society, Division of Polymer Chemistry, 1992, vol. 33 pp. 976-977.
Quirk, Roderic P. et al. "Anionic Synthesis of Functionalized Heteroarm Star Polymers", Polymer Preprints, 1989, vol. 30, pp. 113-114.
Quirk, Roderic P. et al., "Anionic Synthesis of Hetero Three-Armed Star Polymers via 1,1-Diphenylethylene-Functionalized Macromonomers", Polymer Preprints, 1993, vol. 34, pp. 578-579.
Quirk, Roderic P. et al., "Anionic Synthesis of Polystyrene and Polybutadiene Heteroarm Star Polymers", Makromol. Chem., Macromol. Symp. 1992, vol. 53, pp. 201-210.
Quirk, Roderic P. et al., "Dilithium Initiators Based on 1.3-bis(1-Phenylethenylbenzene. Tetrahydrofuran and Lithium sec-Butoxide Effects", Polymer International, 1991, vol. 24, pp. 197-206.
Quirk, Roderic P. et al., "Living Coupling Agents. Rational Synthesis of Heteroarm Star0Brached Polymers", Recent Adv. Anionic Polym., Proc. Int. Symp., (1987), pp. 393-401.
Quirk, Roderic P. et al., "Rational Synthesis of Star Block Copolymers With Compositionally Heterogeneous Arms", Polymer Preprints 1986, vol. 27(1), pp. 188-189.
Schulz, Guenther et al., "1,3-Bis(1-lithio-3-methyl-1-phenylpenty)benzene, an Organodilithium Compound Soluble in Aromatic Hydrocarbons", Angew. Chem. Int. Ed. Engl, 1980, vol. 19 (3), pp. 219-220.
Schulz, Guenther et al., "1,3-Bis(1-phenylvinyl)benzene and Its Reactions with Electron Transfer Reagents". Makromol. Chem., 1977, vol. 178, pp. 2589-2594.
Sun, Wei et al., "Synthesis of Dendritic Polystyrenes from an Anionic Inimer", Macromolecules, 2009, vol. 42, pp. 7309-7317.
Tanaka et al., "Determination of sequence length distribution in SBR by ozonolysis-g.p.c. method", Polymer, 1981, vol. 22, pp. 1721-1723.
Tohyama Mieko et al., "Synthesis of end-functionalized polymer by means of living anionic polymerization," Macromol. Chem. Phys. vol. 197, (1996), pp. 3135-3148.
Tung, L. H. et al., "Studies on Dilithium Initiators. 1. Hydrocarbon-Soluble Initiators", Macromolecules, 1994, vol. 27, pp. 2219-2224.
Wang, Xiaojun et al., "Synthesis of ABCD-Type Miktoarm Star Copolymers and Transformation into Zwitterionic Star Copolymers", Journal of Polymer Science, Part A: Polymer Chemistry, 2007, vol. 45, pp. 4818-4828.
Wang, Xiaojun et al., "Synthesis and Characterization of ABC-type Star and Linear Block Copolymers pf Styrene, Isoprene, and 1,3-Cuclohexadiene", Macromolecules, 2006, vol. 39, pp. 6898-6904.
Xie, Chao et al., "Dendritic Black and Dendritic Brush Copolymers through Anionic Macroinimer Approach", Macromolecules, 2013, vol. 46, pp. 1437-1446.
Yonezawa, Noriyuki et al., "Acid-Medicated Specific α, α-Diarylation and α-Monoarylation Reactions of Pyruvic Acid With/Without Decarbonylation", Synthetic Communications, 1999, vol. 29, No. 10, pp. 1687-1695.
Yu, Fengping et al. "Syhthesis of Graft Copolymers with "V-Shaped" and "Y-Shaped" Side Cjains via Contolled radical and Anionic Polymerizations", Journal of Polymer Science, Part A: Polymer Chemistry, (2007), vol. 45, pp. 4013-4025.
Zhang, Hefeng et al., "Continuous Process for the Synthesis of Dendrimer-Like Star Polymers by Anionic Polymerization", Macromolecules, 2012, vol. 45, pp. 828-841.
Zhang, Xuetao, et al., "Synthesis and characterization of symmetrical triblock copolymers containing crystallizable high-trans-1,4-polybutadiene", Polym. Bull., 2010, vol. 65, pp. 201-213.

* cited by examiner

US 10,005,869 B2

POLYMERISATION INITIATORS

This application claims priority to International Application No. PCT/EP2013/065399 filed Jul. 22, 2013, the entire contents of which are incorporated herein by reference.

FIELD OF THE INVENTION

This invention relates to polymerization initiators and their preparation. The invention also relates to polymers, including modified (i.e. chain-end modified) polymers, prepared with the initiators of the invention and to polymer compositions made therefrom. The invention furthermore relates to the use of these compositions in the preparation of vulcanized compositions and articles prepared from the same. The polymer compositions are useful in the preparation of vulcanized and, thus, cross-linked elastomeric compositions having relatively low hysteresis loss, good grip properties and high abrasion resistance. Such compositions are useful in many articles, including tire treads having low heat build-up, low rolling resistance and high abrasion resistance, in combination with a good balance of other desirable physical and chemical properties, for example, good wet grip, ice grip and tensile strength and excellent processability.

BACKGROUND OF THE INVENTION

Increasing oil prices and national legislation requiring the reduction of automotive carbon dioxide emissions force tire and rubber producers to produce "fuel-efficient" and thus fuel-saving tires. One general approach to obtain fuel-efficient tires is to produce tire formulations which have reduced hysteresis loss. A major source of hysteresis in vulcanized elastomeric polymers is attributed to free polymer chain ends, i.e. the section of the elastomeric polymer chain between the last cross-link and the end of the polymer chain. This free end of the polymer does not participate in the efficient elastically recoverable process and, as a result, energy transmitted to this section of the polymer is lost. The dissipated energy leads to a pronounced hysteresis under dynamic deformation. Another source of hysteresis in vulcanized elastomeric polymers is attributed to an insufficient distribution of filler particles in the vulcanized elastomeric polymer composition. The hysteresis loss of a cross-linked elastomeric polymer composition is related to its tan δ value at 60° C. (see ISO 4664-1:2005; Rubber. Vulcanized or thermoplastic; Determination of dynamic properties—part 1: General guidance). In general, vulcanized elastomeric polymer compositions having relatively small tan δ values at 60° C. are preferred as having lower hysteresis loss. In the final tire product, this translates into a lower rolling resistance and better fuel economy.

It is generally accepted that a lower rolling resistance tire can be made at the expense of deteriorated wet grip properties. For example, if, in a random solution styrene-butadiene rubber (random SSBR), the polystyrene unit concentration is reduced with respect to the total polybutadiene unit concentration, and the 1,2-polybutadiene unit concentration is kept constant, the SSBR glass transition temperature is reduced and, as a result, both tan δ at 60° C. and tan δ at 0° C. are reduced, generally corresponding to improved rolling resistance and deteriorated wet grip performance of the tire. Similarly, if, in a random SSBR, the 1,2-polybutadiene unit concentration is reduced with respect to the total polybutadiene unit concentration, and the polystyrene unit concentration is kept constant, the SSBR glass transition temperature is reduced and, as a result, both tan δ at 60° C. and tan δ at 0° C. are reduced, generally corresponding to improved rolling resistance and deteriorated wet grip performance of the tire. Accordingly, when assessing the rubber vulcanizate performance correctly, both the rolling resistance, related to tan δ at 60° C., and the wet grip, related to tan δ at 0° C., should be monitored along with the tire heat build-up.

One generally accepted approach for reducing hysteresis loss is to reduce the number of free chain ends of elastomeric polymers. Various techniques have been described in the literature, including the use of "coupling agents" such as tin tetrachloride, which may functionalize the polymer chain end and react with components of an elastomeric composition, for example with a filler or with unsaturated portions of a polymer. Examples of such techniques and coupling agents are described in the following patents: U.S. Pat. Nos. 3,281,383; 3,244,664 and 3,692,874 (for example, tetrachlorosilane); U.S. Pat. Nos. 3,978,103; 4,048,206; 4,474,908; 6,777,569 (blocked mercaptosilanes) and U.S. Pat. No. 3,078,254 (a multi-halogen-substituted hydrocarbon, such as 1,3,5-tri(bromomethyl)benzene); U.S. Pat. No. 4,616,069 (tin compounds and organic amino or amine compounds); and U.S. 2005/0124740.

The reference article "Synthesis of end-functionalized polymer by means of living anionic polymerization", Journal of Macromolecular Chemistry and Physics, 197, (1996), 3135-3148, describes the synthesis of "polystyrene-containing" and "polyisoprene-containing" living polymers with hydroxy (—OH) and mercapto (—SH) functional end caps, obtained by reaction of living polymers with haloalkanes containing silyl ether and silyl thioether functions. The tertiary-butyldimethylsilyl (TBDMS) group is preferred as a protecting group for the —OH and —SH functional groups in the termination reactions, because the corresponding silyl ethers and thioethers are found to be both stable and compatible with anionic living polymers.

WO 2007/047943 describes the use of a silane sulfide omega chain end modifier represented by the formula $(RO)_x(R)_ySi—R'—S—SiR_3$, wherein x is 1, 2 or 3, y is 0, 1 or 2, $x+y=3$, R is alkyl, and R' is aryl, alkylaryl or alkyl, to produce a chain end-modified elastomeric polymer, which is used as a component in a vulcanized elastomeric polymer composition or a tire tread.

More specifically, according to WO 2007/047943, a silane sulfide compound is reacted with anionically-initiated living polymers to produce "chain end-modified" polymers, which are subsequently blended with fillers, vulcanizing agents, accelerators or oil extenders to produce a vulcanized elastomeric polymer composition having low hysteresis loss.

The vulcanized elastomeric polymer compositions are described as exhibiting lower tan δ values at 60° C., particularly in comparison with compounds based on corresponding non-modified polymers, without negatively affecting tan δ values at 0° C. and processing characteristics. Individual exemplary cured polymer formulations comprising modified polymers are shown to result in reduced tan δ at 60° C. and heat build-up values but equivalent tan δ values at 0° C. They are described as being useful in preparing tire treads having lower rolling resistance, while maintaining good wet grip properties. In case the modifier contains two or three alkoxy groups (x=2 or 3), the resulting functionalized polymer comprises —Si—OR groups and —S—SiR$_3$ groups, which are converted under suitable conditions, such as typically present during reactive mixing of functionalized polymers with fillers, into silanol groups (—Si—OH) and thiol groups (—S—H). Silanol groups and thiol groups are reactive with respect to fillers containing silanol surface groups, such as silica. Thus, the formation of bonds between functionalized polymer and silica is expected. Although cured rubber hysteresis properties can be improved significantly through application of the technology described in WO 2007/047943, the impact of the technology is limited due to the fact that only one polymer chain end can be functionalized by using the modifier compound described.

Accordingly, there is a need for an efficient modification of the second polymer chain end.

There is a need for modification methods and resulting polymers, including modified polymers, which can be used for further optimizing dynamic properties of vulcanizates containing silica and carbon black, including low hysteresis loss and high abrasion resistance, corresponding to a high wet grip, low rolling resistance and high abrasion resistance in tires. In addition, there is a need to further decrease the vulcanizate heat build-up during thermal exposure and under mechanical stress. These needs have been met by the following invention.

SUMMARY OF THE INVENTION

In a first aspect, the invention provides a polymerization initiator according to Formula 1

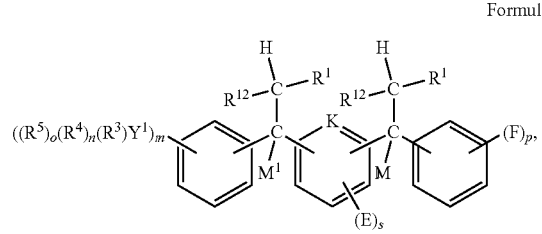

Formula 1 or Lewis base adducts thereof,
wherein
each $M^1$ is independently selected from lithium, sodium and potassium;
each $R^1$ is independently selected from $(C_1-C_{100})$ alkyl and $(C_2-C_{100})$ alkenyl, optionally substituted with one or more $(C_6-C_{12})$ aryl groups and optionally linked to the carbon atom C by up to 25 monomer units selected from conjugated diene monomers and aromatic vinyl compounds, especially butadiene, isoprene and styrene;
each $R^{12}$ is independently selected from hydrogen, $(C_1-C_{10})$ alkyl, $(C_6-C_{12})$ aryl and $(C_7-C_{18})$ alkylaryl;
each $Y^1$ is independently selected from a nitrogen atom, a sulfur atom and a silicon atom;
$R^3$, $R^4$ and $R^5$ are each independently selected from $(C_1-C_{18})$ alkyl, di$(C_1-C_6)$ alkyl amine (only when $Y^1$ is a silicon atom), $(C_6-C_{18})$ aryl, $(C_7-C_{18})$ alkylaryl and, when $Y^1$ is not a silicon atom, —$SiR^{14}R^{15}R^{16}$, wherein $R^{14}$, $R^{15}$ and $R^{16}$ are each independently selected from $(C_1-C_{18})$ alkyl, $(C_6-C_{18})$ aryl and $(C_7-C_{18})$ alkylaryl; n and o are each an integer selected from 0 and 1; and n+o=1 when $Y^1$=N, n=o=0 when $Y^1$=S, and n+o=2 when $Y^1$=Si;
m is an integer selected from 1, 2 and 3;
each E is independently selected from $(C_1-C_{18})$ alkyl, $(C_6-C_{18})$ aryl, $(C_7-C_{18})$ alkylaryl and —$Y^3(R^9)(R^{10})_t(R^{11})_u$, wherein
$Y^3$ is selected from a nitrogen atom, a sulfur atom and a silicon atom; $R^9$, $R^{10}$ and $R^{11}$ are each independently selected from $(C_1-C_{18})$ alkyl, di$(C_1-C_6)$ alkyl amine (only when $Y^3$ is a silicon atom), $(C_6-C_{18})$ aryl, $(C_7-C_{18})$ alkylaryl, and, when $Y^3$ is not a silicon atom, —$SiR^{20}R^{21}R^{22}$, wherein $R^{20}$, $R^{21}$ and $R^{22}$ are each independently selected from $(C_1-C_{18})$ alkyl, $(C_6-C_{18})$ aryl and $(C_7-C_{18})$ alkylaryl; t and u are each an integer selected from 0 and 1; and t+u=1 when $Y^3$=N, t=u=0 when $Y^3$=S, and t+u=2 when $Y^3$=Si;
s is an integer selected from 0, 1 and 2;
each F is independently selected from $(C_1-C_{18})$ alkyl, $(C_6-C_{18})$ aryl, $(C_7-C_{18})$ alkylaryl and —$Y^2(R^6)(R^7)_q(R^8)_r$, wherein $Y^2$ is selected from a nitrogen atom, a sulfur atom and a silicon atom; $R^6$, $R^7$ and $R^8$ are each independently selected from $(C_1-C_{18})$ alkyl, di$(C_1-C_6)$ alkyl amine (only when $Y^2$ is a silicon atom), $(C_6-C_{18})$ aryl, $(C_7-C_{18})$ alkylaryl and, when $Y^2$ is not a silicon atom, —$SiR^{17}R^{18}R^{19}$, wherein $R^{17}$, $R^{18}$ and $R^{19}$ are each independently selected from $(C_1-C_{18})$ alkyl, $(C_6-C_{18})$ aryl and $(C_7-C_{18})$ alkylaryl; q and r are each an integer selected from 0 and 1; and q+r=1 when $Y^2$=N, q=r=0 when $Y^2$=S, and q+r=2 when $Y^2$=Si;
p is an integer selected from 0, 1, 2 and 3;
K is selected from nitrogen, >C—H and >C—$Y^3(R^9)(R^{10})_t(R^{11})_u$, wherein $Y^3$, $R^9$, $R^{10}$, $R^{11}$, t and u are independently as defined above.

In a second aspect, the invention provides a method of making the polymerization initiator of Formula 1, including Lewis base adducts thereof, comprising the step of reacting (i) a compound of Formula 2

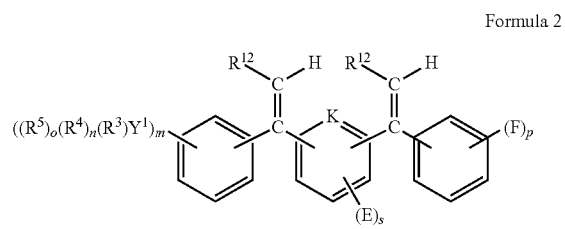

Formula 2 wherein K, E, F, $Y^1$, $R^3$, $R^4$, $R^5$, $R^{12}$, m, n, o, p and s are each as defined in Formula 1, with (ii) at least one compound of Formula 3

$R^1M^1$    Formula 3 wherein $M^1$ and $R^1$ are each as defined in Formula 1, and optionally (iii) a Lewis base.

In a third aspect, the invention provides a polymer of the invention, including a modified polymer, which is the reaction product of
i) a polymerization initiator of Formula 1 or a Lewis base adduct thereof and
ii) at least one type of polymerizable monomers selected from conjugated olefins and aromatic vinyl compounds.

In a fourth aspect, the invention provides a method of making the polymer of the invention, including modified polymer, comprising the step of reacting
i) a polymerization initiator of Formula 1 or a Lewis base adduct thereof and
ii) at least one type of polymerizable monomers selected from conjugated olefins and aromatic vinyl compounds.

In a fifth aspect, the invention provides a first polymer composition comprising the polymer of the invention, including modified polymer, and one or more further components selected from (i) components which are added to or formed as a result of the polymerization process used for making the polymer and (ii) components which remain after solvent removal from the polymerization process. Components which are added to the polymerization process include, in particular, oils (extender oils), stabilizers and further polymers.

In a sixth aspect, the invention provides a second polymer composition comprising the polymer of the invention, including modified polymer, and one or more fillers. The second polymer composition is the result of mechanical mixing of the polymer of the invention, including modified polymer, as obtained after solvent removal from the polymerization process, and one or more fillers and further optional components.

The first and second polymer compositions may optionally further comprise a least one vulcanizing agent.

In a seventh aspect, the invention provides a vulcanized polymer composition which is obtained by vulcanizing the first or the second polymer composition, which comprises at least one vulcanizing agent.

In an eighth aspect, the invention provides a method of making the vulcanized polymer composition of the seventh aspect, comprising the step of vulcanizing the first or second polymer composition, which comprises at least one vulcanizing agent.

In a ninth aspect, the invention provides an article comprising at least one component formed from a vulcanized polymer composition of the invention. The article may be, for example, a tire, a tire tread, a tire side wall, an automotive part, a footwear component, a golf ball, a belt, a gasket, a seal or a hose.

DETAILED DESCRIPTION OF THE INVENTION

Polymerization Initiator (Diinitiator Compound)

The polymerization initiator of the first aspect of the invention is a compound of Formula 1 as defined above. The polymerization initiator of the invention includes at least two carbanions which are each linked to a metal atom $M^1$.

In one preferred embodiment, $M^1$ is lithium;
$R^1$ is identical and is selected from $(C_1-C_{10})$ alkyl;
each $R^{12}$ is independently selected from hydrogen and $(C_1-C_{10})$ alkyl, preferably hydrogen;
$Y^1$ and $Y^2$ are identical;
$R^3$, $R^4$ and $R^5$ are each independently selected from $(C_1-C_{18})$ alkyl and, when $Y^1$ is not a silicon atom, $-SiR^{14}R^{15}R^{16}$, wherein $R^{14}$, $R^{15}$ and $R^{16}$ are each independently selected from $(C_1-C_{18})$ alkyl;
each E is independently selected from $(C_1-C_{18})$ alkyl;
each F is independently selected from $-Y^2(R^6)(R^7)_q(R^8)_r$, wherein $R^6$, $R^7$ and $R^8$ are each independently selected from $(C_1-C_{18})$ alkyl and, when $Y^2$ is not a silicon atom, $-SiR^{17}R^{18}R^{19}$, wherein $R^{17}$, $R^{18}$ and $R^{19}$ are each independently selected from $(C_1-C_{18})$ alkyl;
p is an integer selected from 1, 2 and 3;
K is selected from nitrogen and >C—H; and
all other substituents or groups are as generally defined for Formula 1

In one embodiment, $Y^1$, $Y^2$ and $Y^3$ are each a sulfur atom. In another embodiment, $Y^1$, $Y^2$ and $Y^3$ are each a nitrogen atom. In yet another embodiment, $Y^1$, $Y^2$ and $Y^3$ are each a silicon atom.

In one preferred embodiment, referred to as "Embodiment 1", the polymerization initiator of Formula 1 is represented by the following Formula 5:

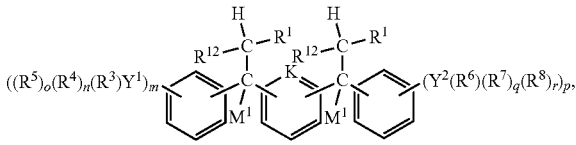

Formula 5 or a Lewis base adduct thereof,
wherein
$M^1$ is lithium;
each $R^1$ is independently selected from $(C_1-C_{18})$ alkyl
p is an integer selected from 1, 2 and 3;
K is selected from nitrogen and >C—H; and
all other substituents or groups are as generally defined for Formula 1 above.

In one embodiment of the polymerization initiator of Formula 5,
each $R^1$ is independently selected from $(C_1-C_7)$ alkyl;
$R^{12}$ is hydrogen;
$R^3$, $R^4$ and $R^5$ are each independently selected from $(C_1-C_{10})$ alkyl and, when $Y^1$ is not a silicon atom, $-SiR^{14}R^{15}R^{16}$, wherein $R^{14}$, $R^{15}$ and $R^{16}$ are each independently selected from $(C_1-C_{16})$ alkyl; and
$R^6$, $R^7$ and $R^8$ are each independently selected from $(C_1-C_{10})$ alkyl and, when $Y^2$ is not a silicon atom, $-SiR^{17}R^{18}R^{19}$, wherein $R^{17}$, $R^{18}$ and $R^{19}$ are each independently selected from $(C_1-C_{16})$ alkyl.

In a preferred embodiment of the polymerization initiator of Formula 5,
each $R^1$ is independently selected from $(C_1-C_{10})$ alkyl;
$R^{12}$ is hydrogen;
$R^3$, $R^4$ and $R^5$ are each independently selected from $(C_1-C_{18})$ alkyl and, when $Y^1$ is not a silicon atom, $-SiR^{14}R^{15}R^{16}$, wherein $R^{14}$, $R^{15}$ and $R^{16}$ are each independently selected from $(C_1-C_{10})$ alkyl;
$R^6$, $R^7$ and $R^8$ are each independently selected from $(C_1-C_{18})$ alkyl and, when $Y^2$ is not a silicon atom, $-SiR^{17}R^{18}R^{19}$, wherein $R^{17}$, $R^{18}$ and $R^{19}$ are each independently selected from $(C_1-C_{10})$ alkyl;
m and p are each independently selected from an integer of 1 and 2; and
all other substituents or groups are as generally defined herein for Embodiment 1.

In another preferred embodiment, referred to as "Embodiment 2", the polymerization initiator of Formula 1 is represented by the following Formula 6:

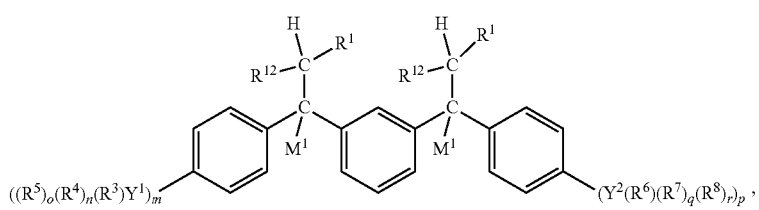

Formula 6 or a Lewis base adduct thereof,
wherein
$M^1$ is lithium;
each $R^1$ is independently selected from $(C_1-C_{10})$ alkyl;
$R^{12}$ is hydrogen:
$R^3$, $R^4$ and $R^5$ are each independently selected from $(C_1-C_{18})$ alkyl and, when $Y^1$ is not a silicon atom, $-SiR^{14}R^{15}R^{16}$, wherein $R^{14}$, $R^{15}$ and $R^{16}$ are each independently selected from $(C_1-C_{10})$ alkyl;

m and p are each independently an integer selected from 1 and 2;

$R^6$, $R^7$ and $R^8$ are each independently selected from $(C_1\text{-}C_{18})$ alkyl and, when $Y^2$ is not a silicon atom, $-SiR^{17}R^{18}R^{19}$, wherein $R^{17}$, $R^{18}$ and $R^{19}$ are each independently selected from $(C_1\text{-}C_{10})$ alkyl; and all other substituents or groups are as generally defined for Formula 1 above.

In one embodiment of the polymerization initiator of Formula 6, each $R^1$ is independently selected from $(C_1\text{-}C_7)$ alkyl;

$R^{12}$ is hydrogen;

$R^3$, $R^4$ and $R^5$ are each independently selected from $(C_1\text{-}C_{10})$ alkyl and, when $Y^1$ is not a silicon atom, $-SiR^{14}R^{15}R^{16}$, wherein $R^{14}$, $R^{15}$ and $R^{16}$ are selected from $(C_1\text{-}C_{16})$ alkyl; and $R^6$, $R^7$ and $R^8$ are each independently selected from $(C_1\text{-}C_{10})$ alkyl and, when $Y^2$ is not a silicon atom, $-SiR^{17}R^{18}R^{19}$, wherein $R^{17}$, $R^{18}$ and $R^{19}$ are each independently selected from $(C_1\text{-}C_{10})$ alkyl.

In more specific embodiments, the polymerization initiator is represented by the following Formula 17, 18 or 19:

$R^6$, $R^7$ and $R^8$ are each independently selected from $(C_1\text{-}C_{18})$ alkyl and, when $Y^2$ is not a silicon atom, $-SiR^{17}R^{18}R^{19}$, wherein $R^{17}$, $R^{18}$ and $R^{19}$ are each independently selected from $(C_1\text{-}C_{10})$ alkyl.

In one embodiment of Formula 17, 18 or 19, each $R^1$ is each independently selected from $(C_1\text{-}C_7)$ alkyl;

$R^{12}$ is hydrogen;

$R^3$, $R^4$ and $R^5$ are each independently selected from $(C_1\text{-}C_{10})$ alkyl and, when $Y^1$ is not a silicon atom, $-SiR^{14}R^{15}R^{16}$;

wherein $R^{14}$, $R^{15}$ and $R^{16}$ are selected from $(C_1\text{-}C_{10})$ alkyl; and $R^6$, $R^7$ and $R^8$ are each independently selected from $(C_1\text{-}C_{18})$ alkyl and, when $Y^2$ is not a silicon atom, $-SiR^{17}R^{18}R^{19}$, wherein $R^{17}$, $R^{18}$ and $R^{19}$ are each independently selected from $(C_1\text{-}C_{10})$ alkyl.

Among the polymerization initiators represented by Formulas 1, 5, 6, 17, 18 and 19, those of Formulas 6, 17, 18 and 19 are preferred, and those of Formula 18 are most preferred.

Lewis Base

Suitable Lewis bases for forming Lewis base adducts with the polymerization initiator of Formula 1 of the invention, including embodiments thereof, such as those of Formulas 5,

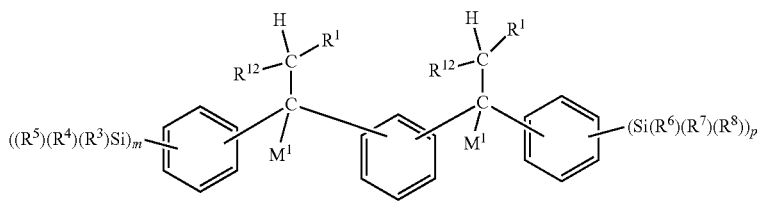

Formula 17

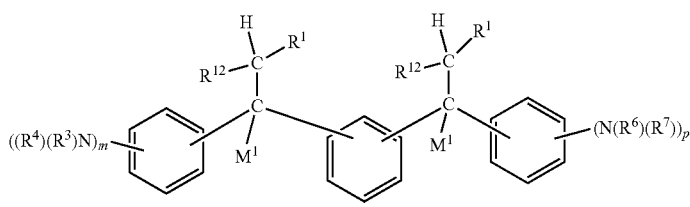

Formula 18

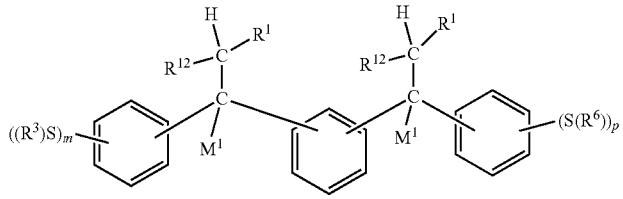

Formula 19 or Lewis base adducts thereof, wherein $M^1$ is lithium;

each $R^1$ is independently selected from $(C_1\text{-}C_{18})$ alkyl; and all other substituents or groups are as generally defined fir Formula 1 above.

In one embodiment of the polymerization initiator represented by Formula 17, 18 or 19, each $R^1$ is independently selected from $(C_1\text{-}C_{10})$ alkyl;

$R^{12}$ is hydrogen;

$R^3$, $R^4$ and $R^5$ are each independently selected from $(C_1\text{-}C_{18})$ alkyl and, when $Y^1$ is not a silicon atom, $-SiR^{14}R^{15}R^{16}$;

wherein $R^{14}$, $R^{15}$ and $R^{16}$ are selected from $(C_1\text{-}C_{10})$ alkyl; and 6 and 17 to 19, include those described in the Section "Randomizer Agents" as well as those according to the following Formulas 20 and 21:

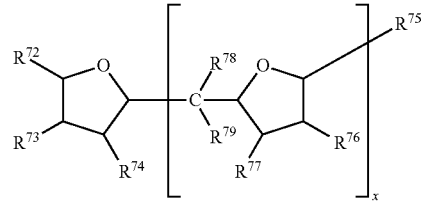

Formula 20

Formula 21

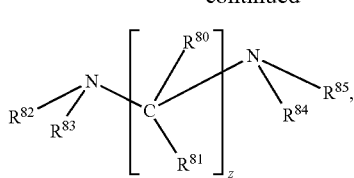

wherein
$R^{72}$, $R^{73}$, $R^{74}$, $R^{75}$, $R^{76}$, $R^{77}$, $R^{78}$, $R^{79}$, $R^{80}$, $R^{81}$, $R^{82}$, $R^{83}$, $R^{84}$ and $R^{85}$ are each independently selected from hydrogen, ($C_1$-$C_{18}$) alkyl, ($C_6$-$C_{18}$) aryl and ($C_7$-$C_{18}$) alkylaryl;
z is an integer selected from 1, 2 and 3; and
x is an integer selected from 1, 2, 3, 4 and 5.

Preferred Lewis bases for use in the polymerization initiator of Formula 1 of the invention are those of Formulas 20 and 21, and particularly preferred are those of Formula 21, wherein z is an integer selected from 1, 2 and 3.

Method of Making the Polymerization Initiator

The polymerization initiators of the invention are produced, as the second aspect of the invention, from the corresponding polymerization initiator precursor compounds of Formula 2, which include at least two olefinic bonds in conjugation with an aromatic ring.

The method of making the polymerization initiator of Formula 1, including Lewis base adducts thereof, comprises the step of reacting an initiator precursor compound of Formula 2 with at least one compound of Formula 3 and optionally a Lewis base. The reaction is usually carried out at a ratio of compound of Formula 3 to compound of Formula 2 in terms of mole equivalents of from 1.1 to 16 (1.1:1 to 16:1), preferably from 1.5 to 4 and even more preferably from 1.8 to 2.2. It is preferably performed in a nonpolar solvent, including hydrocarbon solvent, including aliphatic and aromatic solvent, preferably aliphatic solvent, such as hexane, heptane, pentane, isopar, cyclohexane and methylcyclohexane, and is usually carried out for a period of from 2 seconds to 3 days, preferably from 5 seconds to 2 days, even more preferably from 10 seconds to 10 hours, at a temperature ranging from −60° C. to 130° C., preferably from 0° C. to 100° C. and even more preferably from 20° C. to 70° C.

A polymerization initiator of the invention in which $R^1$ is linked to the carbon atom C by up to 25 monomer units can be obtained by prior reaction of the compound of Formula 3 with monomers selected from conjugated diene monomers and aromatic vinyl compounds, especially butadiene, isoprene and styrene, thus producing a compound of Formula 3 wherein $R^1$ is linked to $M^1$ by an oligomeric chain of up to 25 monomer units. Subsequently, this "oligomer" of Formula 3 is reacted with the initiator precursor compound of Formula 2, as described herein.

The Lewis base may be added to the precursor compound of Formula 2 prior to the addition of and reaction with the compound of Formula 3, so as to be present in the reaction from the beginning. Alternatively, it may be added during the reaction or after completion of the reaction. Any of these alternative additions will result in the formation of a Lewis base adduct of the polymerization initiator of Formula 1. When a Lewis base is present in the reaction for making the polymerization initiator of the invention, it is usually used at a ratio of initiator precursor compound of Formula 2 to Lewis base in terms of mole equivalents of from 0.1 to 20, preferably from 0.4 to 5.0 and even more preferably from 0.5 to 3.0.

For increasing the storage stability (shelf life) of the polymerization initiator, it is possible to contact the resulting reaction mixture containing the polymerization initiator and including alkali metal $M^1$ with a limited amount of one or more polymerizable monomers selected from conjugated diene monomers and aromatic vinyl compounds, preferably selected from styrene, butadiene and isoprene. For this purpose, an amount of up to 1000 equivalents, preferably up to 200 equivalents, most preferably up to 75 equivalents of polymerizable monomer per alkali metal equivalent is suitably used.

Preferred embodiments of the reaction and of the compounds of Formulas 2 and 3 are those which provide a polymerization initiator of Formula 1 and embodiments thereof as defined herein in the description of the polymerization initiator.

In one embodiment, referred to as "Embodiment 3", the polymerization initiator of Formula 5 as defined above is obtained by reacting a compound of the following Formula 7

Formula 7

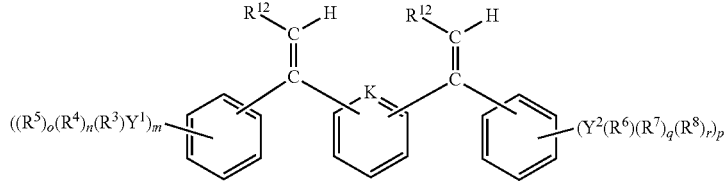

wherein K, $Y^1$, $Y^2$, $R^3$, $R^4$, $R^5$, $R^6$, $R^7$, $R^8$, $R^{12}$, m, n, o, p, q and r are as defined for Formula 5, with at least one compound of Formula 3, wherein $M^1$ and $R^1$ are as defined for Formula 5, and optionally a Lewis base.

Preferred embodiments of the reaction of Embodiment 3 and of the compounds of Formulas 7 and 3 are those which provide a polymerization initiator of Formula 5 (Embodiment 1) and embodiments thereof as defined herein in the description of the polymerization initiator.

In one embodiment, the polymerization initiator of Formula 17 as defined above is obtained by reacting a compound of the following Formula 22

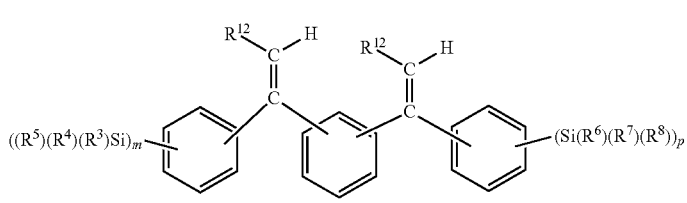

Formula 22 wherein $R^3$, $R^4$, $R^5$, $R^6$, $R^7$, $R^8$, $R^{12}$, m and p are as defined for Formula 17, with at least one compound of Formula 3, wherein $M^1$ and $R^1$ are as defined for Formula 17, and optionally a Lewis base.

In one embodiment, the polymerization initiator of Formula 18 as defined above is obtained by reacting a compound of the following Formula 23:

FIG 23

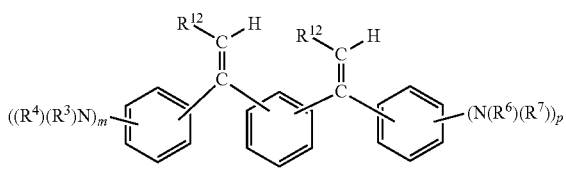

wherein $R^3$, $R^4$, $R^6$, $R^7$, $R^{12}$, m and p are as defined for Formula 18, with at least one compound of Formula 3, wherein $M^1$ and $R^1$ are as defined for Formula 18, and optionally a Lewis base.

In one embodiment, the polymerization initiator of Formula 19 as defined above is obtained by reacting a compound of the following Formula 24

Formula 24

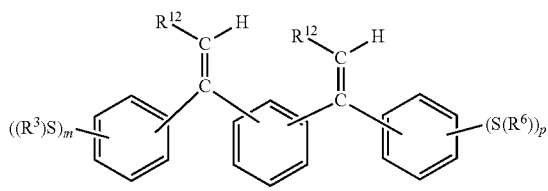

wherein $R^3$, $R^6$, $R^{12}$, m and p are as defined for Formula 19, with at least one compound of Formula 3, wherein $M^1$ and $R^1$ are as defined for Formula 19, and optionally a Lewis base.

Preferred embodiments of the reaction and of the compounds of Formula 22, 23 or 24 and Formula 3 are those which provide a polymerization initiator of Formula 17, 18 or 19, respectively, and embodiments thereof as defined herein in the description of the polymerization initiator.

Useful polymerization initiator precursor compounds include the following:

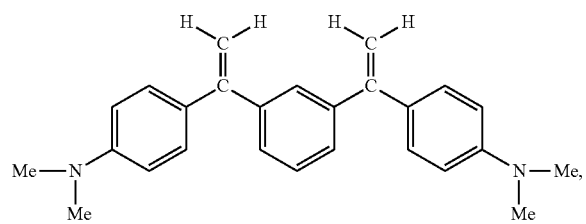

-continued

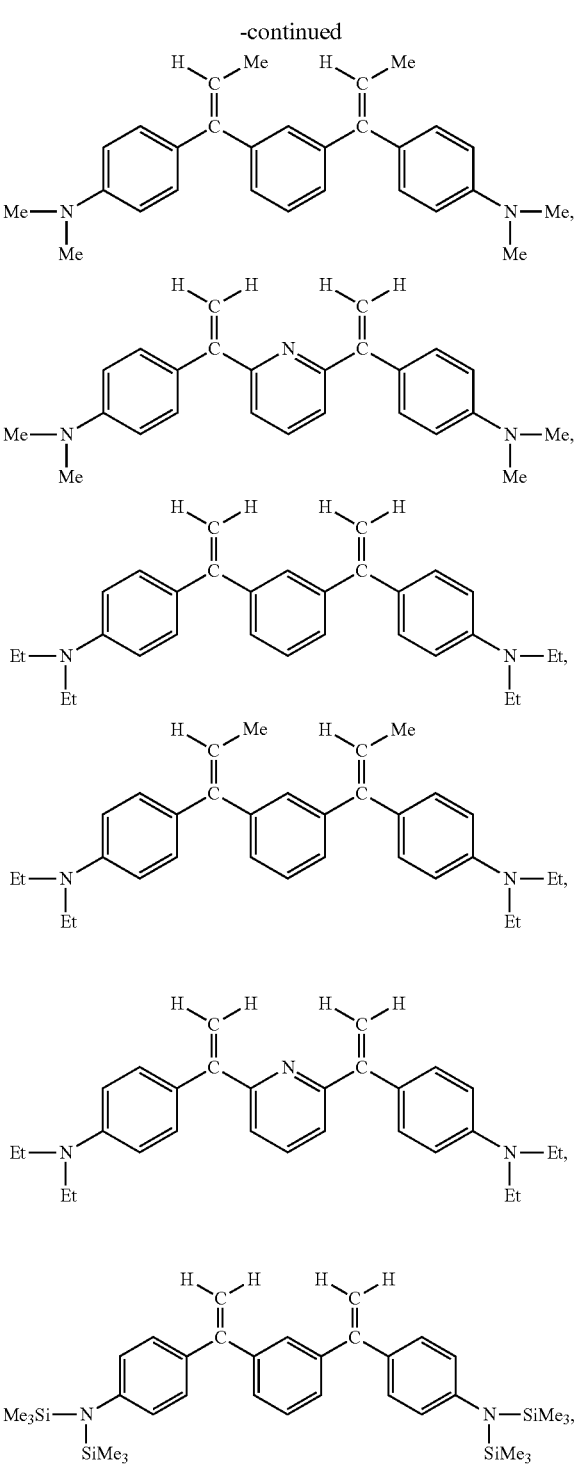

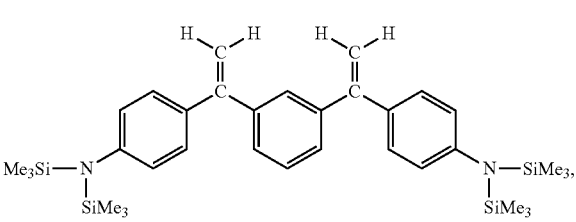

-continued
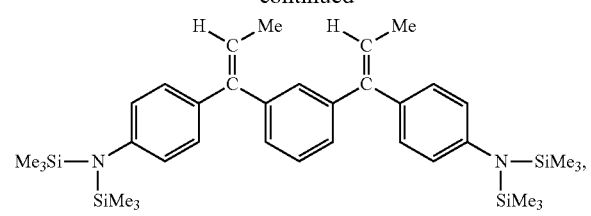
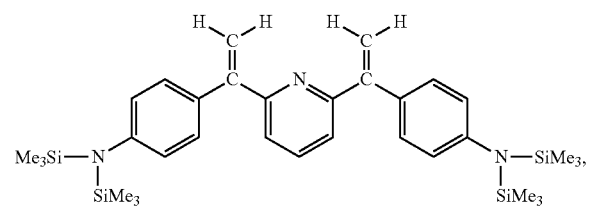
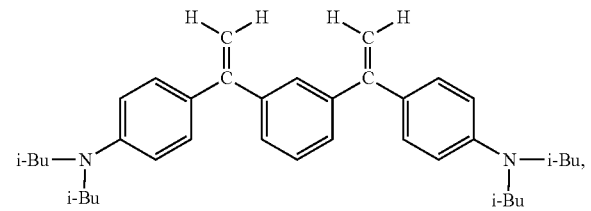
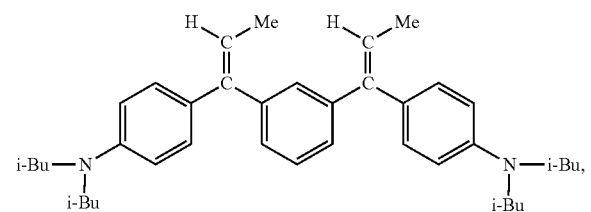
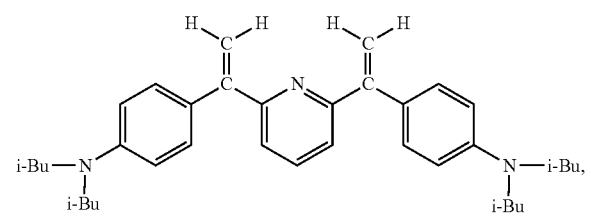
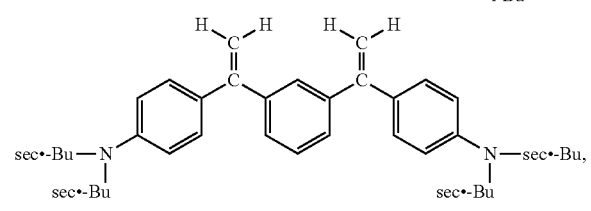
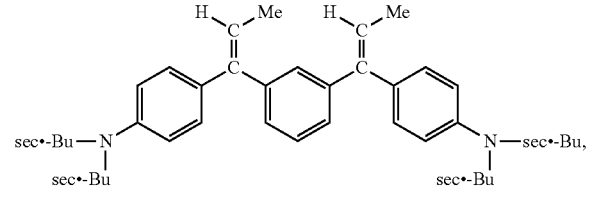
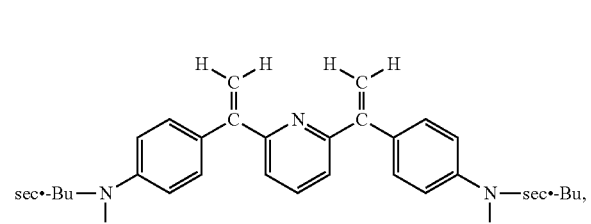
-continued
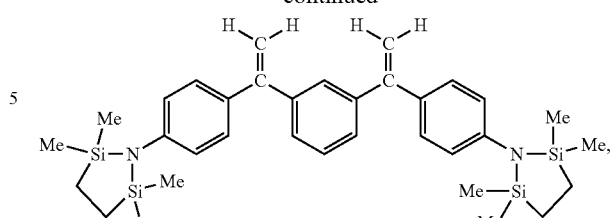
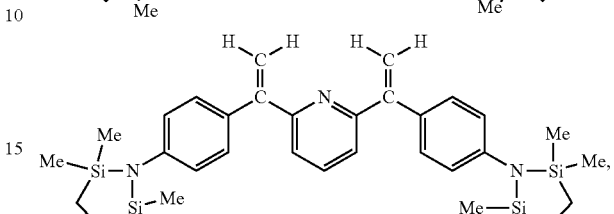
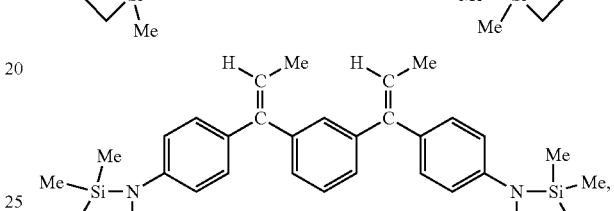
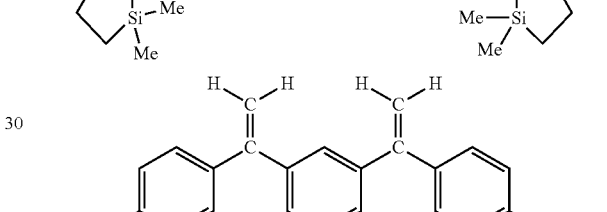
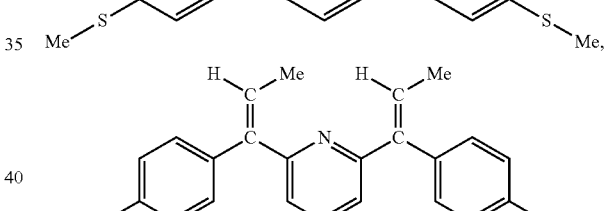
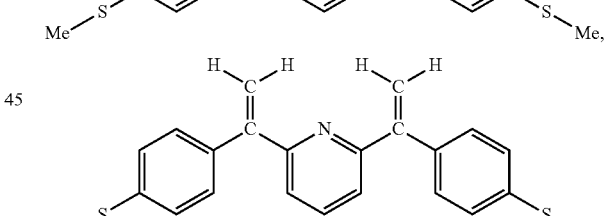
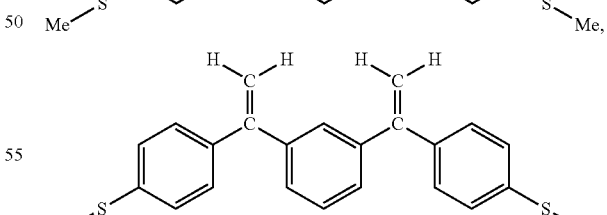
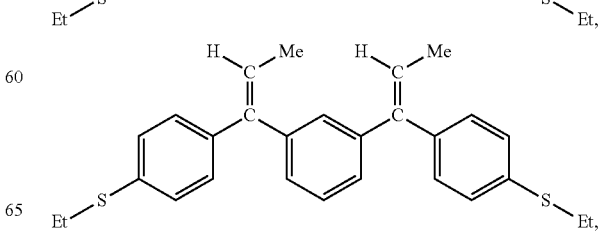

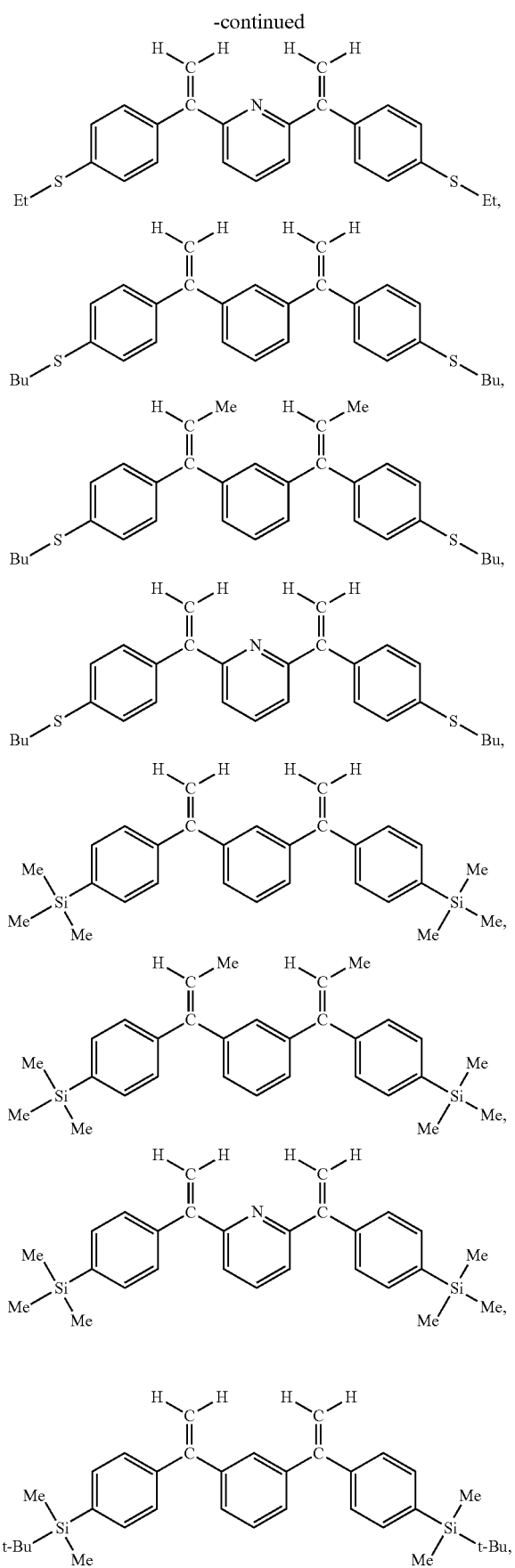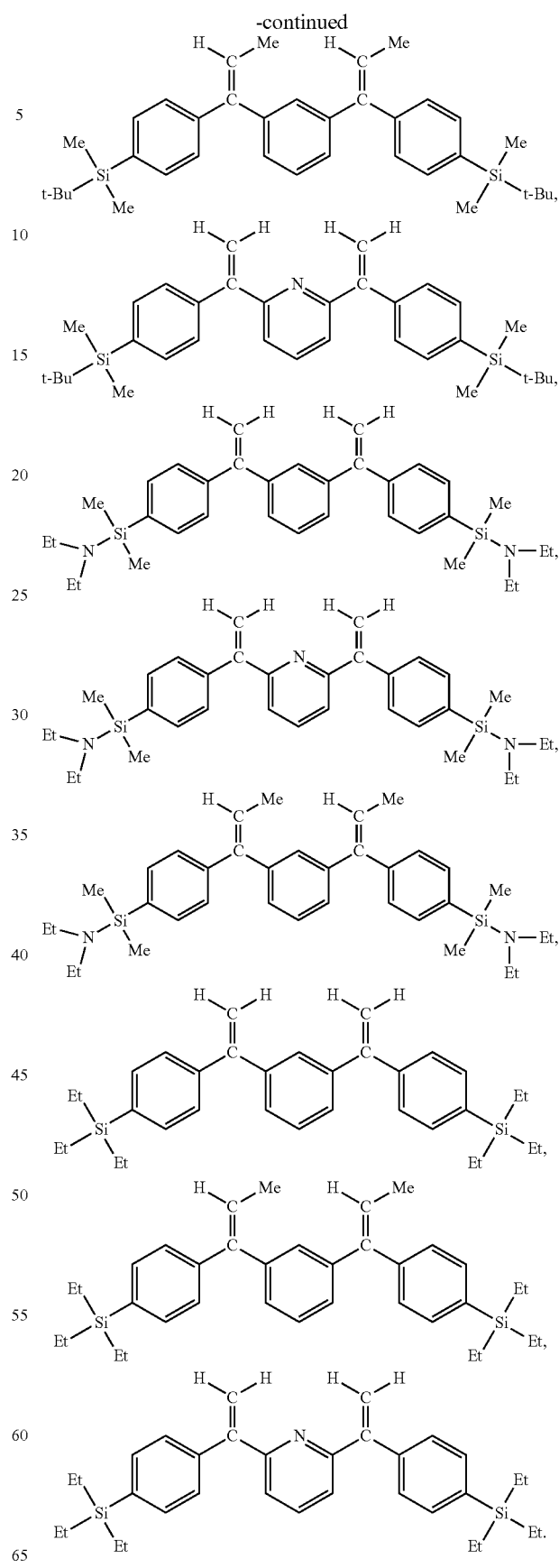

Polymer

The polymer of the third aspect of the invention, including modified polymer, is the reaction product of:
  i) a polymerization initiator of Formula 1 or a Lewis base adduct thereof and
  ii) at least one type of polymerizable monomers selected from conjugated olefins and aromatic vinyl compounds.

Generally, for producing a polymer of the invention, one or more polymerization initiators of the invention may be used.

In specific embodiments of the polymer of the invention, the polymerization initiator used for its preparation is one or more selected from the embodiments and preferred embodiments as defined herein in the description of the polymerization initiator.

In one embodiment of the polymer of the invention, referred to as "Embodiment 4", the polymerization initiator is a compound of Formula 5 or a Lewis base adduct thereof, as defined herein as "Embodiment 1" in the description of the polymerization initiator and including embodiments and preferred embodiments thereof.

In another embodiment of the polymer of the invention, the polymerization initiator is a compound of Formula 6 or a Lewis base adduct thereof, as defined herein as "Embodiment 2" in the description of the polymerization initiator and including embodiments and preferred embodiments thereof.

In yet another embodiment of the polymer of the invention, the polymerization initiator is selected from a compound of Formula 17, 18 or 19 or a Lewis base adduct thereof, as defined herein in the description of the polymerization initiator and including embodiments and preferred embodiments thereof.

The polymerization initiator of Formula 1, including the embodiments of Formulas 5, 6, 17, 18 and 19, may be reacted, optionally in the presence of a Lewis base, with a fraction of the total amount of monomers required for making the desired polymer and may then be stored for an amount of time, for example from seconds to weeks, before further reacting it with the remaining amount of monomers to complete the polymerization process. In one embodiment, the fraction of the total amount of monomers is from 1 to 40 monomer equivalents based on the amount of polymerization initiator.

In a preferred embodiment, the polymer of the invention is a modified polymer and is the product of
  firstly reacting a polymerization initiator of Formula 1, including Formulas 5, 6, 17, 18 and 19 and embodiments thereof, or a Lewis base adduct thereof with at least one type of polymerizable monomers selected from conjugated olefins and aromatic vinyl compounds, thus forming an omega,omega'-dianionic living polymer, and
  further reacting the omega,omega'-dianionic living polymer with a chain-end modifying agent as described below, thus forming the modified polymer as an omega, omega'-modified polymer which is modified with at least two polymer chain ends.

The polymer, including modified polymer, according to the third aspect of the invention can be represented structurally, for example, by the following Formulas P1 to P6:

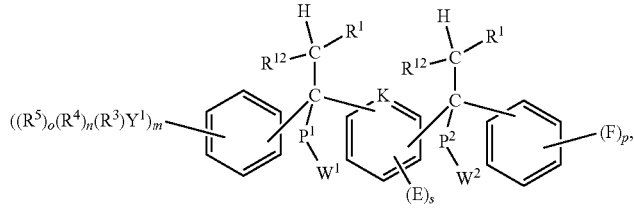

Formula P1

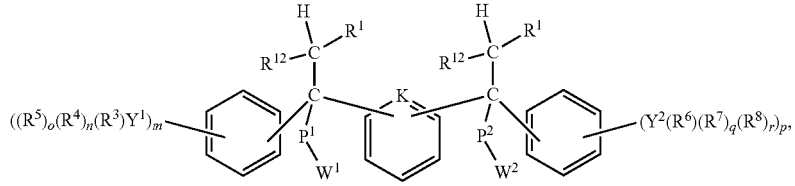

Formula P2

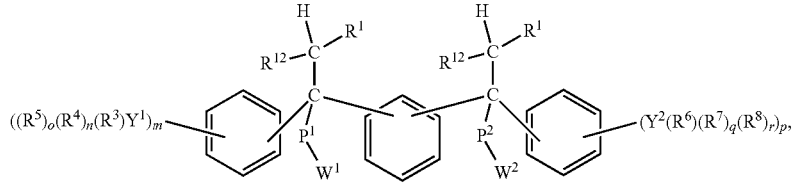

Formula P3

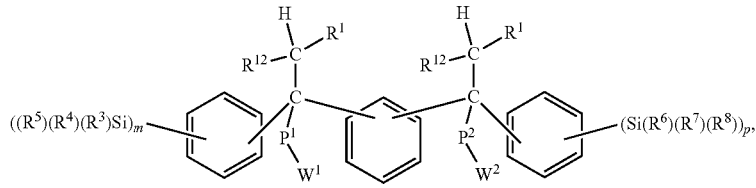

Formula P4

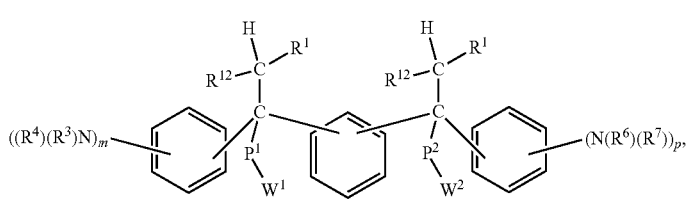

Formula P5

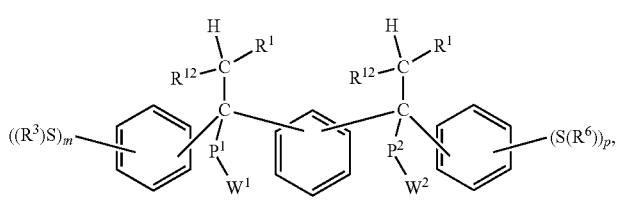

Formula P6 and Lewis base adducts thereof,
wherein
P¹ and P² are each independently a polymer chain formed from monomer units selected from conjugated olefins and aromatic vinyl compounds, especially butadiene, isoprene, styrene and alpha-methylstyrene, wherein the total number of monomer units per polymer molecule may range from 10 to 50.000, preferably from 20 to 40.000;
W¹ and W² are each independently selected from hydrogen and a chain end modifying group produced by reaction of the chain end of P¹ and/or P² with a chain-end modifying agent as described herein; and
all other substituents or groups are as generally defined for Formula 1 (with respect to Formula P1), Formula 5 (with respect to Formula P2), Formula 6 (with respect to Formula P3), Formula 17 (with respect to Formula P4), Formula 18 (with respect to Formula P5) and Formula 19 (with respect to Formula P6).

Polymers and modified polymers of Formulas P4, P5 and P6 are preferred.

Specific preferred polymers and modified polymers include the following ones, including Lewis base adducts thereof (with P¹ and P² being as herein defined):

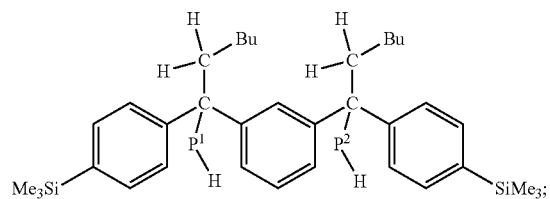

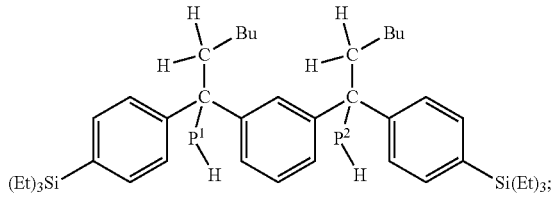

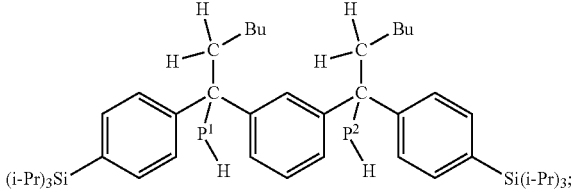

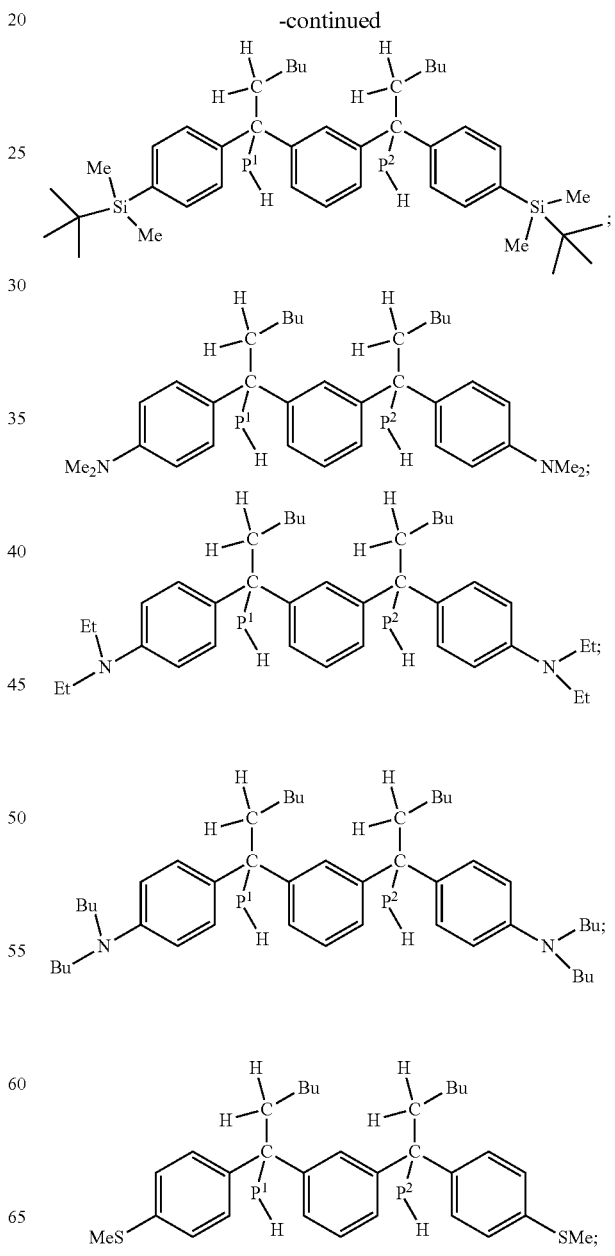

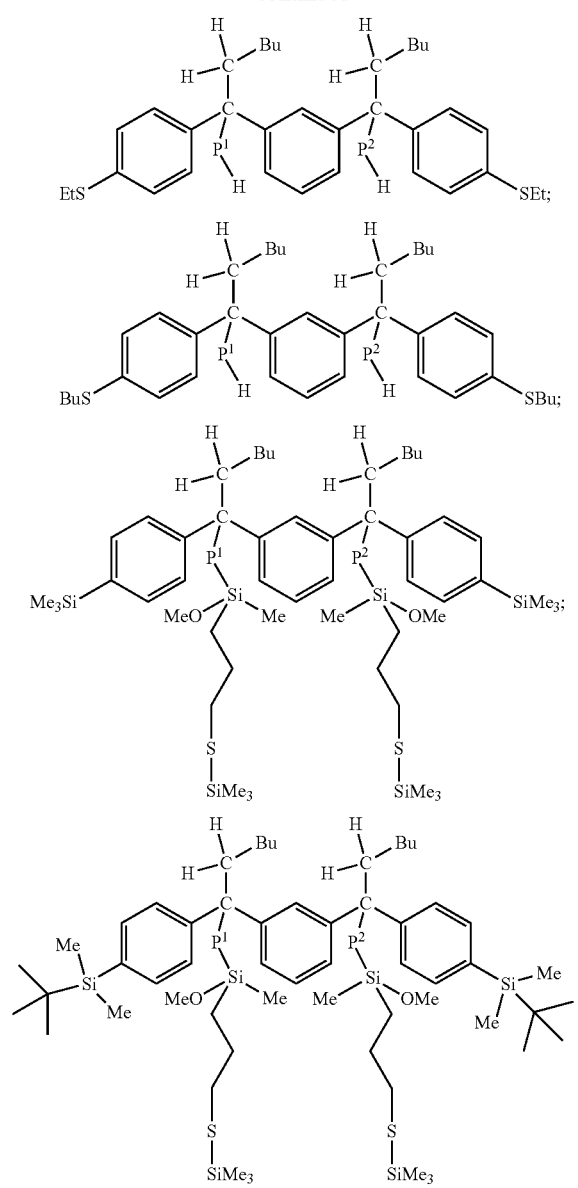
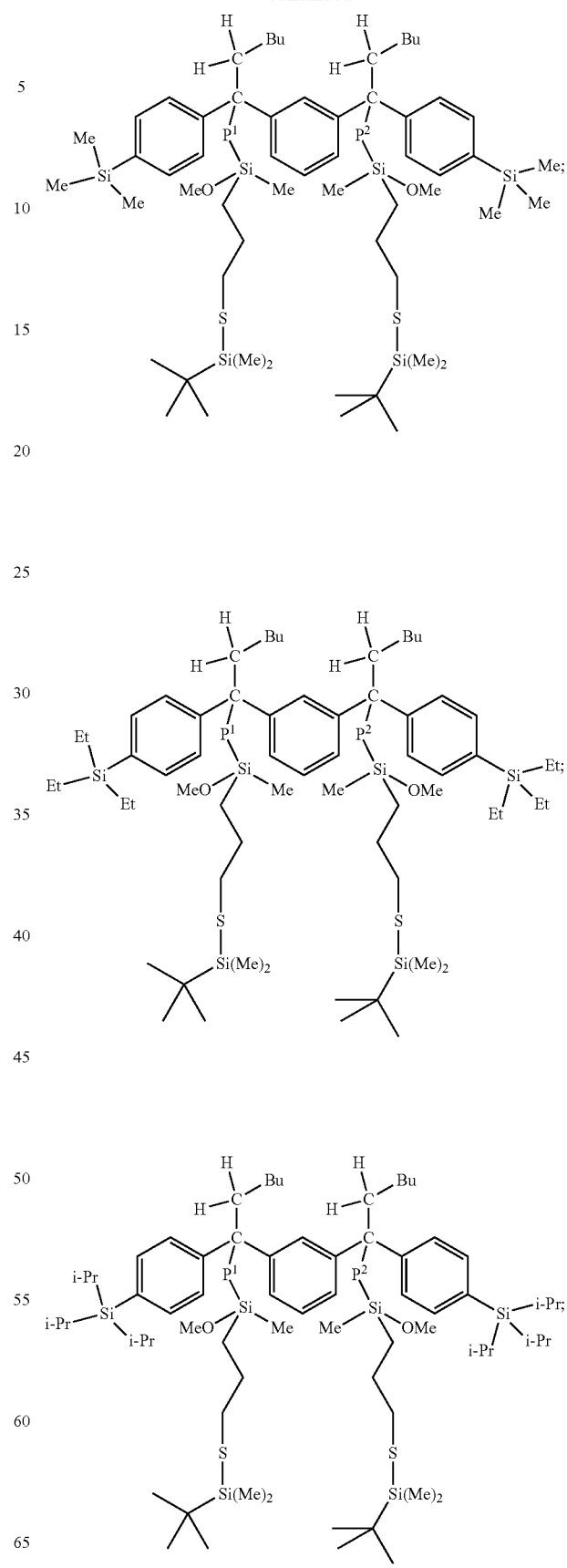

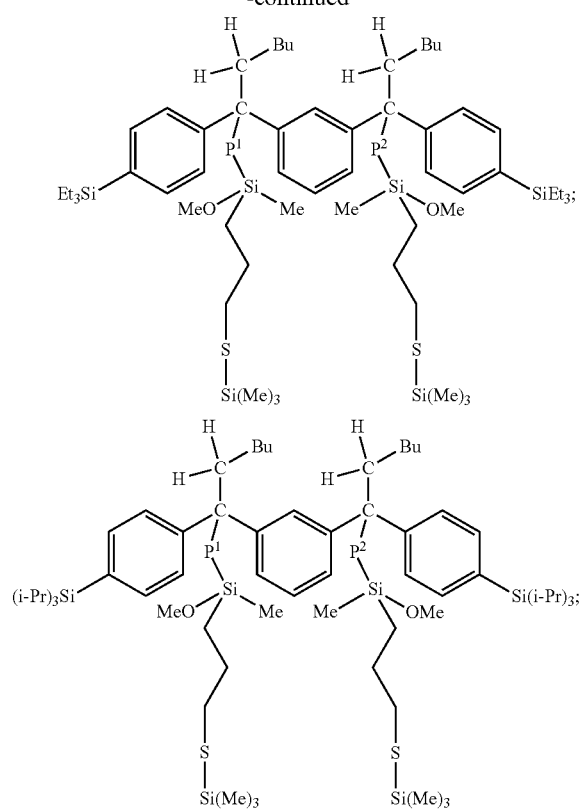
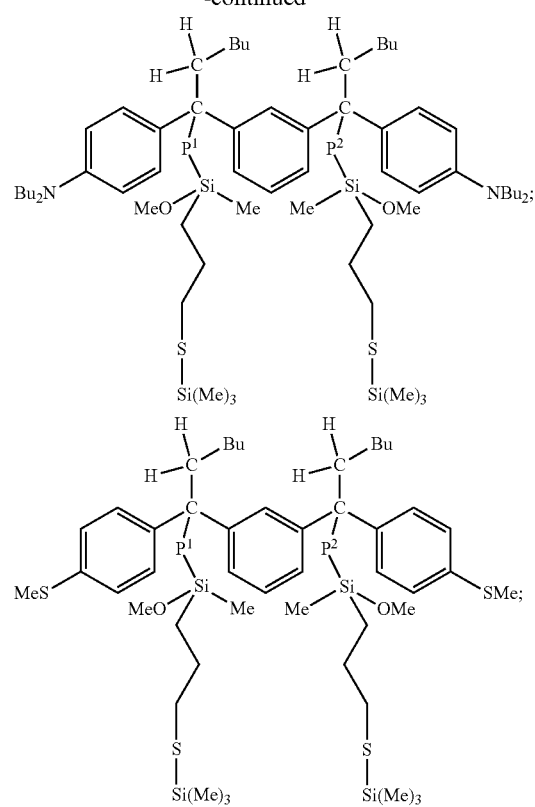
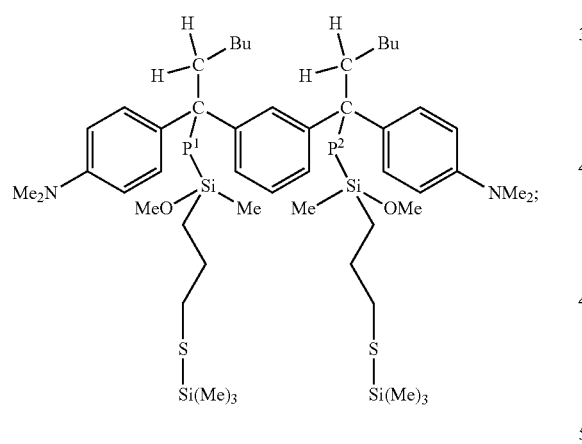
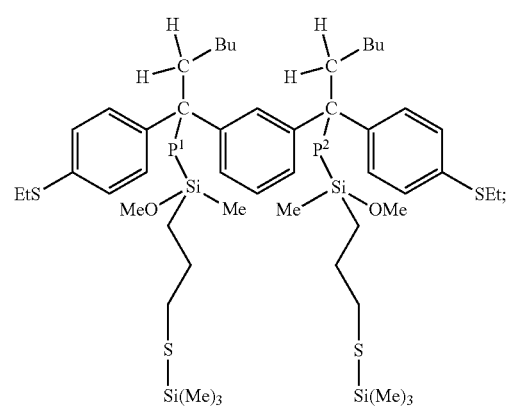
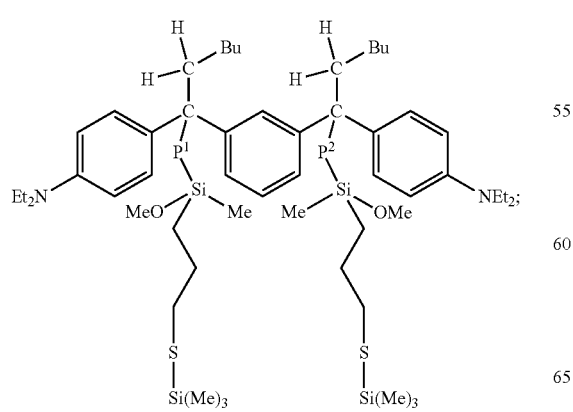
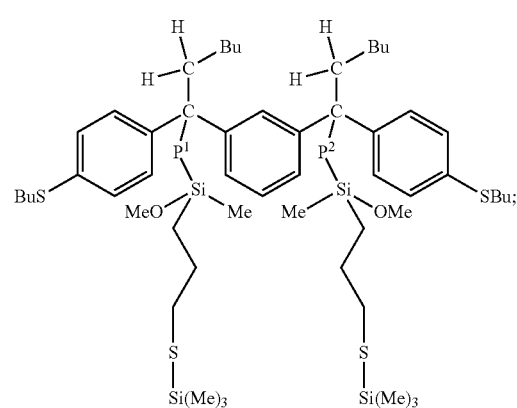

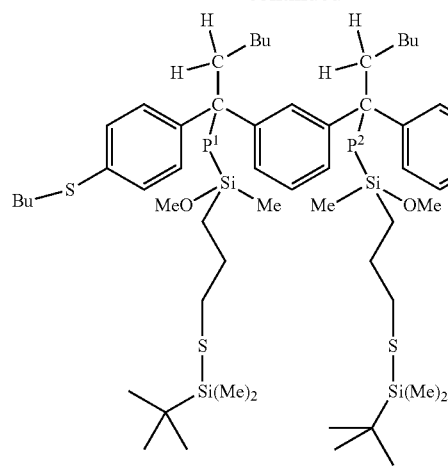
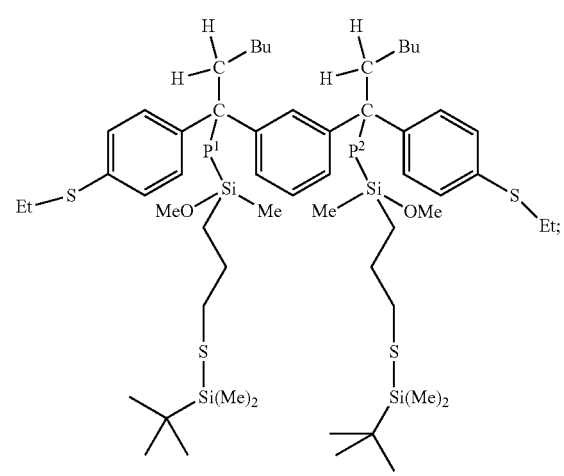
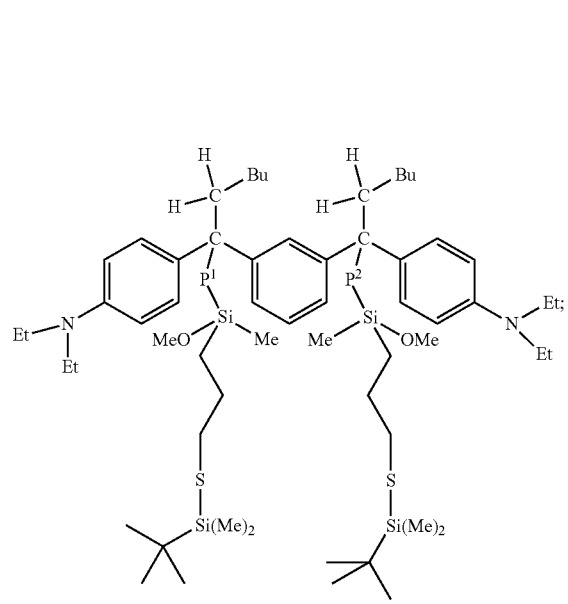
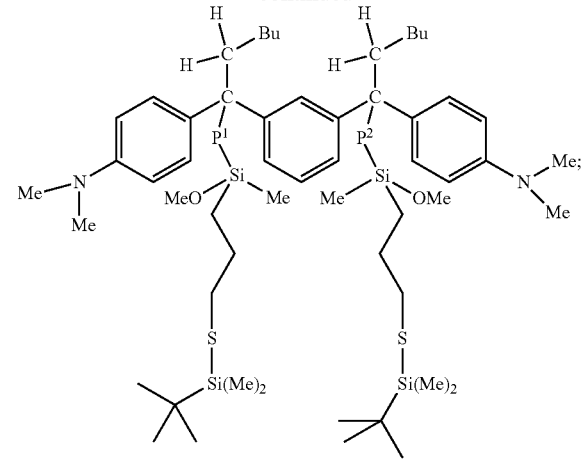
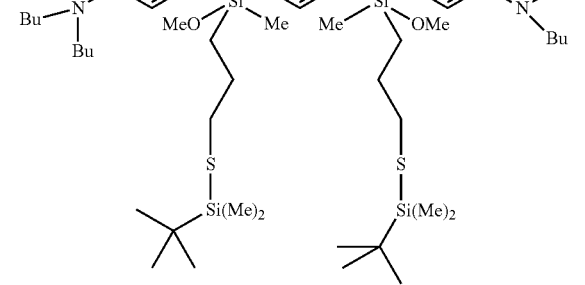
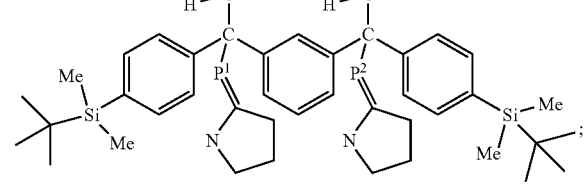
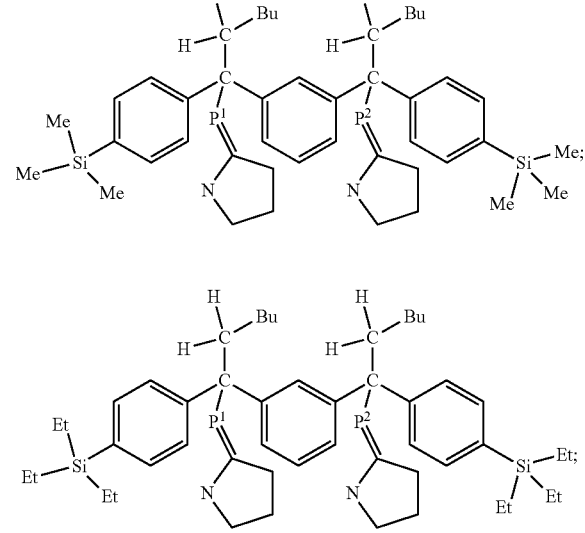

-continued

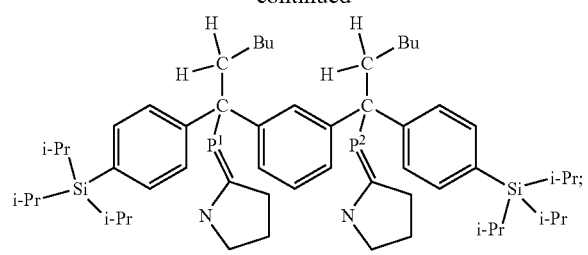

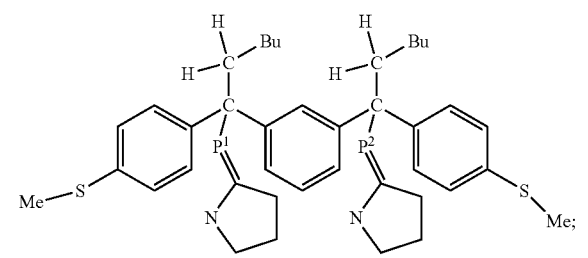

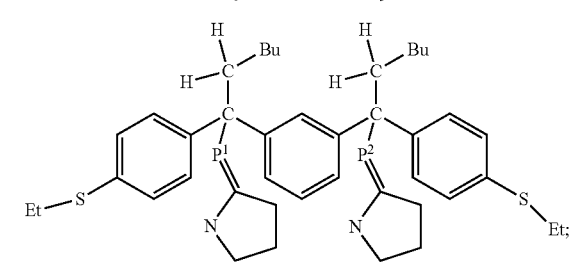

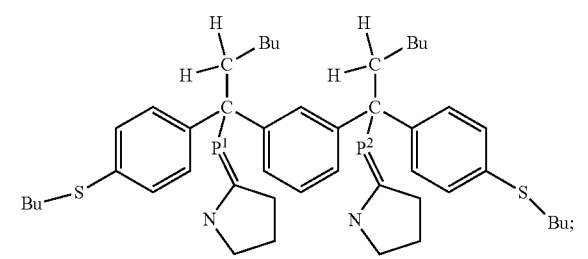

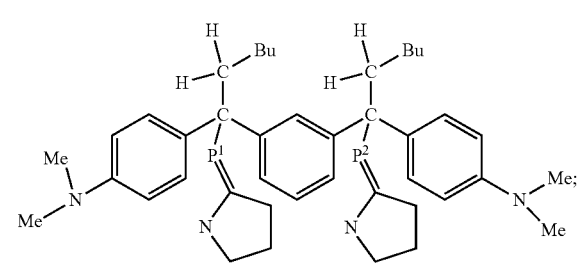

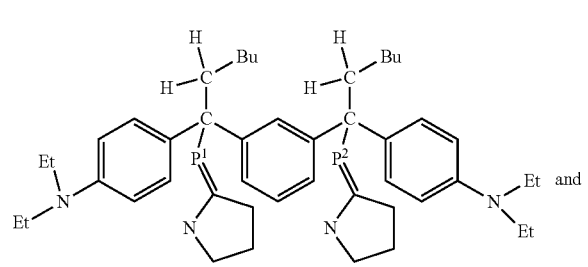

-continued

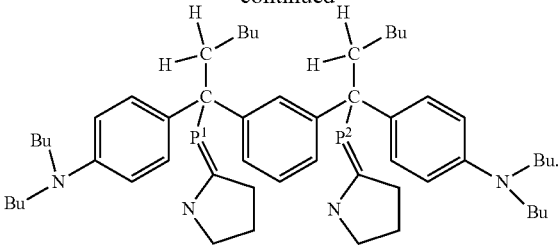

Moieties resulting from the process of chain end modification using chain end modifying agents having a terminal trihydrocarbylsilyl group, including trialkylsilyl, trialkylarylsilyl and triarylsilyl; trihydrocarbylstannyl group, including trialkylstannyl, trialkylarylstannyl and triarylstannyl; dihydrocarbylsilendeyl group, including dialkylsilendeyl, dialkylarylsilendiyl and diarylsilendiyl; or dihydrocarbylstannendiyl group, including dialkylstannendiyl, dialkylarylstannendiyl and diarylstannendiyl, are believed to function as protective groups, which prevent unintended subsequent reaction of the polymer chain. Such protective groups may be removed by exposure to a compound containing a reactive hydroxyl group (—OH), such as water, alcohols, anionic acids or organic acids (for example hydrochloric acid, sulfuric acid or carboxylic acids). Such conditions are typically present during vulcanization. In those cases where the terminal group of the chain-end modifying compound is sulfide-linked, the exposure to a reactive hydroxyl group and deprotection will result in the formation of an unprotected thiol group (—SH) as the terminal group of the polymer chain. Depending on the work-up conditions for the modified polymer (e.g., steam stripping), both the unprotected modified and the protected modified polymer may be present.

It is believed that certain terminal groups of the polymer, such as an unprotected thiol group, are reactive towards fillers such as silica and/or carbon black, which may result in a more homogeneous distribution of the filler within a polymer composition.

Specific preferred polymers containing unprotected terminal thiol groups include the following ones, including Lewis base adducts thereof (with $P^1$ and $P^2$ being as herein defined):

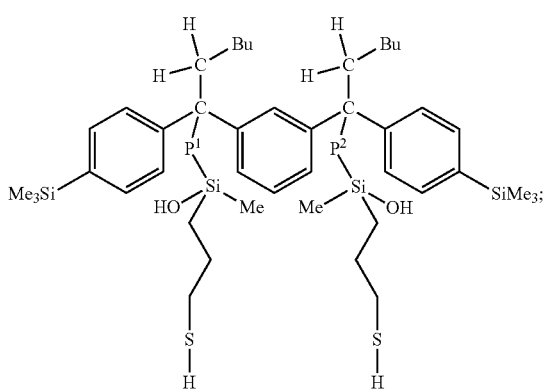

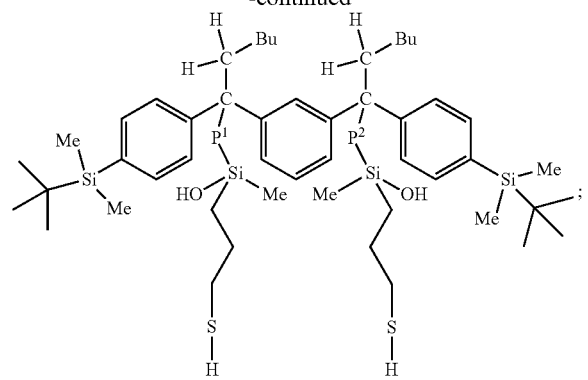
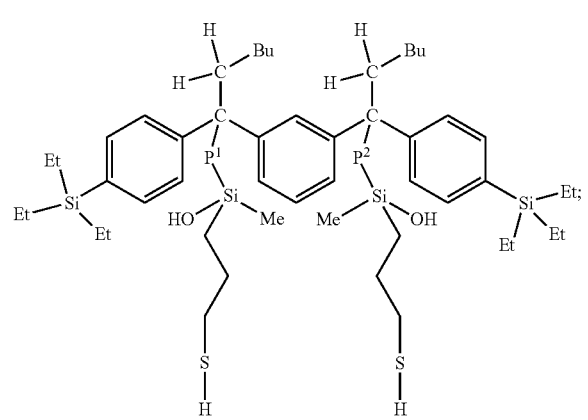
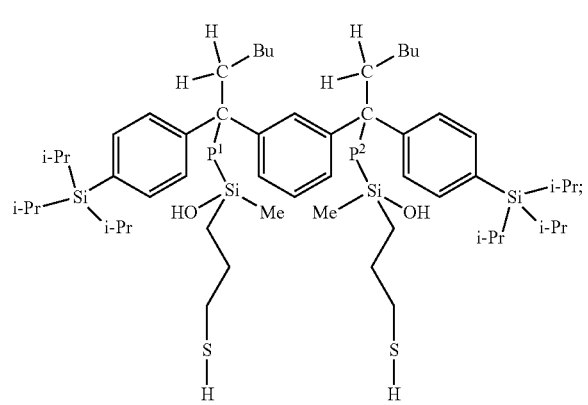
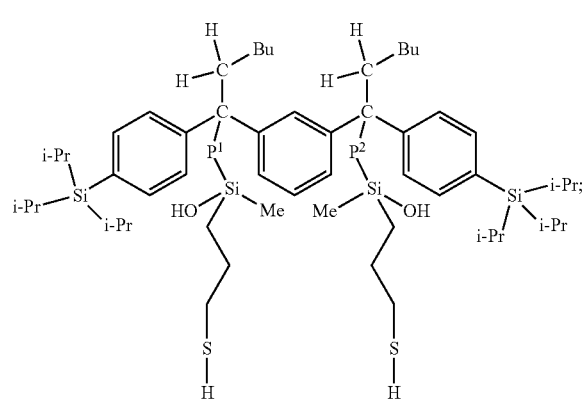
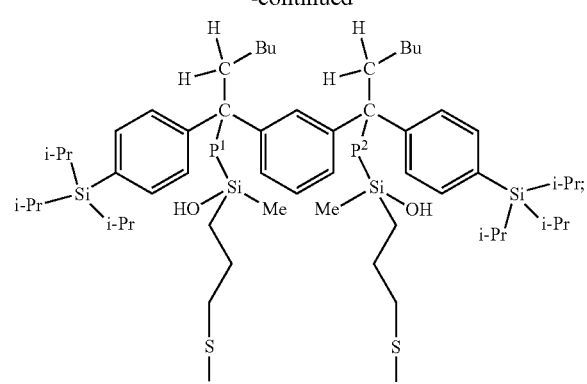
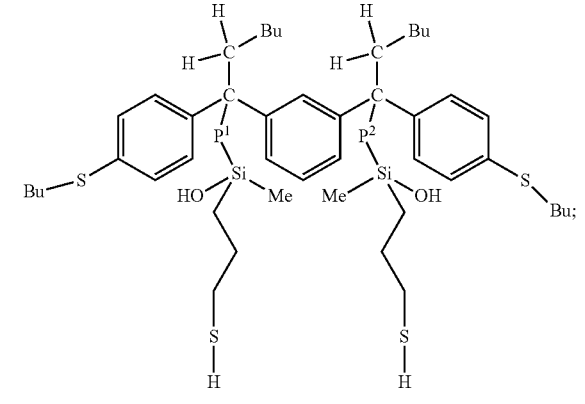
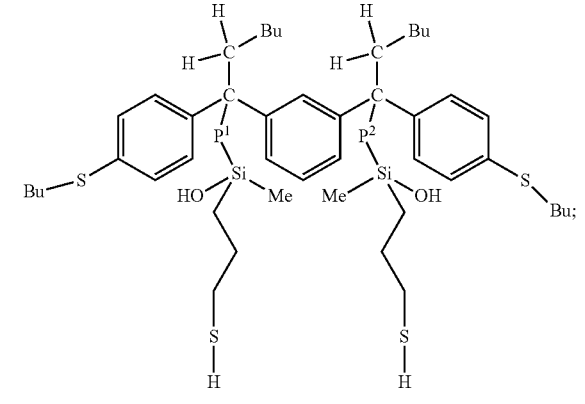
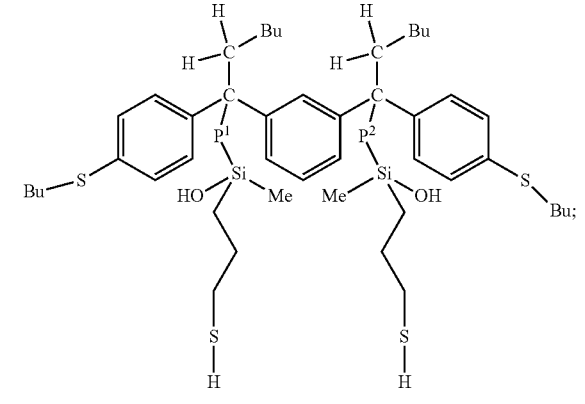

-continued

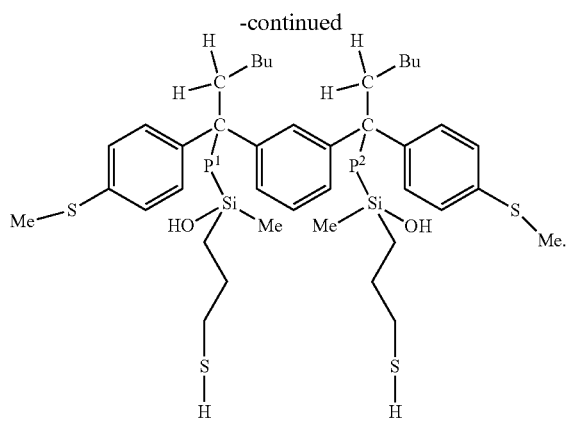

The reaction product as a chain-end modified polymer typically contains silanol groups and alkoxysilyl groups in a total amount from 0.0001 to 3.00 mmol/gram of polymer, preferably from 0.0005 to 1.8 mmol/gram, more preferably from 0.0010 to 1.0 mmol/gram and even more preferably from 0.0020 to 0.2 mmol/gram.

The reaction product as a chain-end modified polymer preferably contains sulfide groups (in the form of thiol groups and/or sulfide-linked protective groups) in a total amount of from 0.0001 to 0.80 mmol/gram of polymer, preferably from 0.0005 to 0.50 mmol/gram, more preferably from 0.0010 to 0.30 mmol/gram and even more preferably from 0.0020 to 0.20 mmol/gram of polymer.

For most applications, the polymer is preferably a homopolymer derived from a conjugated diolefin, a copolymer derived from a conjugated diolefin monomer with an aromatic vinyl monomer and/or a terpolymer of one or two types of conjugated diolefins with one or two types of aromatic vinyl compounds. Examples of particularly useful polymers include homopolymers of butadiene or isoprene and random or block co- and terpolymers of butadiene, isoprene and styrene, especially a random copolymer of butadiene with isoprene and a random or block copolymer of butadiene with styrene.

Although there are no specific limitations regarding the amount of aromatic vinyl monomer used in the polymer, for most applications aromatic vinyl monomers constitute from 1 to 60%, preferably from 2 to 55% and more preferably from 5 to 50% by weight, based on the total weight of the polymer. An amount of less than 2% by weight may lead to a deteriorated balance of rolling resistance, wet skid and abrasion resistance and to reduced tensile strength, whereas an amount of more than 60% by weight may lead to increased hysteresis loss. The polymer may be a block or random copolymer of an aromatic vinyl monomer, and preferably 40% by weight or more of the aromatic vinyl monomer units are linked singly, and 10% by weight or less are polymeric "blocks" of eight or more aromatic vinyl monomers linked successively (the length of successively linked aromatic vinyl units can be measured by an ozonolysis-gel permeation chromatography method developed by Tanaka et al. (Polymer. Vol. 22, pp. 1721-1723 (1981)). Copolymers outside this range tend to exhibit increased hysteresis loss.

Although there are no specific limitations regarding the content of 1,2-bonds and/or 3,4-bonds (hereinafter called "vinyl bond content") of the conjugated diolefin portion of the polymer, for most applications the vinyl bond content is less than 90% by weight, particularly preferably less than 80% by weight (based on the total weight of the polymer). If the vinyl content in the polymer exceeds 90% by weight, the resulting product may exhibit deteriorated tensile strength and abrasion resistance and a relatively large hysteresis loss.

Monomers

The monomers used in the preparation of the polymer of the invention are selected from conjugated olefins and aromatic vinyl compounds.

Suitable conjugated olefins include conjugated dienes, such as 1,3-butadiene, 2-alkyl-1,3-butadiene, isoprene (2-methyl-1,3-butadiene), 2,3-dimethyl-1,3-butadiene, 1,3-pentadiene, 2,4-hexadiene, 1,3-hexadiene, 1,3-heptadiene, 1,3-octadiene, 2-methyl-2,4-pentadiene, cyclopentadiene, 2,4-hexadiene and 1,3-cyclooctadiene and a combination of two or more thereof. 1,3-butadiene and isoprene are preferred conjugated olefins, and 1,3-butadiene is a particularly preferred one.

Suitable aromatic vinyl compounds include styrene, $C_{1-4}$ alkyl-substituted styrene, such as 2-methylstyrene, 3-methylstyrene, 4-methylstyrene, 2,4-dimethylstyrene, 2,4,6-trimethylstyrene, α-methylstyrene and stilbene, 2,4-diisopropylstyrene, 4-tert-butylstyrene, vinyl benzyl dimethylamine, (4-vinylbenzyl)dimethyl aminoethyl ether, N,N-dimethylaminoethyl styrene, tert-butoxystyrene and vinylpyridine and a combination of two or more thereof. Styrene is a particularly preferred aromatic vinyl compound.

In addition to the above-mentioned conjugated olefins and aromatic vinyl compounds, it is possible to make use of one or more monomers selected from olefins and nonconjugated diolefins, such as $C_2$-$C_{20}$ α-olefins and non-conjugated $C_4$-$C_{20}$ diolefins, especially norbornadiene, ethylidenenorbornene, 1,4-hexadiene, 1,5-hexadiene, 1,7-octadiene, 4-vinylcyclohexene and divinylbenzene including 1,2-divinylbenzene, 1,3-divinylbenzene and 1,4-divinylbenzene.

In one embodiment, the amount of divinylbenzene, including 1,2-divinylbenzene, 1,3-divinylbenzene and 1,4-divinylbenzene, is 1 mol % or less (based on the total molar amount of the monomers used to make the polymer).

Chain End Modifying Agents

For further control of polymer properties, one or more chain end modifying agents (or briefly "modifying agents") can be used for reaction with the terminal ends of the polymer chain(s) in the polymer of the invention. Generally, silane-sulfide omega chain end modifying agents such as disclosed in WO 2007/047943, WO 2009/148932, U.S. Pat. No. 6,229,036 and US 2013/0131263, each incorporated herein by reference in its entirety, can be used for this purpose, namely by reaction with the polymer (living anionic polymer) obtained by reaction of the polymerization initiator compound of the invention with a conjugated olefin or aromatic vinyl compound as the monomer component.

In a preferred embodiment, the chain end modifying agent is selected from one or more of the chain end modifying agents represented by the Formulas 8, 9, 10, 11, 12, 13, 14, 15 and 16 below and Lewis base adducts thereof.

Formula 8

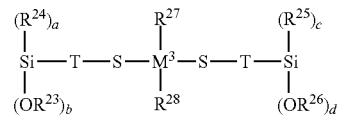

In Formula 8, $M^3$ is a silicon atom or a tin atom;
T is at least divalent and is selected from ($C_6$-$C_{18}$) aryl, ($C_7$-$C_{18}$) alkylaryl and ($C_1$-$C_{18}$) alkyl, wherein each group is optionally substituted with one or more groups selected from di($C_1$-$C_7$ hydrocarbyl)amino, bis(tri($C_1$-$C_{12}$ alkyl)silyl)amino, tris($C_1$-$C_7$ hydrocarbyl)silyl, ($C_7$-$C_{18}$) alkylaryl and ($C_6$-$C_{18}$) aryl;

$R^{23}$ and $R^{26}$ are each independently selected from ($C_1$-$C_4$) alkyl;

$R^{24}$, $R^{25}$, $R^{27}$ and $R^{28}$ are each independently selected from ($C_1$-$C_{18}$) alkyl, ($C_6$-$C_{18}$) aryl and ($C_7$-$C_{18}$) alkylaryl;

a and c are each independently selected from 0, 1 and 2; b and d are each independently selected from 1, 2 and 3; a+b=3; and c+d=3.

Specific preferred species of the chain end modifying agent of Formula 8 include the following compounds and their corresponding Lewis base adducts: (MeO)$_3$Si—(CH$_2$)$_3$—S—Si(Me)$_2$-S—(CH$_2$)$_3$—Si(OMe)$_3$, (MeO)$_3$Si—(CH$_2$)$_3$—S—Si(Et)$_2$-S—(CH$_2$)$_3$—Si(OMe)$_3$, (MeO)$_3$Si—(CH$_2$)$_3$—S—Si(Bu)$_2$-S—(CH$_2$)$_3$—Si(OMe)$_3$, (EtO)$_3$Si—(CH$_2$)$_3$—S—Si(Me)$_2$-S—(CH$_2$)$_3$—Si(OEt)$_3$, (EtO)$_3$Si—(CH$_2$)$_3$—S—Si(Et)$_2$-S—(CH$_2$)$_3$—Si(OEt)$_3$, (EtO)$_3$Si—(CH$_2$)$_3$—S—Si(Bu)$_2$-S—(CH$_2$)$_3$—Si(OEt)$_3$, (PrO)$_3$Si—(CH$_2$)$_3$—S—Si(Me)$_2$-S—(CH$_2$)$_3$—Si(OPr)$_3$, (PrO)$_3$Si—(CH$_2$)$_3$—S—Si(Et)$_2$-S—(CH$_2$)$_3$—Si(OPr)$_3$, (PrO)$_3$Si—(CH$_2$)$_3$—S—Si(Bu)$_2$-S—(CH$_2$)$_3$—Si(OPr)$_3$, (MeO)$_3$Si—(CH$_2$)$_2$—S—Si(Me)$_2$-S—(CH$_2$)$_2$—Si(OMe)$_3$, (MeO)$_3$Si—(CH$_2$)$_2$—S—Si(Et)$_2$-S—(CH$_2$)$_2$—Si(OMe)$_3$, (MeO)$_3$Si—(CH$_2$)$_2$—S—Si(Bu)$_2$-S—(CH$_2$)$_2$—Si(OMe)$_3$, (EtO)$_3$Si—(CH$_2$)$_2$—S—Si(Me)$_2$-S—(CH$_2$)$_2$—Si(OEt)$_3$, (EtO)$_3$Si—(CH$_2$)$_2$—S—Si(Et)$_2$-S—(CH$_2$)$_2$—Si(OEt)$_3$, (EtO)$_3$Si—(CH$_2$)$_2$—S—Si(Bu)$_2$-S—(CH$_2$)$_2$—Si(OEt)$_3$, (PrO)$_3$Si—(CH$_2$)$_2$—S—Si(Me)$_2$-S—(CH$_2$)$_2$—Si(OPr)$_3$, (PrO)$_3$Si—(CH$_2$)$_2$—S—Si(Et)$_2$-S—(CH$_2$)$_2$—Si(OPr)$_3$, (PrO)$_3$Si—(CH$_2$)$_2$—S—Si(Bu)$_2$-S—(CH$_2$)$_2$—Si(OPr)$_3$, (MeO)$_3$Si—CH$_2$—S—Si(Me)$_2$-S—CH$_2$—Si(OMe)$_3$, (MeO)$_3$Si—CH$_2$—S—Si(Et)$_2$-S—CH$_2$—Si(OMe)$_3$, (MeO)$_3$Si—CH$_2$—S—Si(Bu)$_2$-S—CH$_2$—Si(OMe)$_3$, (EtO)$_3$Si—CH$_2$—S—Si(Me)$_2$-S—CH$_2$—Si(OEt)$_3$, (EtO)$_3$Si—CH$_2$—S—Si(Et)$_2$-S—CH$_2$—Si(OEt)$_3$, (EtO)$_3$Si—CH$_2$—S—Si(Bu)$_2$-S—CH$_2$—Si(OEt)$_3$, (PrO)$_3$Si—CH$_2$—S—Si(Me)$_2$-S—CH$_2$—Si(OPr)$_3$, (PrO)$_3$Si—CH$_2$—S—Si(Et)$_2$-S—CH$_2$—Si(OPr)$_3$, (PrO)$_3$Si—CH$_2$—S—Si(Bu)$_2$-S—CH$_2$—Si(OPr)$_3$, (MeO)$_3$Si—CH$_2$—CMe$_2$-CH$_2$—S—Si(Me)$_2$-S—CH$_2$—CMe$_2$-CH$_2$—Si(OMe)$_3$, (MeO)$_3$Si—CH$_2$—CMe$_2$-CH$_2$—S—Si(Et)$_2$-S—CH$_2$—CMe$_2$-CH$_2$—Si(OMe)$_3$, (MeO)$_3$Si—CH$_2$—CMe$_2$-CH$_2$—S—Si(Bu)$_2$-S—CH$_2$—CMe$_2$-CH$_2$—Si(OMe)$_3$, (EtO)$_3$Si—CH$_2$—CMe$_2$-CH$_2$—S—Si(Me)$_2$-S—CH$_2$—CMe$_2$-CH$_2$—Si(OEt)$_3$, (EtO)$_3$Si—CH$_2$—CMe$_2$-CH$_2$—S—Si(Et)$_2$-S—CH$_2$—CMe$_2$-CH$_2$—Si(OEt)$_3$, (EtO)$_3$Si—CH$_2$—CMe$_2$-CH$_2$—S—Si(Bu)$_2$-S—CH$_2$—CMe$_2$-CH$_2$—Si(OEt)$_3$, (PrO)$_3$Si—CH$_2$—CMe$_2$-CH$_2$—S—Si(Me)$_2$-S—CH$_2$—CMe$_2$-CH$_2$—S(OPr)$_3$, (PrO)$_3$Si—CH$_2$—CMe$_2$-CH$_2$—S—Si(Et)$_2$-S—CH$_2$—CMe$_2$-CH$_2$—Si(OPr)$_3$, (PrO)$_3$Si—CH$_2$—CMe$_2$-CH$_2$—S—Si(Bu)$_2$-S—CH$_2$—CMe$_2$-CH$_2$—Si(OPr)$_3$, (MeO)$_3$Si—CH$_2$—C(H)Me-CH$_2$—S—Si(Me)$_2$-S—CH$_2$—C(H)Me-CH$_2$—Si(OMe)$_3$, (MeO)$_3$Si—CH$_2$—C(H)Me-CH$_2$—S—Si(Et)$_2$-S—CH$_2$—C(H)Me-CH$_2$—Si(OMe)$_3$, (MeO)$_3$Si—CH$_2$—(H)Me-CH$_2$—S—Si(Bu)$_2$-S—CH$_2$—C(H)Me-CH$_2$—Si(OEt)$_3$, (EtO)$_3$Si—CH$_2$—C(H)Me-CH$_2$—S—Si(Me)$_2$-S—CH$_2$—C(H)Me-CH$_2$—Si(OEt)$_3$, (EtO)$_3$Si—CH$_2$—C(H)Me-CH$_2$—S—Si(Et)$_2$-S—CH$_2$—C(H)Me-CH$_2$—Si(OEt)$_3$, (EtO)$_3$Si—CH$_2$—C(H)Me-CH$_2$—S—Si(Bu)$_2$-S—CH$_2$—C(H)Me-CH$_2$—Si(OEt)$_3$, (PrO)$_3$Si—CH$_2$—C(H)Me-CH$_2$—S—Si(Me)$_2$-S—CH$_2$—C(H)Me-CH$_2$—Si(OPr)$_3$, (PrO)$_3$Si—CH$_2$—C(H)Me-CH$_2$—S—Si(Et)$_2$-S—CH$_2$—C(H)Me-CH$_2$—Si(OPr)$_3$, (PrO)$_3$Si—CH$_2$—C(H)Me-CH$_2$—S—Si(Bu)$_2$-S—CH$_2$—C(H)Me-CH$_2$—Si(OPr)$_3$, (MeO)$_2$(Me)Si—(CH$_2$)$_3$—S—Si(Me)$_2$-S—(CH$_2$)$_3$—Si(OMe)$_2$(Me), (MeO)$_2$(Me)Si—(CH$_2$)$_3$—S—Si(Et)$_2$-S—(CH$_2$)$_3$—Si(OMe)$_2$(Me), (MeO)$_2$(Me)Si—(CH$_2$)$_3$—S—Si(Bu)$_2$-S—(CH$_2$)$_3$—Si(OMe)$_2$(Me), (EtO)$_2$(Me)Si—(CH$_2$)$_3$—S—Si(Me)$_2$-S—(CH$_2$)$_3$—Si(OEt)$_2$(Me), (EtO)$_2$(Me)Si—(CH$_2$)$_3$—S—Si(Et)$_2$-S—(CH$_2$)$_3$—Si(OEt)$_2$(Me), (EtO)$_2$(Me)Si—(CH$_2$)$_3$—S—Si(Bu)$_2$-S—(CH$_2$)$_3$—Si(OEt)$_2$(Me), (PrO)$_2$(Me)Si—(CH$_2$)$_3$—S—Si(Me)$_2$-S—(CH$_2$)$_3$—Si(OPr)$_2$(Me), (PrO)$_2$(Me)Si—(CH$_2$)$_3$—S—Si(Et)$_2$-S—(CH$_2$)$_3$—Si(OPr)$_2$(Me), (PrO)$_2$(Me)Si—(CH$_2$)$_3$—S—Si(Bu)$_2$-S—(CH$_2$)$_3$—Si(OPr)$_2$(Me), (MeO)$_2$(Me)Si—(CH$_2$)$_2$—S—Si(Me)$_2$-S—(CH$_2$)$_2$—Si(OMe)$_2$(Me), (MeO)$_2$(Me)Si—(CH$_2$)$_2$—S—Si(Et)$_2$-S—(CH$_2$)$_2$—Si(OMe)$_2$(Me), (MeO)$_2$(Me)Si—(CH$_2$)$_2$—S—Si(Bu)$_2$-S—(CH$_2$)$_2$—Si(OMe)$_2$(Me), (EtO)$_2$(Me)Si—(CH$_2$)$_2$—S—Si(Me)$_2$-S—(CH$_2$)$_2$—Si(OEt)$_2$(Me), (EtO)$_2$(Me)Si—(CH$_2$)$_2$—S—Si(Et)$_2$-S—(CH$_2$)$_2$—Si(OEt)$_2$(Me), (EtO)$_2$(Me)Si—(CH$_2$)$_2$—S—Si(Bu)$_2$-S—(CH$_2$)$_2$—Si(OEt)$_2$(Me), (PrO)$_2$(Me)Si—(CH$_2$)$_2$—S—Si(Me)$_2$-S—(CH$_2$)$_2$—Si(OPr)$_2$(Me), (PrO)$_2$(Me)Si—(CH$_2$)$_2$—S—Si(Et)$_2$-S—(CH$_2$)$_2$—Si(OPr)$_2$(Me), (PrO)$_2$(Me)Si—(CH$_2$)$_2$—S—Si(Bu)$_2$-S—(CH$_2$)$_2$—Si(OPr)$_2$(Me), (MeO)$_2$(Me)Si—CH$_2$—S—Si(Me)$_2$-S—CH$_2$—Si(OMe)$_2$(Me), (MeO)$_2$(Me)Si—CH$_2$—S—Si(Et)$_2$-S—CH$_2$—Si(OMe)$_2$(Me), (MeO)$_2$(Me)Si—CH$_2$—S—Si(Bu)$_2$-S—CH$_2$—Si(OMe)$_2$(Me), (EtO)$_2$(Me)Si—CH$_2$—S—Si(Me)$_2$-S—CH$_2$—Si(OEt)$_2$(Me), (EtO)$_2$(Me)Si—CH$_2$—S—Si(Et)$_2$-S—CH$_2$—Si(OEt)$_2$(Me), (EtO)$_2$(Me)Si—CH$_2$—S—Si(Bu)$_2$-S—CH$_2$—Si(OEt)$_2$(Me), (PrO)$_2$(Me)Si—CH$_2$—S—Si(Me)$_2$-S—CH$_2$—Si(OPr)$_2$(Me), (PrO)$_2$(Me)Si—CH$_2$—S—Si(Et)$_2$-S—CH$_2$—Si(OPr)$_2$(Me), (PrO)$_2$(Me)Si—CH$_2$—S—Si(Bu)$_2$-S—CH$_2$—Si(OPr)$_2$(Me), (MeO)$_2$(Me)Si—CH$_2$—CMe$_2$-CH$_2$—S—Si(Me)$_2$-S—CH$_2$—CMe$_2$-CH$_2$—Si(OMe)$_2$(Me), (MeO)$_2$(Me)Si—CH$_2$—CMe$_2$-CH$_2$—S—Si(Et)$_2$-S—CH$_2$—CMe$_2$-CH$_2$—Si(OMe)$_2$(Me), (MeO)$_2$(Me)Si—CH$_2$—CMe$_2$-CH$_2$—S—Si(Bu)$_2$-S—CH$_2$—CMe$_2$-CH$_2$—Si(OMe)$_2$(Me), (EtO)$_2$(Me)Si—CH$_2$—CMe$_2$-CH$_2$—S—Si(Me)$_2$-S—CH$_2$—CMe$_2$-CH$_2$—Si(OEt)$_2$(Me), (EtO)$_2$(Me)Si—CH$_2$—CMe$_2$-CH$_2$—S—Si(Et)$_2$-S—CH$_2$—CMe$_2$-CH$_2$—Si(OEt)$_2$(Me), (EtO)$_2$(Me)Si—CH$_2$—CMe$_2$-CH$_2$—S—Si(Bu)$_2$-S—CH$_2$—CMe$_2$-CH$_2$—Si(OEt)$_2$(Me), (PrO)$_2$(Me)Si—CH$_2$—CMe$_2$-CH$_2$—S—Si(Me)$_2$-S—CH$_2$—CMe$_2$-CH$_2$—Si(OPr)$_2$(Me), (PrO)$_2$(Me)Si—CH$_2$—CMe$_2$-CH$_2$—S—Si(Et)$_2$-S—CH$_2$—CMe$_2$-CH$_2$—Si(OPr)$_2$(Me), (PrO)$_2$(Me)Si—CH$_2$—CMe$_2$-CH$_2$—S—Si(Bu)$_2$-S—CH$_2$—CMe$_2$-CH$_2$—Si(OPr)$_2$(Me), (MeO)$_2$(Me)Si—CH$_2$—C(H)Me-CH$_2$—S—Si(Me)$_2$-S—CH$_2$—C(H)Me-CH$_2$—Si(OMe)$_2$(Me), (MeO)$_2$(Me)Si—CH$_2$—C(H)Me-CH$_2$—S—Si(Et)$_2$-S—CH$_2$—C(H)Me-CH$_2$—Si(OMe)$_2$(Me), (MeO)$_2$(Me)Si—CH$_2$—C(H)Me-CH$_2$—S—Si(Bu)$_2$-S—CH$_2$—C(H)Me-CH$_2$—Si(OMe)$_2$(Me), (EtO)$_2$(Me)Si—CH$_2$—C(H)Me-CH$_2$—S—Si(Me)$_2$-S—CH$_2$—C(H)Me-CH$_2$—Si(OEt)$_2$(Me), (EtO)$_2$(Me)Si—CH$_2$—C(H)Me-CH$_2$—S—Si(Et)$_2$-S—CH$_2$—C(H)Me-CH$_2$—Si(OEt)$_2$(Me), (EtO)$_2$(Me)Si—CH$_2$—C(H)Me-CH$_2$—S—Si(Bu)$_2$-S—CH$_2$—C(H)Me-CH$_2$—Si(OEt)$_2$(Me), (PrO)$_2$(Me)Si—CH$_2$—C(H)Me-CH$_2$—S—Si(Me)$_2$-S—CH$_2$—C(H)Me-CH$_2$—Si(OPr)$_2$(Me), (PrO)$_2$(Me)Si—CH$_2$—C(H)Me-CH$_2$—S—Si(Et)$_2$-S—CH$_2$—C(H)Me-CH$_2$—Si(OPr)$_2$(Me), (PrO)$_2$(Me)Si—CH$_2$—C(H)Me-CH$_2$—S—Si(Bu)$_2$-S—CH$_2$—C(H)Me-CH$_2$—Si(OPr)$_2$(Me), (MeO)$_3$Si—(CH$_2$)$_3$—S—Sn(Me)$_2$-S—(CH$_2$)$_3$—Si(OMe)$_3$, (MeO)$_3$Si—(CH$_2$)$_3$—S—Sn(Et)$_2$-S—(CH$_2$)$_3$—Si(OMe)$_3$, (MeO)$_3$Si—(CH$_2$)$_3$—S—Sn(Bu)$_2$-S—(CH$_2$)$_3$—Si(OMe)$_3$, (EtO)$_3$Si—(CH$_2$)$_3$—S—Sn(Me)$_2$-S—(CH$_2$)$_3$—Si(OEt)$_3$, (EtO)$_3$Si—(CH$_2$)$_3$—S—Sn(Et)$_2$-S—(CH$_2$)$_3$—Si(OEt)$_3$, (EtO)$_3$Si—(CH$_2$)$_3$—S—Sn(Bu)$_2$-S—(CH$_2$)$_3$—Si(OEt)$_3$, (PrO)$_3$Si—(CH$_2$)$_3$—S—Sn(Me)$_2$-S—(CH$_2$)$_3$—Si(OPr)$_3$, (PrO)$_3$Si—(CH$_2$)$_3$—S—Sn(Et)$_2$-S—(CH$_2$)$_3$—Si(OPr)$_3$, (PrO)$_3$Si—(CH$_2$)$_3$—S—Sn(Bu)$_2$-S—(CH$_2$)$_3$—Si (OPr)₃, (MeO)₃Si—(CH₂)₂—S—Sn(Me)₂-S—(CH₂)₂—Si(OMe)₃, (MeO)₃Si—(CH₂)₂—S—Sn(Et)₂-S—(CH₂)₂—Si(OMe)₃, (MeO)₃Si—(CH₂)₂—S—Sn(Bu)₂-S—(CH₂)₂—Si(OMe)₃, (EtO)₃Si—(CH₂)₂—S—Sn(Me)₂-S—(CH₂)₂—Si(OEt)₃, (EtO)₃Si—(CH₂)₂—S—Sn(Et)₂-S—(CH₂)₂—Si(OEt)₃, (EtO)₃Si—(CH₂)₂—S—Sn(Bu)₂-S—(CH₂)₂—Si(OEt)₃, (PrO)₃Si—(CH₂)₂—S—Sn(Me)₂-S—(CH₂)₂—Si(OPr)₃, (PrO)₃Si—(CH₂)₂—S—Sn(Et)₂-S—(CH₂)₂—Si(OPr)₃, (PrO)₃Si—(CH₂)₂—S—Sn(Bu)₂-S—(CH₂)₂—Si(OPr)₃, (MeO)₃Si—CH₂—S—Sn(Me)₂-S—CH₂—Si(OMe)₃, (MeO)₃Si—CH₂—S—Sn(Et)₂-S—CH₂—Si(OMe)₃, (MeO)₃Si—CH₂—S—Sn(Bu)₂-S—CH₂—Si(OMe)₃, (EtO)₃Si—CH₂—S—Sn(Me)₂-S—CH₂—Si(OEt)₃, (EtO)₃Si—CH₂—S—Sn(Et)₂-S—CH₂—Si(OEt)₃, (EtO)₃Si—CH₂—S—Sn(Bu)₂-S—CH₂—Si(OEt)₃, (PrO)₃Si—CH₂—S—Sn(Me)₂-S—CH₂—Si(OPr)₃, (PrO)₃Si—CH₂—S—Sn(Et)₂-S—CH₂—Si(OPr)₃, (PrO)₃Si—CH₂—S—Sn(Bu)₂-S—CH₂—Si(OPr)₃, (MeO)₃Si—CH₂—CMe₂-CH₂—S—Sn(Me)₂-S—CH₂—CMe₂-CH₂—Si(OMe)₃, (MeO)₃Si—CH₂—CMe₂-CH₂—S—Sn(Et)₂-S—CH₂—CMe₂-CH₂—Si(OMe)₃, (MeO)₃Si—CH₂—CMe₂-CH₂—S—Sn(Bu)₂-S—CH₂—CMe₂-CH₂—Si(OMe)₃, (EtO)₃Si—CH₂—CMe₂-CH₂—S—Sn(Me)₂-S—CH₂—CMe₂-CH₂—Si(OEt)₃, (EtO)₃Si—CH₂—CMe₂-CH₂—S—Sn(Et)₂-S—CH₂—CMe₂-CH₂—Si(OEt)₃, (EtO)₃Si—CH₂—CMe₂-CH₂—S—Sn(Bu)₂-S—CH₂—CMe₂-CH₂—Si(OEt)₃, (PrO)₃Si—CH₂—CMe₂-CH₂—S—Sn(Me)₂-S—CH₂—CMe₂-CH₂—Si(OPr)₃, (PrO)₃Si—CH₂—CMe₂-CH₂—S—Sn(Et)₂-S—CH₂—CMe₂-CH₂—Si(OPr)₃, (PrO)₃Si—CH₂—CMe₂-CH₂—S—Sn(Bu)₂-S—CH₂—CMe₂-CH₂—Si(OPr)₃, (MeO)₃Si—CH₂—C(H)Me-CH₂—S—Sn(Me)₂-S—CH₂—C(H)Me-CH₂—Si(OMe)₃, (MeO)₃Si—CH₂—C(H)Me-CH₂—S—Sn(Et)₂-S—CH₂—C(H)Me-CH₂—Si(OMe)₃, (MeO)₃Si—CH₂—C(H)Me-CH₂—S—Sn(Bu)₂-S—CH₂—C(H)Me-CH₂—Si(OMe)₃, (EtO)₃Si—CH₂—C(H)Me-CH₂—S—Sn(Me)₂-S—CH₂—C(H)Me-CH₂—Si(OEt)₃, (EtO)₃Si—CH₂—C(H)Me-CH₂—S—Sn(Et)₂-S—CH₂—C(H)Me-CH₂—Si(OEt)₃, (EtO)₃Si—CH₂—C(H)Me-CH₂—S—Sn(Bu)₂-S—CH₂—C(H)Me-CH₂—Si(OEt)₃, (PrO)₃Si—CH₂—C(H)Me-CH₂—S—Sn(Me)₂-S—CH₂—C(H)Me-CH₂—Si(OPr)₃, (PrO)₃Si—CH₂—C(H)Me-CH₂—S—Sn(Et)₂-S—CH₂—C(H)Me-CH₂—Si(OPr)₃, (PrO)₃Si—CH₂—C(H)Me-CH₂—S—Sn(Bu)₂-S—CH₂—C(H)Me-CH₂—Si(OPr)₃, (MeO)₂(Me)Si—(CH₂)₃—S—Sn(Me)₂-S—(CH₂)₃—Si(OMe)₂(Me), (MeO)₂(Me)Si—(CH₂)₃—S—Sn(Et)₂-S—(CH₂)₃—Si(OMe)₂(Me), (MeO)₂(Me)Si—(CH₂)₃—S—Sn(Bu)₂-S—(CH₂)₃—Si(OMe)₂(Me), (EtO)₂(Me)Si—(CH₂)₃—S—Sn(Me)₂-S—(CH₂)₃—Si(OEt)₂(Me), (EtO)₂(Me)Si—(CH₂)₃—S—Sn(Et)₂-S—(CH₂)₃—Si(OEt)₂(Me), (EtO)₂(Me)Si—(CH₂)₃—S—Sn(Bu)₂-S—(CH₂)₃—Si(OEt)₂(Me), (PrO)₂(Me)Si—(CH₂)₃—S—Sn(Me)₂-S—(CH₂)₃—Si(OPr)₂(Me), (PrO)₂(Me)Si—(CH₂)₃—S—Sn(Et)₂-S—(CH₂)₃—Si(OPr)₂(Me), (PrO)₂(Me)Si—(CH₂)₃—S—Sn(Bu)₂-S—(CH₂)₃—Si(OPr)₂(Me), (MeO)₂(Me)Si—(CH₂)₂—S—Sn(Me)₂-S—(CH₂)₂—Si(OMe)₂(Me), (MeO)₂(Me)Si—(CH₂)₂—S—Sn(Et)₂-S—(CH₂)₂—Si(OMe)₂(Me), (MeO)₂(Me)Si—(CH₂)₂—S—Sn(Bu)₂-S—(CH₂)₂—Si(OMe)₂(Me), (EtO)₂(Me)Si—(CH₂)₂—S—Sn(Me)₂-S—(CH₂)₂—Si(OEt)₂(Me), (EtO)₂(Me)Si—(CH₂)₂—S—Sn(Et)₂-S—(CH₂)₂—Si(OEt)₂(Me), (EtO)₂(Me)Si—(CH₂)₂—S—Sn(Bu)₂-S—(CH₂)₂—Si(OEt)₂(Me), (PrO)₂(Me)Si—(CH₂)₂—S—Sn(Me)₂-S—(CH₂)₂—Si(OPr)₂(Me), (PrO)₂(Me)Si—(CH₂)₂—S—Sn(Et)₂-S—(CH₂)₂—Si(OPr)₂(Me), (PrO)₂(Me)Si—(CH₂)₂—S—Sn(Bu)₂-S—(CH₂)₂—Si(OPr)₂(Me), (MeO)₂(Me)Si—CH₂—S—Sn(Me)₂-S—CH₂—Si(OMe)₂(Me), (MeO)₂(Me)Si—CH₂—S—Sn(Et)₂-S—CH₂—Si(OMe)₂(Me), (MeO)₂(Me)Si—CH₂—S—Sn(Bu)₂-S—CH₂—Si(OMe)₂(Me), (EtO)₂(Me)Si—CH₂—S—Sn(Me)₂-S—CH₂—Si(OEt)₂(Me), (EtO)₂(Me)Si—CH₂—S—Sn(Et)₂-S—CH₂—Si(OEt)₂(Me), (EtO)₂(Me)Si—CH₂—S—Sn(Bu)₂-S—CH₂—Si(OEt)₂(Me), (PrO)₂(Me)Si—CH₂—S—Sn(Me)₂-S—CH₂—Si(OPr)₂(Me), (PrO)₂(Me)Si—CH₂—S—Sn(Et)₂-S—CH₂—Si(OPr)₂(Me), (PrO)₂(Me)Si—CH₂—S—Sn(Bu)₂-S—CH₂—Si(OPr)₂(Me), (MeO)₂(Me)Si—CH₂—CMe₂-CH₂—S—Sn(Me)₂-S—CH₂—CMe₂-CH₂—Si(OMe)₂(Me), (MeO)₂(Me)Si—CH₂—CMe₂-CH₂—S—Sn(Et)₂-S—CH₂—CMe₂-CH₂—Si(OMe)₂(Me), (MeO)₂(Me)Si—CH₂—CMe₂-CH₂—S—Sn(Bu)₂-S—CH₂—CMe₂-CH₂—Si(OMe)₂(Me), (EtO)₂(Me)Si—CH₂—CMe₂-CH₂—S—Sn(Me)₂-S—CH₂—CMe₂-CH₂—Si(OEt)₂(Me), (EtO)₂(Me)Si—CH₂—CMe₂-CH₂—S—Sn(Et)₂-S—CH₂—CMe₂-CH₂—Si(OEt)₂(Me), (EtO)₂(Me)Si—CH₂—CMe₂-CH₂—S—Sn(Bu)₂-S—CH₂—CMe₂-CH₂—Si(OEt)₂(Me), (PrO)₂(Me)Si—CH₂—CMe₂-CH₂—S—Sn(Me)₂-S—CH₂—CMe₂-CH₂—Si(OPr)₂(Me), (PrO)₂(Me)Si—CH₂—CMe₂-CH₂—S—Sn(Et)₂-S—CH₂—CMe₂-CH₂—Si(OPr)₂(Me), (PrO)₂(Me)Si—CH₂—CMe₂-CH₂—S—Sn(Bu)₂-S—CH₂—CMe₂-CH₂—Si(OPr)₂(Me), (MeO)₂(Me)Si—CH₂—C(H)Me-CH₂—S—Sn(Me)₂-S—CH₂—C(H)Me-CH₂—Si(OMe)₂(Me), (MeO)₂(Me)Si—CH₂—C(H)Me-CH₂—S—Sn(Et)₂-S—CH₂—C(H)Me-CH₂—Si(OMe)₂(Me), (MeO)₂(Me)Si—CH₂—C(H)Me-CH₂—S—Sn(Bu)₂-S—CH₂—C(H)Me-CH₂—Si(OMe)₂(Me), (EtO)₂(Me)Si—CH₂—C(H)Me-CH₂—S—Sn(Me)₂-S—CH₂—C(H)Me-CH₂—Si(OEt)₂(Me), (EtO)₂(Me)Si—CH₂—C(H)Me-CH₂—S—Sn(Et)₂-S—CH₂—C(H)Me-CH₂—Si(OEt)₂(Me), (EtO)₂(Me)Si—CH₂—C(H)Me-CH₂—S—Sn(Bu)₂-S—CH₂—C(H)Me-CH₂—Si(OEt)₂(Me), (PrO)₂(Me)Si—CH₂—C(H)Me-CH₂—S—Sn(Me)₂-S—CH₂—C(H)Me-CH₂—Si(OPr)₂(Me), (PrO)₂(Me)Si—CH₂—C(H)Me-CH₂—S—Sn(Et)₂-S—CH₂—C(H)Me-CH₂—Si(OPr)₂(Me), (PrO)₂(Me)Si—CH₂—C(H)Me-CH₂—S—Sn(Bu)₂-S—CH₂—C(H)Me-CH₂—Si(OPr)₂(Me).

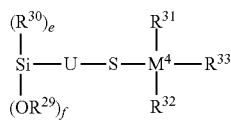

Formula 9

In Formula 9, $M^4$ is a silicon atom or a tin atom;

U is at least divalent and is selected from ($C_6$-$C_{18}$) aryl, ($C_7$-$C_{18}$) alkylaryl and ($C_1$-$C_{18}$) alkyl, wherein each group is optionally substituted with one or more groups selected from di($C_1$-$C_7$ hydrocarbyl)amino, bis(tri($C_1$-$C_{12}$ alkyl)silyl)amino, tris($C_1$-$C_7$ hydrocarbyl)silyl, ($C_7$-$C_{18}$) alkylaryl and ($C_6$-$C_{18}$) aryl;

$R^{29}$ is independently selected from ($C_1$-$C_4$) alkyl, ($C_6$-$C_{18}$) aryl and ($C_7$-$C_{18}$) alkylaryl;

$R^{31}$, $R^{32}$ and $R^{33}$ are each independently selected from ($C_1$-$C_{18}$) alkyl, ($C_1$-$C_{18}$) alkoxy, ($C_6$-$C_{18}$) aryl and ($C_7$-$C_{18}$) alkylaryl;

$R^{30}$ is independently selected from ($C_1$-$C_{18}$) alkyl, ($C_1$-$C_{18}$) alkoxy, ($C_6$-$C_{18}$) aryl, ($C_7$-$C_{18}$) alkylaryl and $R^{34}$—($C_2H_4O)_g$—O—, wherein $R^{34}$ is selected from ($C_5$-$C_{23}$) alkyl, ($C_5$-$C_{23}$) alkoxy, ($C_6$-$C_{18}$) aryl and ($C_7$-$C_{25}$) alkylaryl and g is selected from 4, 5 and 6;

e is selected from 0, 1 and 2; f is selected from 1, 2 and 3; and e+f=3.

Specific preferred species of the chain end modifying agent of Formula 9 include the following compounds and their corresponding Lewis base adducts: (MeO)₃Si—(CH₂)₃—S—SiMe₃, (EtO)₃Si—(CH₂)₃—S—SiMe₃, (PrO)₃Si—(CH₂)₃—S—SiMe₃, (BuO)₃Si—(CH₂)₃—S—SiMe₃, (MeO)₃Si—(CH₂)₂—S—SiMe₃, (EtO)₃Si—(CH₂)₂—S—SiMe₃, (PrO)₃Si(CH₂)₂—S—SiMe₃, (BuO)₃Si—(CH₂)₂—S—SiMe₃, (MeO)₃Si—CH₂—S—SiMe₃, (EtO)₃Si—CH₂—S—SiMe₃, (PrO)₃Si—CH₂—S—SiMe₃, (BuO)₃Si—CH₂—S—SiMe₃, (MeO)₃Si—CH₂—CMe₂-CH₂—S—SiMe₃, (EtO)₃Si—CH₂—CMe₂-CH₂—S—SiMe₃, (PrO)₃Si—CH₂—CMe₂-CH₂—S—SiMe₃, (BuO)₃Si—CH₂—CMe₂-CH₂—S—SiMe₃, ((MeO)₃Si—CH₂—C(H)Me-CH₂—S—SiMe₃, (EtO)₃Si—CH₂—C(H)Me-CH₂—S—SiMe₃, (PrO)₃Si—CH₂—C(H)Me-CH₂—S—SiMe₃, (BuO)₃Si—CH₂—C(H)Me-CH₂—S—SiMe₃, (MeO)₂(Me)Si—(CH₂)₃—S—SiMe₃, (EtO)₂(Me)Si—(CH₂)₃—S—SiMe₃, (PrO)₂(Me)Si—(CH₂)₃—S—SiMe₃, (BuO)₂(Me)Si—(CH₂)₃—S—SiMe₃, (MeO)₂(Me)Si—(CH₂)₂—S—SiMe₃, (EtO)₂(Me)Si—(CH₂)₂—S—SiMe₃, (PrO)₂(Me)Si—(CH₂)₂—S—SiMe₃, (BuO)₂(Me)Si—(CH₂)₂—S—SiMe₃, (MeO)₂(Me)Si—CH₂—S—SiMe₃, (EtO)₂(Me)Si—CH₂—S—SiMe₃, (PrO)₂(Me)Si—CH₂—S—SiMe₃, (BuO)₂(Me)Si—CH₂—S—SiMe₃, (MeO)₂(Me)Si—CH₂—CMe₂-CH₂—S—SiMe₃, (EtO)₂(Me)Si—CH₂—CMe₂-CH₂—S—SiMe₃, (PrO)₂(Me)Si—CH₂—CMe₂-CH₂—S—SiMe₃, (BuO)₂(Me)Si—CH₂—CMe₂-CH₂—S—SiMe₃, ((MeO)₂(Me)Si—CH₂—C(H)Me-CH₂—S—SiMe₃, (EtO)₂(Me)Si—CH₂—C(H)Me-CH₂—S—SiMe₃, (PrO)₂(Me)Si—CH₂—C(H)Me-CH₂—S—SiMe₃, (BuO)₂(Me)Si—CH₂—C(H)Me-CH₂—S—SiMe₃, (MeO)(Me)₂Si—(CH₂)₃—S—SiMe₃, (EtO)(Me)₂Si—(CH₂)₃—S—SiMe₃, (PrO)(Me)₂Si—(CH₂)₃—S—SiMe₃, (BuO)(Me)₂Si—(CH₂)₃—S—SiMe₃, (MeO)(Me)₂Si—(CH₂)₂—S—SiMe₃, (EtO)(Me)₂Si—(CH₂)₂—S—SiMe₃, (PrO)(Me)₂Si—(CH₂)₂—S—SiMe₃, (BuO)(Me)₂Si(CH₂)₂—S—SiMe₃, (MeO)(Me)₂Si—CH₂—S—SiMe₃, (EtO)(ME)₂Si—CH₂—S—SiMe₃, (PrO)(Me)₂Si—CH₂—S—SiMe₃, (BuO)(Me)₂Si—CH₂—S—SiMe₃, (MeO)(Me)₂Si—CH₂—CMe₂-CH₂—S—SiMe₃, (EtO)(Me)₂Si—CH₂—CMe₂-CH₂—S—SiMe₃, (PrO)(Me)₂Si—CH₂—CMe₂-CH₂—S—SiMe₃, (BuO)(Me)₂Si—CH₂—CMe₂-CH₂—S—SiMe₃, ((MeO)(Me)₂Si—CH₂—C(H)Me-CH₂—S—SiMe₃, (EtO)(Me)₂Si—CH₂—C(H)Me-CH₂—S—SiMe₃, (PrO)(Me)₂Si—CH₂—C(H)Me-CH₂—S—SiMe₃, (BuO)(Me)₂Si—CH₂—C(H)Me-CH₂—S—SiMe₃, (MeO)₃Si—(CH₂)₃—S—SiEt₃, (EtO)₃Si—(CH₂)₃—S—SiEt₃, (PrO)₃Si—(CH₂)₃—S—SiEt₃, (BuO)₃Si(CH₂)₃—S—SiEt₃, (MeO)₃Si(CH₂)₂—S—SiEt₃, (EtO)₃Si—(CH₂)₂—S—SiEt₃, (PrO)₃Si—(CH₂)₂—S—SiEt₃, (BuO)Si—(CH₂)₂S—SiEt₃, (MeO)₃Si—CH₂—S—SiEt₃, (EtO)₃Si—CH₂—S—SiEt₃, (PrO)₃Si—CH₂—S—SiEt₃, (BuO)₃Si—CH₂—S—SiEt₃, (MeO)₃Si—CH₂—CMe₂-CH₂—S—SiEt₃, (EtO)₃Si—CH₂—CMe₂-CH₂—S—SiEt₃, (PrO)₃Si—CH₂—CMe₂-CH₂—S—SiEt₃, (BuO)₃Si—CH₂—CMe₂-CH₂—S—SiEt₃, ((MeO)₃Si—CH₂—C(H)Me-CH₂—S—SiEt₃, (EtO)₃Si—CH₂—C(H)Me-CH₂—S—SiEt₃, (PrO)₃Si—CH₂—C(H)Me-CH₂—S—SiEt₃, (BuO)₃Si—CH₂—C(H)Me-CH₂—S—SiEt₃, (MeO)₂(Me)Si—(CH₂)₃—S—SiEt₃, (EtO)₂(Me)Si—(CH₂)₃—S—SiEt₃, (PrO)₂(Me)Si—(CH₂)₃—S—SiEt₃, (BuO)₂(Me)Si—(CH₂)₃—S—SiEt₃, (MeO)₂(Me)Si—(CH₂)₂—S—SiEt₃, (EtO)₂(Me)Si—(CH₂)₂—S—SiEt₃, (PrO)₂(Me)Si—(CH₂)₂—S—SiEt₃, (BuO)₂(Me)Si—(CH₂)₂—S—SiEt₃, (MeO)₂(Me)Si—CH₂—S—SiEt₃, (EtO)₂(Me)Si—CH₂—S—SiEt₃, (PrO)₂(Me)Si—CH₂—S—SiEt₃, (BuO)₂(Me)Si—CH₂—S—SiEt₃, (MeO)₂(Me)Si—CH₂—CMe₂-CH₂—S—SiEt₃, (EtO)₂(Me)Si—CH₂—CMe₂-CH₂—S—SiEt₃, (PrO)₂(Me)Si—CH₂—CMe₂-CH₂—S—SiEt₃, (BuO)₂(Me)Si—CH₂—CMe₂-CH₂—S—SiEt₃, ((MeO)(Me)₂Si—CH₂—C(F)Me-CH₂—S—SiEt₃, (EtO)(Me)₂Si—CH₂—C(H)Me-CH₂—S—SiEt₃, (PrO)(Me)₂Si—CH₂—C(H)Me-CH₂—S—SiEt₃ and (BuO)(Me)₂Si—CH₂—C(H)Me-CH₂—S—SiEt₃.

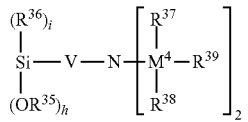

Formula 10

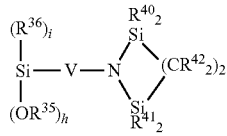

Formula 11

In Formulas 10 and 11, V is at least divalent and is selected from $(C_6-C_{18})$ aryl, $(C_7-C_{18})$ alkylaryl and $(C_1-C_{18})$ alkyl, wherein each group is optionally substituted with one or more groups selected from di($C_1-C_7$ hydrocarbyl)amino, bis(tri($C_1-C_{12}$ alkyl)silyl)amino, tris($C_1-C_7$ hydrocarbyl)silyl, $(C_7-C_{18})$ alkylaryl and $(C_6-C_{18})$ aryl;

$R^{35}$ is independently selected from $(C_1-C_4)$ alkyl, $(C_6-C_{18})$ aryl and $(C_7-C_{18})$ alkylaryl;

$R^{37}$, $R^{38}$, $R^{39}$, $R^{40}$, $R^{41}$ and $R^{42}$ are each independently selected from $(C_1-C_{18})$ alkyl, $(C_1-C_{18})$ alkoxy, $(C_6-C_{18})$ aryl and $(C_7-C_{18})$ alkylaryl;

$R^{36}$ is independently selected from $(C_1-C_{18})$ alkyl, $(C_1-C_{18})$ alkoxy, $(C_6-C_{18})$ aryl, $(C_7-C_{18})$ alkylaryl and $R^{43}$—$(C_2H_4O)_j$—O—, wherein $R^{43}$ is selected from $(C_5-C_{23})$ alkyl, $(C_5-C_{23})$ alkoxy, $(C_6-C_{18})$ aryl and $(C_7-C_{25})$ alkylaryl; and j is selected from the 4, 5 and 6;

i is selected from 0, 1 and 2; h is selected from 1, 2 and 3; and i+h=3.

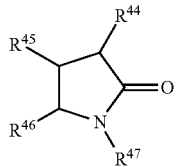

Formula 12

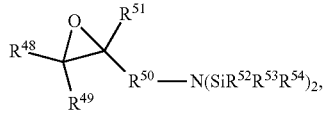

Formula 13

In Formulas 12 and 13, $R^{44}$, $R^{45}$, $R^{46}$, $R^{47}$, $R^{48}$, $R^{49}$, $R^{51}$, $R^{52}$, $R^{53}$ and $R^{54}$ are each independently selected from hydrogen, $(C_1\text{-}C_{16})$ alkyl, $(C_6\text{-}C_{16})$ aryl and $(C_7\text{-}C_{16})$ alkylaryl; and $R^{50}$ is at least divalent and is selected from $(C_6\text{-}C_{18})$ aryl, $(C_7\text{-}C_{18})$ alkylaryl and $(C_1\text{-}C_{18})$ alkyl, wherein each group is optionally substituted with one or more groups selected from di($C_1\text{-}C_7$ hydrocarbyl)amino, bis(tri($C_1\text{-}C_{12}$ alkyl)silyl)amino, tris($C_1\text{-}C_7$ hydrocarbyl)silyl, $(C_7\text{-}C_{18})$ alkylaryl and $(C_6\text{-}C_{18})$ aryl.

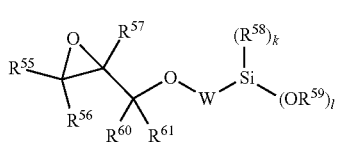

Formula 14

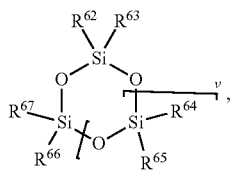

Formula 15

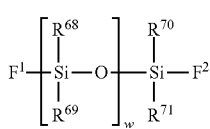

Formula 16

In Formulas 14, 15 and 16, $R^{55}$, $R^{56}$, $R^{57}$, $R^{58}$, $R^{60}$, $R^{61}$, $R^{62}$, $R^{63}$, $R^{64}$, $R^{65}$, $R^{66}$, $R^{67}$, $R^{68}$, $R^{69}$, $R^{70}$ and $R^{71}$ are each independently selected from hydrogen, $(C_1\text{-}C_{16})$ alkyl, $(C_6\text{-}C_{16})$ aryl and $(C_7\text{-}C_{16})$ alkylaryl;

$R^{59}$ is selected from $(C_1\text{-}C_4)$ alkyl, $(C_6\text{-}C_{18})$ aryl and $(C_7\text{-}C_{18})$ alkylaryl:

W is at least divalent and is selected from $(C_6\text{-}C_{18})$ aryl, $(C_7\text{-}C_{18})$ alkylaryl and $(C_1\text{-}C_{18})$ alkyl, wherein each group is optionally substituted with one or more groups selected from di($C_1\text{-}C_7$ hydrocarbyl)amino, bis(tri($C_1\text{-}C_{12}$ alkyl)silyl)amino, tris($C_1\text{-}C_7$ hydrocarbyl)silyl, $(C_7\text{-}C_{18})$ alkylaryl and $(C_6\text{-}C_{18})$ aryl;

k is selected from 0, 1 and 2; l is selected from 1, 2 and 3; k+l=3; and v is selected from 1 to 20;

$F^1$ and $F^2$ are independently selected from hydrogen, hydroxy, chlorine, bromine, iodine, $-SiR^{52}R^{53}R^{54}$, wherein $R^{52}$, $R^{53}$, $R^{54}$ are the same or different and are as defined for Formulas 12 and 13, vinyl, $(C_6\text{-}C_{16})$ aryl, $(C_7\text{-}C_{16})$ alkylaryl and $(C_1\text{-}C_{16})$ alkyl, wherein each hydrocarbyl group is optionally substituted with one or more groups selected from hydroxyl, di($C_1\text{-}C_7$ hydrocarbyl)amino, bis(tri($C_1\text{-}C_{12}$ alkyl)silyl)amino and an epoxy group.

If more than one chain end modifying agent is used for the purpose of chain end modification, the chain end modifying agents can be added one after another to a solution of the living anionic polymer, or they can be mixed together before adding the resulting mixture to a solution of the living anionic polymer.

The chain end modifying agents may be added intermittently (or at regular or irregular intervals) or continuously during the polymerization, but are preferably added at a conversion rate of the polymerization of more than 80 percent and more preferably at a conversion rate of more than 90 percent. Preferably, a substantial amount of the polymer chain ends is not terminated prior to the reaction with the chain end modifying agent; that is, living polymer chain ends are present and are capable of reacting with the modifying agent. The chain end modification reaction may occur before, after or during the addition of any coupling agent. Preferably the chain end modification reaction is completed after the addition of any coupling agent. See, for example, WO 2009/148932, incorporated herein by reference.

In one embodiment, more than 20 percent, preferably more than 35 percent and even more preferably more than 50 percent of the polymer chains, as determined by GPC, formed in the course of the polymerization process, are linked with a chain end modifying agent in the process of polymer chain end modification.

In one embodiment, more than 50 percent, preferably more than 60 percent and more preferably more than 75 percent, as determined by GPC, of the living polymer of the invention (still remaining after the coupling reaction) react with a chain end modifying agent.

Process of Chain End Modification

The polymerization initiator of the invention reacts with monomers to form an "omega,omega'-carbanionic" living polymer molecule of the invention. The reaction of at least one living polymer molecule with at least one equivalent of chain end modifying agent results in a modified polymer molecule. In case both polymer chain ends of a linear polymer molecule (comprising two omega,omega carbanionic polymer chain end positions) are modified with a chain end modifying agent, an omega,omega'-dimodified linear polymer molecule is formed. Thus, each carbanionic polymer chain end reacts with one equivalent of chain end modifying agent. If coupling agents (as described herein) are reacted with one or both of the carbanionic polymer chain end positions, a branched modified polymer molecule is formed. This can also be formed when monomers capable of reacting with more than one growing polymer chain, such as divinylbenzene, are added to the polymerization mixture at any time in the polymerization.

The chain end modifying agent may be added directly to the polymer solution without dilution; however, it may be beneficial to add the modifying agent in dissolved form, such as in an inert solvent (e.g., cyclohexane). The amount of chain end modifying agent to be added to the polymerization may vary depending on the monomer species, coupling agent, chain end modifying agent, reaction conditions and desired polymer properties, but is generally from 0.1 to 5 mol-equivalent, preferably from 0.2 to 4.0 mol-equivalent and most preferably from 0.5 to 3.0 mol-equivalent per mol equivalent of alkali metal in the initiator compound. The polymer chain end modification reaction may be carried out at a temperature ranging from 0° C. to 150° C., preferably from 15° C. to 120° C. and even more preferably from 40° C. to 100° C. There is no limitation as regards the duration of the chain end modification reaction. However, with respect to an economical polymerization process, for example, in the case of a batch polymerization process, the chain end modification reaction is usually stopped at about 5 to 60 minutes after the addition of the modifying agent.

A method for making the modified polymer of the invention comprises at least the following steps A through C.

Step A: reacting the polymerization initiator of the invention as represented by Formula 1, 5, 6, 17, 18 or 19 (each as defined herein), preferably by Formula 6, 17, 18 or 19, with one or more polymerizable monomers selected from conjugated olefins and aromatic vinyl compounds, preferably selected from butadiene, styrene, isoprene, alpha methylstyrene and combinations thereof, in a polymerization solvent. Suitable polymerization solvents include non-polar aliphatic and non-polar aromatic solvents, preferably hexane, heptane, butane, pentane, isopar, cyclohexane, toluene and benzene.

Step B: optionally reacting part of the polymer molecules of the reaction product of step A with at least one type of coupling agent selected from $SnCl_4$, $(R_1)_3SnCl$, $(R_1)_2SnCl_2$, R$_1$SnCl$_3$, SiCl$_4$, (R$_1$)$_3$SiCl, (R$_1$)$_2$SiCl$_2$, R$_1$SiCl$_3$, Cl$_3$Si—SiCl$_3$, Cl$_3$Si—O—SiCl$_3$, Cl$_3$Sn—SnCl$_3$, Cl$_3$Sn—O—SnCl$_3$, Sn(OMe)$_4$, Si(OMe)$_4$, Sn(OEt)$_4$ and Si(OEt)$_4$, wherein R$_1$ is a hydrocarbyl group, preferably an alkyl group.

Step C: reacting the reaction product of step A or B with at least one chain end modifying agent, preferably selected from Formulas 8, 9, 10, 11, 12, 13, 14, 15 and 16 (as described herein), to form the chain end modified polymer.

Randomizer Agents

In addition to the Lewis bases preferably used for the formation of the polymerization diinitiator compounds of the invention, additional Lewis bases may optionally be added to the polymerization mixture to adjust the microstructure (such as content of vinyl bonds) of the conjugated diolefin portion of a diolefin-type homo-, co- or terpolymer or to adjust the composition distribution of the aromatic vinyl compound in the conjugated diene monomer-containing co- or terpolymer, thus serving as a randomizer component. The additional Lewis bases are, for example, ether compounds such as diethyl ether, di-n-butyl ether, ethylene glycol diethyl ether, ethylene glycol dibutyl ether, diethylene glycol dimethyl ether, propylene glycol dimethyl ether, propylene glycol diethyl ether, propylene glycol dibutyl ether, alkyltetrahydrofuryl ethers such as methyltetrahydrofuryl ether, ethyltetrahydrofuryl ether, propyltetrahydrofuryl ether, butyltetrahydrofuryl ether, hexyltetrahydrofuryl ether, octyltetrahydrofuryl ether, tetrahydrofuran, 2,2-bis(tetrahydrofurfuryl)propane, bis(tetrahydrofurfuryl)formal, methyl ether of tetrahydrofurfuryl alcohol, ethyl ether of tetrahydrofurfuryl alcohol, butyl ether of tetrahydrofurfuryl alcohol, α-methoxytetrahydrofuran, dimethoxybenzene and dimethoxyethane, and tertiary amine compounds such as butyl ether of triethylamine, pyridine, N,N,N',N'-tetramethyl ethylenediamine, dipiperidinoethane, methyl ether of N,N-diethylethanolamine, ethyl ether of N,N-diethylethanolamine and N,N-diethylethanolamine.

Coupling Agents

Polymerization initiator compounds of the invention may optionally be reacted with one or more coupling agents to form branched polymers.

Coupling agents include tin tetrachloride, tin tetrabromide, tin tetrafluoride, tin tetraiodide, silicon tetrachloride, silicon tetrabromide, silicon tetrafluoride, silicon tetraiodide, alkyl tin and alkyl silicon trihalides or dialkyl tin and dialkyl silicon dihalides. Polymers coupled with tin or silicon tetrahalides have a maximum of four arms, polymers coupled with alkyl tin and alkyl silicon trihalides have a maximum of three arms, and polymers coupled with dialkyl tin and dialkyl silicon dihalides have a maximum of two arms. Hexahalo disilanes or hexahalo disiloxanes can also be used as coupling agents, resulting in polymers with a maximum of six arms. Useful tin and silicon halides coupling agents include: SnCl$_4$, (R$_1$)$_3$SnCl, (R$_1$)$_2$SnCl$_2$, R$_1$SnCl$_3$, SiCl$_4$, R$_1$SiCl$_3$, (R$_1$)$_2$SiCl$_2$, (R$_1$)$_3$SiCl, Cl$_3$Si—SiCl$_3$, Cl$_3$Si—O—SiCl$_3$, Cl$_3$Sn—SnCl$_3$ and Cl$_3$Sn—O—SnCl$_3$ wherein R$_1$ is a hydrocarbyl group, preferably an alkyl group. Examples of tin and silicon alkoxides coupling agents further include: Sn(OMe)$_4$, Si(OMe)$_4$, Sn(OEt)$_4$ and Si(OEt)$_4$. The most preferred coupling agents are: SnCl$_4$, SiCl$_4$, Sn(OMe)$_4$ and Si(OMe)$_4$.

The coupling agents may be added intermittently (or at regular or irregular intervals) or continuously during the polymerization, but are preferably added at a conversion rate of the polymerization of more than 80 percent and more preferably at a conversion rate of more than 90 percent. The coupling agent will typically be added only after a high degree of conversion has already been achieved.

For example, a coupling agent can be continuously added during the polymerization, in cases where asymmetrical coupling is desired. Such continuous addition is normally carried out in a reaction zone separate from the zone where the bulk of the polymerization is taking place. The coupling agent can be added in a hydrocarbon solution, for example, in cyclohexane, to the polymerization admixture, with suitable mixing for distribution and reaction. Typically, from 0.01 to 2.0 mol, preferably from 0.02 to 1.5 mol and more preferably from 0.04 to 0.6 mol of the coupling agent is used for every 4.0 moles of living anionic polymer chain ends.

Preferably, a substantial amount of the polymer chain ends is not terminated prior to the reaction with the coupling agent; that is, living polymer chain ends are present and capable of reacting with the coupling agent in a polymer chain coupling reaction. The coupling reaction occurs before, after or during the addition of any chain end modifying agent. The coupling reaction is preferably completed prior to the addition of the chain end modifying agent. In some embodiments, between 5 and 20 percent of the living polymer chain ends, as determined by GPC, have reacted with coupling agent prior to the addition of the chain end modifying agent. In other embodiments, between 20 and 35 percent of the living polymer chain ends have reacted with coupling agent prior to the addition of the chain end modifying agent. In yet another embodiment, between 35 and 50 percent of the living polymer chain ends have reacted with coupling agent prior to the addition of the chain end modifying agent.

A combination of different coupling agents such as Bu$_2$SnCl$_2$ and SnCl$_4$; Me$_2$SiCl$_2$ and Si(OMe)$_4$; Me$_2$SiCl$_2$ and SiCl$_4$; SnCl$_4$ and Si(OMe)$_4$; SnCl$_4$ and SiCl$_4$, can also be used to couple polymer chains. It is particularly desirable to use a combination of tin and silicon coupling agents in tire tread compounds that contain both silica and carbon black. In such case, the molar ratio of the tin to the silicon compound will normally be within the range of from 20:80 to 95:5; more typically from 40:60 to 90:10 and preferably from 60:40 to 85:15. Most typically, an amount of from about 0.001 to 4.5 mmol of coupling agent is employed per 100 grams of polymer. It is normally preferred to utilize from about 0.05 to about 0.5 mmol of coupling agent per 100 grams of polymer to obtain the desired Mooney viscosity and to enable subsequent chain-end functionalization of the remaining living polymer fraction. Larger quantities tend to produce polymers containing terminally reactive groups or insufficient coupling and only enable an insufficient chain end modification.

The polymer coupling reaction may be carried out in a temperature range of from 0° C. to 150° C., preferably from 15° C. to 120° C. and even more preferably from 40° C. to 100° C. There is no limitation for the duration of the coupling reaction. However, with respect to an economical polymerization process, for example in the case of a batch polymerization process, the coupling reaction is usually stopped at about 5 to 60 minutes after the addition of the coupling agent.

Method of Making Polymer

The method of making the polymer according to the fourth aspect of the invention comprises the steps of reacting
i) a polymerization initiator of Formula 1 or a Lewis base adduct thereof and
ii) at least one type of polymerizable monomers selected from conjugated olefins and aromatic vinyl compounds.

In specific embodiments of the method of making the polymer, the polymerization initiator is one or more selected from the embodiments and preferred embodiments as defined herein in the description of the polymerization initiator.

In one embodiment of the method of making the polymer of the invention, referred to as "Embodiment 5", the polymerization initiator is a compound of Formula 5 or a Lewis base adduct thereof, as defined herein as "Embodiment 1" in the description of the polymerization initiator and including embodiments and preferred embodiments thereof.

In another embodiment of the method of making the polymer, the polymerization initiator is a compound of Formula 6 or a Lewis base adduct thereof, as defined herein as "Embodiment 2" in the description of the polymerization initiator and including embodiments and preferred embodiments thereof.

In yet another embodiment of the method of making the polymer, the polymerization initiator is selected from a compound of Formula 17, 18 and 19 or a Lewis base adduct thereof, as defined herein in the description of the polymerization initiator and including embodiments and preferred embodiments thereof.

In a preferred embodiment, the method of making the modified polymer comprises the steps of
firstly reacting a polymerization initiator of Formula 1, including Formulas 5, 6, 17, 18 and 19 and embodiments thereof, or a Lewis base adduct thereof with at least one type of polymerizable monomers selected from conjugated olefins and aromatic vinyl compounds, thus forming an omega,omega'-dianionic living polymer, and
further reacting the omega,omega'-dianionic living polymer with a chain-end modifier compound as described below, thus forming the modified polymer as an omega, omega'-modified polymer which is modified at least two polymer chain ends.

The method of making the polymer is conventionally carried out in a polymerization solvent as a solution polymerization, wherein the polymer formed is substantially soluble in the reaction mixture, or as a suspension/slurry polymerization, wherein the polymer formed is substantially insoluble in the reaction medium. Suitable polymerization solvents include non-polar aliphatic and non-polar aromatic solvents, preferably hexane, heptane, butane, pentane, isopar, cyclohexane, toluene and benzene. The solution polymerization normally takes place at lower pressures, preferably below 10 MPa, preferably in a temperature range of from 0 to 120° C. The polymerization is generally conducted under batch, continuous or semi-continuous polymerization conditions.

Generally applicable information about the polymerization technologies including polymerization initiator compounds; polar coordinator compounds and accelerators, each to increase the reactivity of the initiator, to randomly arrange aromatic vinyl compounds, to randomly arrange 1,2-polybutadiene or 1,2-polyisoprene or 3,4-polyisoprene units introduced in the polymer; the amounts of each compound; monomer(s); and suitable process conditions are described in WO 2009/148932, fully incorporated herein by reference.

The method of making the polymer in accordance with the invention will conventionally provide the polymer of the invention, including modified polymer, in the reaction solvent, optionally together with additional (non-inventive) non-modified linear, branched and coupled polymer molecules and additional (non-inventive) modified polymer molecules, with all polymer molecules being made from living polymer chains formed in the polymer polymerization process. The modified polymer molecules of the invention may be formed by the modification of living polymers using modifying agents as described herein. The additional (non-inventive) non-modified and additional (non-inventive) modified polymer molecules are not linked to an initiator compound of the invention and may be the result of using (non-inventive) initiator compounds containing a polar group, living polymer chain-terminating or chain-end modification reactions, chain transfer reactions or living polymer chain coupling reactions, the latter optionally being performed through the use of one or more coupling agents as described herein. The "additional non-modified polymer molecules" or "additional modified polymer molecules" constitute components which are formed as a result of the polymerization process and which remain after solvent removal from the polymerization process. The polymer or modified polymer of the invention typically constitutes at least 10% by weight of the total polymer produced in the method of the invention, preferably at least 40% by weight, more preferably at least 60% by weight and most preferably at least 80% by weight. The additional modified or non-modified polymer, in contrast, usually constitutes 1% by weight or more of the total polymer produced in the method of the invention, typically 5% by weight or more and even more typically 10% by weight or more.

Polymer Compositions

The first polymer composition according to the fifth aspect of the invention comprises the polymer of the invention, including modified polymer, and one or more further components selected from (i) components which are added to or formed as a result of the polymerization process used for making the polymer and (ii) components which remain after solvent removal from the polymerization process. Generally, the first polymer composition is the solvent-free result of the method of making the polymer, further comprising components selected from oils (extender oils), stabilizers and further (non-inventive) polymers. Suitable oils are as defined herein. The further polymers can be made separately, for example in a different polymerization reactor, in solution and can be added to the reactor prior to completion of the polymer manufacturing process for the polymer.

The first polymer composition of the invention, as obtained after removal of solvent and process water from the polymerization process, preferably has a Mooney viscosity (ML 1+4, 100° C., as measured in accordance with ASTM D 1646 (2004) using a Monsanto MV2000 instrument) of up to 150, preferably from 20 to 120 and more preferably from 30 to 100. If the Mooney viscosity of the polymer composition is more than 150, the processability, as reflected by filler incorporation and heat build-up in the internal mixer, banding on the roll mill, extrusion rate, extrudate die swell, smoothness, etc., is likely to be negatively affected because the compounding machinery used by the tire manufacturer is not designed to handle such high Mooney rubber grades, and the cost of processing increases. In some cases a Mooney viscosity of less than 20 may not be preferred due to increased tack and cold flow of the uncrosslinked polymer, resulting in difficult handling, poor green strength and poor dimensional stability during storage. In other cases, when the polymer composition is used as a softener, compatibilizer or processing aid in polymer formulations, a Mooney viscosity of less than 20 may be preferred.

The preferred molecular weight distribution of the polymer composition as obtained after solvent removal from the polymerization process, reflected by the ratio of weight average molecular weight to number average molecular weight ($M_w/M_n$), ranges from 1.0 to 10.0, preferably from 1.1 to 8.0 and more preferably from 1.2 to 4.5.

In the first composition, the polymer present is preferably composed of at least 15% by weight of the polymer as obtained in the polymerization reaction, more preferably at least 30% by weight and even more preferably at least 45% by weight. The remaining amount of polymer is composed of the further polymers mentioned above. Examples of suitable polymers are identified in WO 2009/148932 and preferably include styrene-butadiene copolymer, natural rubbers, polyisoprene and polybutadiene. It is desirable that such further polymers have a Mooney viscosity (ML 1+4, 100° C. as measured in accordance with ASTM D 1646 (2004)) in the range of from 20 to 150, preferably from 30 to 100.

The second polymer composition according to the sixth aspect of the invention comprises the polymer of the invention, including modified polymer, and one or more fillers. The second polymer composition is typically the result of a mechanical mixing process involving the polymer of the invention and one or more fillers. It typically includes components which are added to and mechanically mixed with the polymer or first polymer composition.

The first and second polymer compositions may optionally further comprise a least one vulcanizing agent as defined further below.

The second polymer composition comprising filler can be prepared by kneading the first polymer composition, optionally comprising one or more components selected from oils, stabilizers and further polymers, and one or more fillers in a kneader at 140 to 180° C.

Alternatively, the second polymer composition can be prepared by kneading the first polymer composition and one or more fillers in a kneader at 140 to 180° C. to form a "first stage" second composition. The formation of the "first stage" second composition may involve one or more mixing steps, preferably 2 to 7 mixing steps. After cooling, vulcanizing agents such as sulfur, vulcanizing accelerators, optionally zinc oxide and the like are added to the "first stage" second composition, and the resulting "second stage" second composition is blended using a Brabender mixer, Banbury mixer or open roll mill to form the desired shape.

Oils

One or more oils may be used in combination with the uncrosslinked polymer to reduce viscosity or Mooney values or to improve processability of the first polymer composition and various performance properties of the (vulcanized) second polymer compositions.

Oils can be added to the polymer prior to the end of the polymer preparation process and as a separate component of the first or second polymer composition preparation process in accordance with the present teachings. For representative examples and classification of oils see WO 2009/148932 and US 2005/0159513, each of which is incorporated herein by reference in its entirety.

Representative oils include MES (Mild Extraction Solvate), RAE (Residual Aromatic Extract, including T-RAE (Treated Residual Aromatic Extract) and S-RAE), DAE (Distillate Aromatic Extract, including TDAE (Treated Distillated Aromatic Extract)) and NAP (light and heavy naphthenic oils, including Nytex 4700, Nytex 8450, Nytex 5450, Nytex 832, Tufflo 2000 and Tufflo 1200). In addition, native oils, including vegetable oils, can be used as extender oils. Representative oils also include functionalized variations of these oils, particularly epoxidized or hydroxylated oils. The oils may contain varying concentrations of polycyclic aromatic compounds, paraffinics, naphthenics and aromatics and may have different glass transition temperatures.

Processing Aids

Processing aids can optionally be added to the first polymer composition. They are usually added for reducing the viscosity. As a result, the mixing period is decreased and/or the number of mixing steps is reduced and, consequently, less energy is consumed and/or a higher throughput in the course of the rubber compound extrusion process is achieved. Representative processing aids are described in *Rubber Handbook, SGT The Swedish Institution of Rubber Technology* 2000 and in Werner Kleemann, Kurt Weber, *Elastverarbeitung-Kennwerte und Berechnungsmethoden*, Deutscher Verlag für Grundstoffindustrie (Leipzig, 1990), each of which is incorporated herein by reference in its entirety. Examples of representative processing aids include in particular:

(A) fatty acids, including oleic acid, priolene, pristerene and stearic acid;
(B) fatty acid salts, including Aktiplast GT, PP, ST, T, T-60, 8, F; Deoflow S; Kettlitz Dispergator FL, FL Plus; Dispergum 18, C, E, K, L, N, T, R; Polyplastol 6, 15, 19, 21, 23; Struktol A50P, A60, EF44, EF66, EM16, EM50, WA48, WB16, WB42, WS180, WS280 and ZEHDL;
(C) dispersing agents, including Aflux 12, 16, 42, 54, 25; Deoflow A, D; Deogum 80; Deosol H; Kettlitz Dispergator DS, KB, OX; Kettlitz-Mediaplast 40, 50, Pertac/GR; Kettlitz-Dispergator SI; Struktol FL and WB 212; and
(D) dispersing agents for highly active white fillers, including Struktol 33 and WB42.

Fillers

The second composition of the invention comprises one or more fillers, which serve as reinforcement agents. Examples of suitable fillers include carbon black (including electroconductive carbon black), carbon nanotubes (CNT) (including discrete CNT, hollow carbon fibers (HCF) and modified CNT carrying one or more functional groups, such as hydroxyl, carboxyl and carbonyl groups), graphite, graphene (including discrete graphene platelets), silica, carbon-silica dual-phase filler, clays (layered silicates, including exfoliated nanoclay and organoclay), calcium carbonate, magnesium carbonate, lignin, amorphous fillers, such as glass particle-based fillers, starch-based fillers, and combinations thereof. Further examples of suitable fillers are described in WO 2009/148932 which is fully incorporated herein by reference.

Examples of suitable carbon black include the one conventionally manufactured by a furnace method, for example having a nitrogen adsorption specific surface area of 50-200 $m^2/g$ and DBP oil absorption of 80-200 ml/100 grams, such as carbon black of the FEF, HAF, ISAF or SAF class, and electroconductive carbon black. In some embodiments, high agglomeration-type carbon black is used. Carbon black is typically used in an amount of from 2 to 100 parts by weight, or 5 to 100 parts by Weight, or 10 to 100 parts by weight, or 10 to 95 parts by weight per 100 parts by weight of the total polymer.

Examples of suitable silica fillers include wet process silica, dry process silica and synthetic silicate-type silica. Silica with a small particle diameter and high surface area exhibits a high reinforcing effect. Small diameter, high agglomeration-type silica (i.e. having a large surface area and high oil absorptivity) exhibits excellent dispersibility in the polymer composition, resulting in superior processability. An average particle diameter of silica in terms of the primary particle diameter may be from 5 to 60 nm, or 10 to 35 nm. The specific surface area of the silica particles (measured by the BET method) may be from 35 to 300 $m^2/g$. Silica is typically used in an amount of from 10 to 100 parts by weight, or 30 to 100 parts by weight, or 30 to 95 parts by weight per 100 parts by weight of the total polymer.

Silica fillers can be used in combination with other fillers, including carbon black, carbon nanotubes, carbon-silica dual-phase-filler, graphene, graphite, clay, calcium carbonate, magnesium carbonate and combinations thereof.

Carbon black and silica may be added together, in which case the total amount of carbon black and silica is from 30 to 100 parts by weight or 30 to 95 parts by weight per 100 parts by weight of the total polymer.

Carbon-silica dual-phase filler is so called silica-coated carbon black made by coating silica on the surface of carbon black and commercially available under the trademark CRX2000, CRX2002 or CRX2006 (products of Cabot Co.). Carbon-silica dual-phase filler is added in the same amounts as described above with respect to silica.

Shane Coupling Agents

In some embodiments, a silane coupling agent (used for compatibilization of polymer and fillers) is added to the composition comprising the polymer of the invention and silica, layered silicate (such as magadiite) or carbon-silica dual-phase filler. The typical amount of a silane coupling agent added is from about 1 to about 20 parts by weight and, in some embodiments, from about 5 to about 15 parts by weight for 100 parts by weight of the total amount of silica and/or carbon-silica dual-phase filler.

Silane coupling agents can be classified according to *Fritz Röthemeyer, Franz Sommer: Kautschuk Technologie*, (Carl Hanser Verlag 2006):

(A) bifunctionalized silanes, including Si230 ((EtO)$_3$Si(CH$_2$)$_3$Cl), Si225 ((EtO)$_3$SiCH=CH$_2$), A189 ((EtO)$_3$Si(CH$_2$)$_3$SH), [(EtO)$_3$Si(CH$_2$)$_3$S$_x$(CH$_2$)$_3$(OEt)$_3$] with x=3.75 (Si69) or 2.35 (Si75), Si264 ((EtO)$_3$Si—(CH$_2$)$_3$SCN) and Si363 ((EtO)Si((CH$_2$—CH$_2$—O)$_5$(CH$_2$)$_{12}$CH$_3$)$_2$(CH$_2$)$_3$SH)) (Evonic Industries AG), 3-octanoylthio-1-propyltriethoxysilane (NXT) and (B) monofunctional silanes, including Si203 ((EtO)$_3$—Si—C$_3$H$_7$) and Si208 ((EtO)$_3$—Si—C$_8$H$_{17}$).

Further suitable examples of silane coupling agents are given in WO 2009/148932 and include bis-(3-hydroxy-dimethylsilyl-propyl)tetrasulfide, bis-(3-hydroxy-dimethylsilyl-propyl)disulfide, bis-(2-hydroxy-dimethylsilyl-ethyl)tetrasulfide, bis-(2-hydroxy-dimethylsilyl-ethyl)disulfide, 3-hydroxy-dimethylsilyl-propyl-N,N-dimethylthiocarbamoyl tetrasulfide and 3-hydroxy-dimethylsilyl-propylbenzothiazole tetrasulfide.

Vulcanizing Agents

Any vulcanizing agent conventionally used in the manufacture of rubber products can be used in the invention, and a combination of two or more vulcanizing agents may be used.

Sulfur, sulfur-containing compounds acting as sulfur donors, sulfur accelerator systems and peroxides are the most common vulcanizing agents. Examples of sulfur-containing compounds acting as sulfur donors include dithiodimorpholine (DTDM), tetramethylthiuram disulfide (TMTD), tetraethylthiuram disulfide (TETD) and dipentamethylenethiuram tetrasulfide (DPTT). Examples of sulfur accelerators include amine derivates, guanidine derivates, aldehydeamine condensation products, thiazoles, thiuram sulfides, dithiocarbamates and thiophosphates. Examples of peroxides include di-tert.-butyl-peroxides, di-(tert.-butyl-peroxy-trimethyl-cyclohexane), di-(tert.-butyl-peroxy-iso-propyl-)benzene, dichloro-benzoylperoxide, dicumyl peroxides, tert.-butyl-cumyl-peroxide, dimethyl-di(tert.-butyl-peroxy)hexane, dimethyl-di(tert.-butyl-peroxy)hexine and butyl-di(tert.-butyl-peroxy)valerate (*Rubber Handbook, SGF, The Swedish Institution of Rubber Technology* 2000).

Further examples and additional information regarding vulcanizing agents can be found in Kirk-Othmer, *Encyclopedia of Chemical technology* 3$^{rd}$, Ed., (Wiley Interscience, N.Y. 1982), volume 20, pp. 365-468, (specifically "Vulcanizing Agents and Auxiliary Materials" pp. 390-402).

A vulcanizing accelerator of the sulfene amide-type, guanidine-type or thiuram-type can be used together with a vulcanizing agent as required. Other additives such as zinc white, vulcanization auxiliaries, aging preventives, processing adjuvants and the like may optionally be added. A vulcanizing agent is typically added to the polymer composition in an amount of from 0.5 to 10 parts by weight or, in some embodiments, 1 to 6 parts by weight per 100 parts by weight of the total polymer. Examples of vulcanizing accelerators and amount thereof added with respect to the total polymer are given in WO 2009/148932.

Sulfur accelerator systems may or may not contain zinc oxide. Zinc oxide is preferably used as a component of the sulfur accelerator system.

Vulcanized Polymer Composition

The vulcanized polymer composition according to the seventh aspect of the invention is obtained by vulcanizing the first or the second polymer composition, which comprises at least one vulcanizing agent. Since the vulcanized elastomeric polymer compositions of the invention exhibit low rolling resistance, low dynamic heat build-up and superior wet skid performance, they are well suited for use in manufacturing tires, tire treads, side walls and tire carcasses as well as other industrial products such as belts, hoses, vibration dampers and footwear components.

The vulcanized polymer composition is the result of a reactive polymer-polymer crosslink-forming process which is performed on (i) a mixture of the polymer and at least one vulcanizing agent, (ii) the first polymer composition comprising at least one vulcanizing agent, or (iii) the second polymer composition comprising at least one vulcanizing agent. Therefore, the reactive process converts an essentially uncrosslinked polymer or an essentially uncrosslinked polymer composition, particularly a first polymer composition or second polymer composition each containing at least one vulcanizing agent, into a vulcanized (or crosslinked) polymer composition.

The cross-linked (vulcanized) polymer composition of the invention exhibits reduced heat build-up, reduced rebound resilience at 0° C. and a good balance of physical properties, including one or more of the following: abrasion resistance, tensile strength, modulus and tear, while a composition comprising the uncrosslinked polymer (prior to vulcanization) maintains good processing characteristics. The composition is useful in preparing tire treads having lower rolling resistance, higher wet grip, higher ice grip and lower heat build-up, while maintaining good wear properties.

For a vulcanized polymer, the gel content is preferably greater than 50 weight percent, more preferably greater than 75 weight percent and even more preferably greater than 90 weight percent, based on the weight of the polymer. Gel content can be determined by dissolving 0.2 grams of polymer in 150 ml of toluene for 24 hours at ambient temperature, separating the insolubles, drying the insolubles and measuring the amount of insolubles.

The invention also provides an article comprising at least one component formed from a vulcanized polymer composition of the invention. The article may be a tire, a tire tread, a tire side wall, an automotive part, a footwear component, a golf ball, a belt, a gasket, a seal or a hose.

For producing vehicle tires, the following further polymers are of particular interest for use in combination with the polymer of the invention: natural rubber; low cis polybutadiene (LCBR) comprising less than 20 percent by weight of 1,2-polybutadiene, emulsion SBR (ESBR) and solution SBR (SSBR) rubbers with a glass transition temperature above −50° C.; polybutadiene rubber with a high cis-1,4-unit content (>90%), such as obtained by using catalysts based on nickel, cobalt, titanium, vanadium, gadolinium or neodymium; and polybutadiene rubber with a vinyl content of 0 to 75%; and combinations thereof: polybutadiene rubber with a high trans-1,4-unit content (>75%) or SBR containing, for example, between 5 and 45 wt % styrene and having a high trans-1,4-polybutadiene content (>75%) in the polybutadiene fraction of the copolymer (each type of polymer, SBR or BR, may be obtained with one or more initiator compounds comprising earth alkaline metal compounds, such as described in U.S. Pat. Nos. 6,693,160; 6,627,715; 6,489,415; 6,103,842; 5,753,579; 5,086,136; and 3,629,213, each of which is hereby incorporated herein by reference in its entirety: or by using catalysts based on cobalt, such as described in U.S. Pat. Nos. 6,310,152; 5,834,573; 5,753,761; 5,448,002 and 5,089,574 and U.S. Patent Application Publication No. 2003/0065114, each of which is hereby incorporated herein by reference in its entirety; or by using catalysts based on vanadium, such as described in EP 1 367 069; JP 11301794 and U.S. Pat. No. 3,951,936, each of which is hereby incorporated herein by reference in its entirety; or by using catalysts based on neodymium, such as described in EP 0 964 008, EP 0 924 214 and U.S. Pat. Nos. 6,184,168; 6,018,007; 4,931,376; 5,134,199 and 4,689,368, each of which is hereby incorporated herein by reference in its entirety).

The composition of the invention may also be used for producing high impact polystyrene (HIPS) and butadiene-modified acrylonitrile-butadiene-styrene copolymer (ABS) (see, for example, WO 2009/148932, incorporated herein by reference).

DEFINITIONS

Unless specifically indicated otherwise, the expression "polymer" as used herein is intended to encompass both unmodified polymer and modified (i.e. chain end-modified) polymer.

Alkyl groups as defined herein, whether as such or in association with other groups, such as alkylaryl or alkoxy, include both straight chain alkyl groups, such as methyl (Me), ethyl (Et), n-propyl (Pr), n-butyl (Bu), n-pentyl, n-hexyl, etc., branched alkyl groups, such as isopropyl, tert-butyl, etc. and cyclic alkyl groups, such as cyclohexyl.

Alkoxy groups as defined herein include methoxy (MeO), ethoxy (EtO), propoxy (PrO), butoxy (BuO), isopropoxy, isobutoxy, pentoxy, etc.

Aryl groups as defined herein include phenyl, biphenyl and other benzenoid compounds. Aryl groups preferably contain only one aromatic ring and most preferably contain a $C_6$ aromatic ring.

Alkylaryl groups as defined herein refer to a combination of one or more aryl groups bound to one or more alkyl groups, for example in the form of alkyl-aryl, aryl-alkyl, alkyl-aryl-alkyl and aryl-alkyl-aryl. Alkylaryl groups preferably contain only one aromatic ring and most preferably contain a $C_6$ aromatic ring.

EXAMPLES

The following examples are provided in order to further illustrate the invention and are not to be construed as limiting. They include the preparation of the polymerization initiator; the preparation of sulfanylsilane chain end modifying agent; the preparation and testing of polymers; and the preparation and testing of uncrosslinked polymer compositions, including the first and second polymer compositions, as well as of cross-linked or cured polymer compositions, also referred to as vulcanized polymer composition. Unless stated otherwise, all parts and percentages are expressed on a weight basis. The term "overnight" refers to a time of approximately 16-18 hours. "Room temperature" refers to a temperature of about 20° C. The polymerizations were performed under exclusion of moisture and oxygen in a nitrogen or argon atmosphere. The vinyl content in the conjugated diolefin part of the polymer chain was determined by IR absorption spectrometry (Morello method, IFS 66 FT-IR spectrometer of Bruker Analytic GmbH). The IR samples were prepared using $CS_2$ as swelling agent.

Bound styrene content: A calibration curve was prepared by IR absorption spectrum (IFS 66 FT-IR spectrometer of Bruker Analytik GmbH). The IR samples were prepared using $CS_2$ as swelling agent. For the IR determination of the bound styrene in styrene-butadiene copolymers, four bands are assessed: a) band for trans-1,4-polybutadiene units at 966 $cm^{-1}$, b) band for cis-1,4-polybutadiene units at 730 $cm^{-1}$, c) band for 1,2-polybutadiene units at 910 $cm^{-1}$ and band for bound styrene (styrene aromatic bond) at 700 $cm^{-1}$. The band heights are normalized according to the appropriate extinction coefficients and summarized to a total of 100%. The normalization is done via $^1H$— and $^{13}C$-NMR. The styrene content was alternatively determined by NMR (Avance 400 device ($^1H$=400 MHz; $^{13}C$=100 MHz) of Bruker Analytik GmbH).

The 1D NMR spectra were collected on a BRUKER Avance 400 NMR spectrometer (BRUKER BioSpin GmbH) using a 5 mm dual detection probe. The field homogeneity was optimized by maximizing the deuterium lock signal. The samples were shimmed by optimizing the deuterium lock signal. The samples were run at room temperature (298 K). The following deuterated solvents were used: $C_6D_6$ (7.16 ppm for $^1H$; 128.06 ppm for $^{13}C$-NMR), $CDCl_3$ (7.24 ppm for $^1H$; 77.03 ppm for $^{13}C$-NMR), the signals of the remaining protons of deuterated solvents were each used as an internal reference.

For spectral processing, the BRUKER 1D WINNMR software (version 6.0) was used. Phasing, base line correction and spectral integration of the resulting spectra was done in the manual mode. For acquisition parameters see Table 1.

TABLE 1

| 1D-NMR acquisition parameters using BRUKER standard pulse sequences | | |
|---|---|---|
| | 1H-NMR | 13C-NMR |
| Observe frequency | 400.130 MHz | 100.613 MHz |
| Spectral width | 8278.146 Hz | 23980.814 Hz |
| BRUKER Pulse program | Zg30 | Zgpg30 |
| Pulse angle | 30° | 30° |
| Relaxation delay | 1.0 s | 2.0 s |
| Number of Data points for FT | 32K | 32K |
| Line broadening | 0.3 Hz | 1 Hz |
| Number of accumulated scans | 64 | >1000 |

GPC-Method: SEC calibrated with narrow distributed polystyrene standard.
Sample Preparation:
a1) Oil-Free Polymer Samples:
About 9-11 mg dried polymer sample (moisture content <0.6%) was dissolved in 10 mL tetrahydrofuran using a brown vial of 10 mL size. The polymer was dissolved by shaking the vial for 20 min at 200 u/min.
a2) Oil-Containing Polymer Samples:
About 12-14 mg dried polymer sample (moisture content <0.6%) was dissolved in 10 mL tetrahydrofuran using a brown vial of 10 mL size. The polymer was dissolved by shaking the vial for 20 min at 200 u/min.
b) Polymer solution was transferred into a 2 ml vial using a 0.45 μm disposable filter.
c) The 2 ml vial was placed on a sampler for GPC analysis.
Elution rate: 1.00 mL/min
Injection volume: 100.00 μm (GPC-method B 50.00 μm)
The measurement was performed in THF at 40° C. Instrument: Agilent Serie 1100/1200; Module setup: Iso pump, autosampler, thermostat, VW-Detector, RI-Detector, Degasser; Columns PL Mixed B/HP Mixed B. In each GPC-device 3 columns were used in an connected mode. The length of each of the columns: 300 mm; Column Type: 79911 GP-MXB, Plgel 10 μm MIXED-B GPC/SEC Columns, Fa. Agilent Technologies.
GPC Standards: EasiCal PS-1 Polystyrene Standards, Spatula A+B Styrene Standard Manufacturer: Polymer Laboratories (Varian Deutschland GmbH)
Polydispersity (Mw/Mn) was used as a measure of molecular weight distribution. The calculation of Mw (weight average molecular weight) and Mn (number average molecular weight) was based on one of two procedures.

Mp1, Mp2, Mp3 correspond to the (maximum peak) molecular weight measured at the first, second or third peaks of the GPC curve [the first peak Mp1 (lowest molecular weight) is located on the right side of the curve and the last peak (highest molecular weight) is located on the left side of the curve], respectively. Maximum peak molecular weight means the molecular weight of the peak at the position of maximum peak intensity. Mp2 and Mp3 are two or three polymer chains coupled to one macromolecule. Mp1 is one polymer chain (base molecular weight—no coupling of two or more polymer chains to one macromolecule). The total coupling rate represents the sum of the weight fractions of coupled polymers relative to the total polymer weight, including the sum of the weight fractions of all coupled polymers and the uncoupled polymer. The total coupling rate is calculated as:

CR(total)=(ΣArea fraction of all coupled peaks [Peak with maximum Mp2 to peak with highest indexed peak maximum])/(ΣArea fraction of all peaks [Peak with peak maximum Mp1 to peak with highest indexed peak maximum]).

The individual coupling rate (e.g. two polymer arms coupled corresponding to the peak with peak maximum Mp2) is calculated as:

CR(2arms)=(Area fraction of peak with peak maximum Mp2)/(ΣArea fraction of all peaks [Peak with peak maximum Mp1 to peak with highest indexed peak maximum]).

The oil content in the oil extended polymers was determined by extraction method according to ASTM D 5574-95 using a microwave extraction apparatus (MARS from CEM) and a sample weight of 1 g. The extracted rubber sample was dried at 140° C. for 30 minutes.

Rubber compounds were prepared by combining the constituents listed below in Table 4 in a 380 cc Banbury mixer (Labstation 350S from Brabender GmbH&Co KG), following a two-stage mixing process. Stage 1—mixing all components together, except the components of the vulcanization package, to form a stage 1 formulation. Stage 2—mixing of components of vulcanization package mixed into stage 1 formulation to form a stage 2 formulation.

Mooney viscosity was measured according to ASTM D 1646 (2004), with a preheating time of one minute and a rotor operation time of 4 minutes, at a temperature of 100° C. [ML1+4(100° C.)], on a MV 2000E from Alpha Technologies UK. The rubber Mooney viscosity measurement is performed on dry (solvent free) raw polymer (unvulcanized rubber). The Mooney values of the raw polymers are listed in Table 3. The Compound Mooney viscosity is measured on an uncured (unvulcanized) second state polymer compound sample prepared according to Table 4. The Compound Mooney values are listed in Table 5.

Measurement of unvulcanized rheological properties was performed according to ASTM D 5289-95 (reapproved 2001), using a rotor-less shear rheometer (MDR 2000 E from Alpha Technologies UK) to measure Time to Cure (TC). The rheometer measurement was performed at a constant temperature of 160° C. on an non-vulcanized second stage polymer formulation, according to Table 4. The amount of polymer sample is about 4.5 g. Sample shape and shape preparation are standardized and defined by the measurement device (MDR 2000 E from Alpha Technologies UK). The TC 50 and TC 90 values are the respective times required to achieve 50% and 90% conversion of the vulcanization reaction. The torque is measured as a function of time of reaction. The vulcanization conversion is automatically calculated from the generated torque versus time curve. The TS 1 and TS 2 values are the respective times required to increase the torque by 1 dNm and 2 dNm above the respective torque minimum (ML) during vulcanization.

Tensile Strength, Elongation at Break and Modulus at 300% Elongation (Modulus 300) were measured according to ASTM D 412-98A (reapproved 2002), using a dumbbell die C test piece on a Zwick Z010. Of the standardized dumbbell die C test pieces, those of 2 mm thickness were used. The tensile strength measurement was performed at room temperature, on a cured (vulcanized) second stage polymer sample, prepared according to Table 4. Stage 2 formulations were vulcanized within 16-25 minutes at 160° C. to TC 95 (95% vulcanization conversion) (see cure data in Table 5).

Heat build-up was measured according to ASTM D 623, method A, on a Doli Goodrich Flexometer. The measurement was performed on a vulcanized second stage polymer samples according to Table 5. Stage 2 formulations were vulcanized at 160° C. to TC 95 (95% vulcanization conversion) (see cure data in Table 5).

Rebound resilience was measured according to DIN 53512 at 0° C. and 60° C. on a Zwick 5109. The measurement was performed on a cured (vulcanized) second stage polymer sample, prepared according to Table 4. Stage 2 formulations were vulcanized at 160° C. to TC 95 (95% vulcanization conversion) (see cure data in Table 5). The smaller the index at 0° C. the better the wet skid resistance (lower=better). The larger the index at 60° C., the lower the hysteresis loss and lower the rolling resistance (higher=better).

DIN abrasion was measured according to DIN 53516 (1987 Jun. 1). The larger the index, the lower the wear resistance (lower=better). The abrasion measurement was performed on a vulcanized, second stage polymer formulation according to Table 5.

In general, the higher the values for Elongation at Break, Tensile Strength, Modulus 300 and rebound resilience at 60° C. the better the sample performance; whereas the lower the Heat Build-Up, rebound resilience at 0° C. and Abrasion, the better the sample performance. Preferably TS 1 is >0.5 minute, TS 2 is >1.5 minutes, TC 50 is from 3 to 8 minutes, and TC 90 is from 8 to 19 minutes.

Modifier Preparation: Four polymerization initiator precursor compounds (P1 to P4), four polymerization initiators (I1 to I4) and two chain end modifying agents were used. Polymerization initiator precursor compounds P1 to P4 and polymerization initiators I1, I2, I3 and I4 are in accordance with the invention.

Characterization of the Divinylidene Polymerization Initiator Precursor Compounds The divinylidene precursor compounds P1-P4 were synthesized according to the process described in the U.S. Pat. No. 4,982,029 and are shown and characterized below:

P1

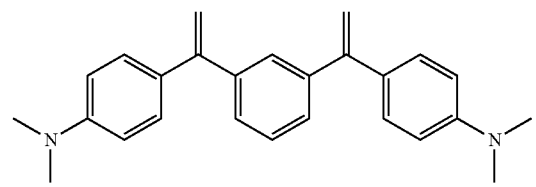

$^1$H-NMR (300 MHz, 23° C., CDCl$_3$): δ=7.42 (s, 1H, Ar—H), 7.30 (s, 7H, Ar—H), 6.73 (d, 4H, Ar—H), 5.40 (s, 2H, =CH$_2$), 5.28 (s, 2H, =CH$_2$), 2.98 (s, 12H, NCH$_3$) ppm; $^{13}$C-NMR (75 MHz, 23° C., CDCl$_3$) δ=149.94, 149.70, 141.70, 128.97, 128.46, 127.78, 127.64, 112.20, 111.49, 40.65 ppm.

P2

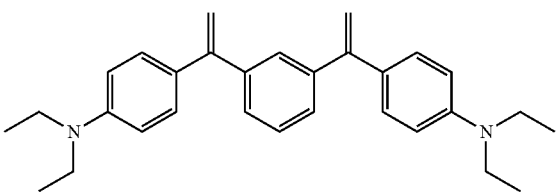

$^1$H-NMR (400 MHz, 23° C., C$_6$D$_6$): δ=7.50-7.48 (m, 2H, Ar—H), 7.45-7.42 (m, 4H, Ar—H), 6.50-6.48 (m, 4H, Ar—H), 5.50 (d, 2H, =CH$_2$), 5.37 (d, 2H, =CH$_2$), 2.93 (q,

8H, NCH$_2$), 0.85 (t, 12H, NCH$_2$CH$_3$) ppm; $^{13}$C-NMR (101 MHz, 23° C., C$_6$D$_6$) δ=150.70, 147.71, 143.06, 129.73, 129.22, 128.41, 128.32, 128.19, 111.74, 111.07, 44.34, 12.67 ppm.

P3

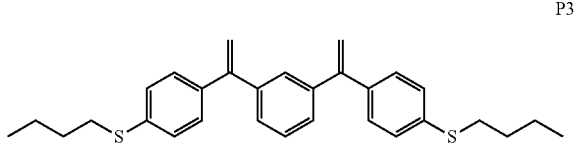 [SMILES: C=C(c1ccc(SCCCC)cc1)c1cccc(C(=C)c2ccc(SCCCC)cc2)c1]

$^1$H-NMR (300 MHz, 23° C., C$_6$D$_6$): δ=7.28-7.09 (m, 12H, Ar—H), 5.36 (d, 4H,=CH$_2$), 2.65 (t, 4H, SCH$_2$), 1.47 (q, 4H, CH$_2$), 1.24 (sext., 4H, CH$_2$), 0.74 (t, 6H, CH$_3$) ppm.

P4

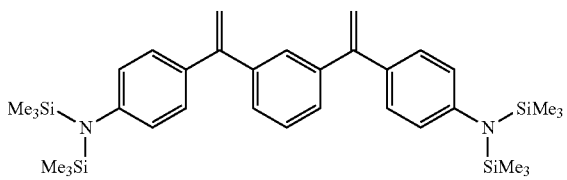

$^1$H-NMR (400 MHz, 23° C., C$_6$D$_6$): δ=7.66 (m, 1H, Ar—H), 7.32-7.25 (m, 6H, Ar—H), 7.09-7.05 (m, 1H, Ar—H), 6.84-6.80 (m, 4H, Ar—H), 5.40 (d, 2H,=CH$_2$), 5.35 (d, 2H, =CH$_2$), 0.12 (s, 36H, Si(CH$_3$)$_3$) ppm; $^{13}$C-NMR (101 MHz, 23° C., C$_6$D$_6$) δ=150.10, 148.05, 142.36, 137.12, 130.07, 128.82, 128.32, 128.16, 113.69, 2.26 ppm.

Initiator Compounds
Preparation of Initiator I1

I1

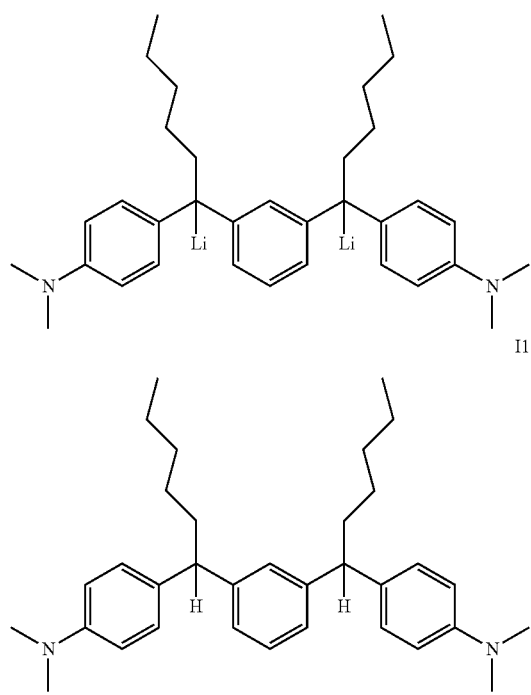

I1a

A typical initiator mixture comprising I1, such as used in the preparation of Example 2 in Table 2, was prepared as follows. The precursor compound P1 (36.9 g 100 mmol) as dissolved in 400 mL cyclohexane. TMEDA (40.7 g, 350 mmol) and n-BuLi (63.4 g, 200 mmol, 20 wt % solution in cyclohexane) were added. The color of the solution immediately turned dark red indicating the formation of the dianion I1. Due to the very high air and moisture sensitivity of I1, the compound was characterized as its hydrolyzed product I1a. Therefore, a sample of the initiator mixture was hydrolyzed with an excess of methanol and characterized by NMR and GC-MS.

$^1$H-NMR (400 MHz, 23° C., C$_6$D$_6$): δ=6.94-6.86 (m, 8H, Ar—H), 6.33-6.31 (m, 4H, Ar—H), 3.63-3.58 (m, 2H, 2x Ar—CH—Ar), 2.22 (s, 12H, NCH$_3$), 1.82-1.76 (m, 2H, Ar$_2$CH—CH$_2$), 1.07-0.88 (m, 12H, (CH$_2$K)$_3$CH$_3$), 0.54 (t, 6H, (CH$_2$)$_3$CH$_3$) ppm; $^{13}$C-NMR (101 MHz, 23° C., C$_6$D$_6$) δ=149.43, 146.72, 134.07, 128.86, 128.65, 128.16, 128.15, 127.91, 113.35, 50.99, 40.50, 36.63, 32.34, 28.28, 22.99 ppm. GC-MS (EI, 70 eV): m/z (%)=485 (M$^+$, 22), 413 (M$^+$—CH$_3$—C$_4$H$_9$, 100), 327 (4), 207 (4), 171 (51), 134 (4).

Initiators I2, I3 and I4 were Prepared In Situ.

The preparation of the initiator mixtures comprising the compounds I2-I4 were performed in situ according to the procedure described for I1 above. The structures for I2, I3 and I4 are depicted below.

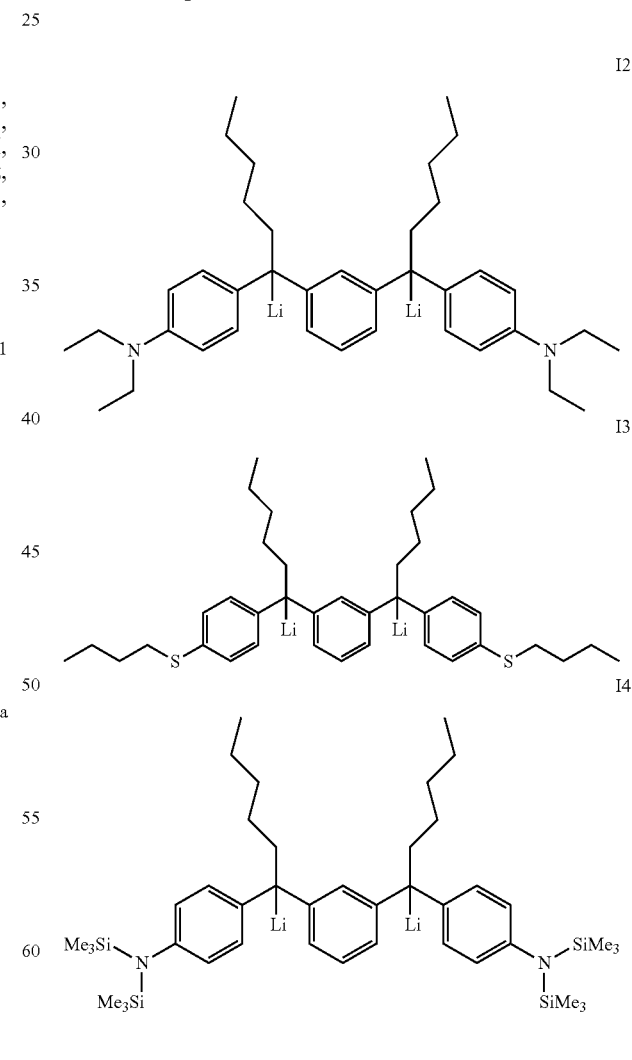

Chain End Modifying Agents

Chain End Modifying Agent E1 was prepared by two preparation pathways as follows:

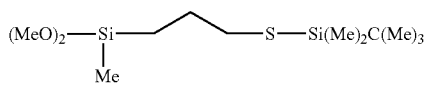

E1

Preparation Pathway 1 (E1):
To a 100 mL Schlenk flask was charged 25 ml tetrahydrofuran (THF), 79.5 mg (10 mmol) lithium hydride, and subsequently, 1.18 g (10 mmol) gamma-mercaptopropyl (methyl)dimethoxysilane from the ABCR GmbH. The reaction mixture was stirred for 24 hours at room temperature, and another two hours at 50° C. Than tert-butyl dimethyl chloro silane (1.51 g (10 mmol)) was dissolved in 10 g THF, and the resulting solution was then added drop wise to the Schlenk flask. Lithium chloride precipitated. The suspension was stirred for about 24 hours at room temperature, and for another two hours at 50° C. The THF solvent was removed under vacuum. Then cyclohexane (30 ml) was added. The white precipitate was subsequently separated by filtration. The cyclohexane solvent was removed under vacuum (under reduced pressure). The resulting colorless liquid solution proved to be 99% pure per GC, and therefore no further purification was necessary. A yield of 3.1 g (9.3 mmol) of chain end-modifier agent E1 was obtained.

Preparation Pathway 2 (E1):
To a 100 mL Schlenk flask was charged 1.18 g (10 mmol) gamma-mercaptopropyl(methyl)dimethoxysilane from the ABCR GmbH, 25 ml tetrahydrofuran (THF), and subsequently, 0.594 g (11 mmol) sodium methanolate (NaOMe) dissolved in 10 mL THF. The reaction mixture was stirred for 18 hours at room temperature. Then tert-butyl dimethyl chloro silane (1.51 g (10 mmol)) was dissolved in 10 g THF, and the resulting solution was then added drop wise to the Schlenk flask. Sodium chloride precipitated. The suspension was stirred for about 24 hours at room temperature, and for another two hours at 50° C. The THF solvent was removed under vacuum. Then cyclohexane (30 ml) was added. The white precipitate was subsequently separated by filtration. The cyclohexane solvent was removed under vacuum (under reduced pressure). The resulting colorless liquid solution proved to be 89% pure per GC. Further purification consisted in a fractionated distillation, and a yield of 2.6 g (7.9 mmol) of chain-end modifier agent E1 was obtained.

Chain End Modifying Agent E2 was purchased as N,N-dimethyl-3-aminopropylmethyldimethoxysilane from ABCR GmbH.

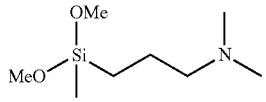

E2

Randomizers
TMEDA (N,N,N',N'-Tetramethyl-ethylene-1,2-diamine) was purchased from Sigma-Aldrich and was dried over molecular sieve prior to use.

Copolymerization of 1,3-Butadiene with Styrene (Examples 1-11)

The co-polymerizations were performed in a double wall, 10 liter steel reactor, which was first purged with nitrogen, before the addition of organic solvent, monomers, polar coordinator compound, initiator compound or other components. The polymerization reactor was tempered to 60° C., unless stated otherwise. The following components were then added in the following order: cyclohexane solvent (4600 grams); butadiene monomer, styrene monomer, tetramethylethylene diamine (TMEDA) and optionally divinylbenzene (DVB; Bowden Chemicals Ltd.; 0.16 M solution in cyclohexane; 1,3-DVB/1,4-DVB=70/30), and the mixture was heated to 40° C., followed by titration with n-butyl lithium to remove traces of moisture or other impurities. The desired polymerization initiator compound was added into the polymerization reactor to initiate the polymerization reaction. The polymerization was performed for 80 minutes, not allowing the polymerization temperature to exceed 60° C. Afterwards, 2.3% of the total butadiene monomer amount was added, followed by the addition of the chain end modifier, unless stated otherwise. After 20 minutes the polymerization was terminated by the addition of methanol (2 equivalents based on initiator). To the polymer solution, 2.20 g IRGANOX 1520 was added as a stabilizer. This mixture was stirred for 10 minutes. Optionally TDAE oil was added and the resulting polymer solution (Examples 10 and 11, Table 2 and Table 3) was stirred for 30 minutes to ensure homogenous distribution of the oil. The resulting polymer solution was than stripped with steam for one hour to remove solvent and other volatiles, and dried in an oven at 70° C. for 30 minutes and then additionally for one to three days, at room temperature. The resulting polymer composition and several of its properties are summarized in Table 3 below. Unless otherwise stated, quantities are expressed in mmols.

Unless indicated otherwise, monomer conversions of more than 99% by weight were achieved for all experiments listed in Table 2. Monomer conversion was measured as polymer solid content representing the weight of polymer after removal of the polymerization solvent and any volatile components. The corresponding polymer solution sample was taken from the polymerization reactor shortly prior to termination of the polymerization process.

A dash "-" in the tables indicates that no constituent was added. "N.M." indicates that no measurement was taken, or that corresponding data was unavailable.

TABLE 2

Composition of Examples - amounts of reagents for polymerization components

| Ex. | N-butyl lithium initiator or divinyliden-initiator (mmol) | Coupling agent (mmol) | Chain-End Modifier (mmol) | Butadiene (mol) | Styrene (mol) | TMEDA (mol) |
| --- | --- | --- | --- | --- | --- | --- |
| 1 (Ref) | (BuLi) 3.296 | — | — | 13.11 | 1.814 | 7.375 |
| 2 | (I1) 3.635 | — | — | 13.04 | 1.804 | 17.08 |
| 3 | (I2) 3.617 | — | — | 13.05 | 1.806 | 16.09 |
| 4 | (I3) 3.789 | — | — | 13.03 | 1.804 | 17.07 |
| 5 | (I2) 3.764 | — | (E1) 9.186 | 12.95 | 1.792 | 16.57 |
| 6 | (I3) 3.604 | — | (E1) 9.111 | 12.95 | 1.791 | 15.80 |
| 7 | (I1) 3.710 | — | (E2) 7.430 | 13.01 | 1.801 | 17.86 |
| 8 | (I1) 4.465 | (DVB) 1.338 | (E1) 10.76 | 12.84 | 1.776 | 20.47 |
| 9 | (I4) 3.614 | — | (E1) 8.748 | 12.97 | 1.794 | 14.46 |
| 10 | (I1) 13.85 | — | (E1) 34.82 | 44.26 | 6.800 | 55.55 |
| 11 | (I1) 13.86 | — | (E1) 34.93 | 49.26 | 6.801 | 55.55 |

TABLE 3

Polymer Characterizations

| Example | Mw [g/mol] | Mn [g/mol] | Mp1 [g/mol] | Coupling Rate[A] [%] | TDAE content [wt %] | Mooney* viscosity [MU] | Mooney** viscosity [MU] | Vinyl content[B] [wt %] | Styrene content[C] [wt %] |
|---|---|---|---|---|---|---|---|---|---|
| 1 (Ref) | 368303 | 338324 | 375894 | — | — | — | 74.6 | 61.5 | 21.2 |
| 2 | 383290 | 336898 | 393462 | — | — | — | 76.2 | 65.4 | 20.5 |
| 3 | 359950 | 323988 | 373495 | — | — | — | 71.3 | 65.5 | 20.5 |
| 4 | 367029 | 315169 | 385296 | — | — | — | 63.1 | 66.0 | 20.6 |
| 5 | 361223 | 316871 | 355718 | — | — | — | 66.7 | 65.5 | 20.7 |
| 6 | 375742 | 316733 | 374837 | — | — | — | 75 | 62.8 | 21.8 |
| 7 | 368758 | 316370 | 374188 | — | — | — | 64.1 | 65.3 | 20.8 |
| 8 | 429823 | 313597 | 303877 | 27.9 | — | — | 65.8 | 65.9 | 20.8 |
| 9 | 499654 | 378495 | 471271 | — | — | — | 95.5 | N.M | N.M. |
| 10 | 387799 | 328806 | 358687 | — | 7.2 | 49.0 | — | 20.8 | 64.9 |
| 11 | 380686 | 327862 | 362452 | — | 9.6 | 41.1 | — | 20.8 | 64.9 |

*Mooney viscosity of oil free grade
**Mooney viscosity of TDAE oil containing grade
[A] determined by SEC
[B] vinyl content is that of the 1,2-polybutadiene unit content of the final copolymer, and is determined by IR Spectroscopy
[C] styrene content of the final copolymer, and is determined by IR Spectroscopy Polymer Compositions Polymer compositions were prepared by combining and compounding the constituents listed below in Table 4 in a 380 ml Banbury mixer and vulcanized at 160° C. for 20 minutes. Vulcanization process data and physical properties for each composition example are provided in Table 5 and Table 6.

TABLE 4

Polymer Composition using polymers 1-5

| Components | | Amount (phr)[n] |
|---|---|---|
| 1st mixing stage | | |
| Elastomeric polymer Example (solution styrene butadiene copolymer) | | 80.0 |
| High cis 1,4-polybutadiene | Buna cis 132-Schkopau[m] | 20.0 |
| Precipitated silica | Ultrasil 7000GR[f] | 80.0 |
| Silane | Si 75[f,i] | 6.9 |
| Stearic acid[j] | | 1.0 |
| Stabilizer system Ozone protecting wax | Antilux 654[h] | 1.5 |
| Antiozonant | Dusantox[g] 6PPD | 2.0 |
| Zinc oxide[k] | | 2.5 |
| Softener (Oil) | TDAE[e] | 20.0 |
| 2nd mixing stage | | |
| Sulfur[d,l] | | 1.4 |
| TBBS[b,d] | | 1.5 |
| DPG[c,d] | | 1.5 |

[a] 2 stage mixing, Brabender 350S, Internal Banbury mixer
[b] N-tert-Butyl-2-benzothiazyl-sulfenamide; Rhein Chemie Rheinau GmbH TABLE 4-continued Polymer Composition using polymers 1-5

| Components | Amount (phr)[n] |
|---|---|

[c] Diphenylguanidine, Vulkacit D, Lanxess AG
[d] Second stage (curing system)
[e] VivaTec 500, Hansen & Rosenthal KG
[f] Evonic Degussa GmbH
[g] N-(1,3-dimethylbutyl)-N'-phenyl-1,4-benzenediamine, Duslo a.s.
[h] Light & ozone protective wax, Rhein Chemie Rheinau GmbH
[i] Bis(triethoxysilylpropyl)disulfan, sulfur equivalents per molecule: 2.35
[j] Cognis GmbH
[k] Grillo-Zinkoxid GmbH
[l] Solvay AG
[m] Styron Deutschland GmbH
[n] Based on sum weight of the styrene butadiene copolymer and high cis 1,4-polybutadiene

TABLE 5

Vulcanization Process Data & Silica-Containing Polymer Composition Mooney Viscosity

| Example | Compound Mooney [Mu] | TS 1 [min] | TS 2 [min] | TC 50 [min] | TC 90 [min] | TC 95 [min] |
|---|---|---|---|---|---|---|
| 1A (Ref) | 81.9 | 0.6 | 2.2 | 5.7 | 14.2 | 19.3 |
| 2A | 78.6 | 0.5 | 2.1 | 6.0 | 14.6 | 19.6 |
| 3A | 80.4 | 0.6 | 2.2 | 5.6 | 14.4 | 19.5 |
| 4A | 68.0 | 0.6 | 2.6 | 6.2 | 14.9 | 19.8 |
| 5A | N.M. | 0.5 | 1.7 | 6.3 | 15.3 | 20.4 |

TABLE 6

Silica-Containing Polymer Vulcanizate Composition Properties

| Example | Tensile Strength [MPa] | Elongation at Break [%] | Modulus 300 [MPa] | Rebound resilience @ 60° C. [%] | Rebound resilience @ 0° C. [%] | Heat build-up [° C.] | DIN Abrasion 0.5 kg load [mm³] |
|---|---|---|---|---|---|---|---|
| 1A (Ref) | 19.7 | 445 | 11.3 | 54.0 | 11.9 | 124.1 | 150 |
| 2A | 18.8 | 421 | 11.9 | 54.6 | 10.1 | 119.4 | 139 |

TABLE 6-continued

Silica-Containing Polymer Vulcanizate Composition Properties

| Example | Tensile Strength [MPa] | Elongation at Break [%] | Modulus 300 [MPa] | Rebound resilience @ 60° C. [%] | Rebound resilience @ 0° C. [%] | Heat build-up [° C.] | DIN Abrasion 0.5 kg load [mm³] |
|---|---|---|---|---|---|---|---|
| 3A | 19.9 | 444 | 11.3 | 53.8 | 10.9 | 121.7 | 139 |
| 4A | 19.4 | 166 | 10.7 | 53.1 | 10.4 | 122.0 | 142 |
| 5A | 20.4 | 372 | 14.0 | 62.7 | 9.8 | 96.9 | 127 |

Surprisingly, it was found that the initiator compounds of the invention produce polymers which can be used for the preparation of polymer compositions and vulcanized polymer compositions. The vulcanized (or cured) polymer compositions based on polymers made by using the initiator compounds of the invention (see for example 2A in Fable 6) have a relatively low (or reduced) rebound resilience at 0° C.; relatively decreased tire heat build-up and relatively decreased DIN abrasion, when compared with vulcanized elastomeric polymer compositions based on polymers not made with a polymerization initiator compound of the invention (see example 1A in Table 5 and Table 6). Exemplary vulcanized composition 2A, which is based on polymer 2, prepared from initiator I1 of the invention, has a heat build-up value of 119.4° C. while vulcanized composition 1A, based on non-modified polymer 1, formed from n-butyl lithium initiator, has a relatively higher heat build-up value of 124.1° C. and a relatively higher DIN abrasion value of 150 mm³ (compared to 139 mm³ of compound 2A).

A first polymer composition of the invention may be converted into a second polymer compositions (first stage mixing [mixing step in which silica filler is added to polymer] and second stage mixing according to Table 4, involving silica filler and polymer of the invention), then further converted into a vulcanized polymer composition, for example by curing the second stage mixing result according to Table 4 at 160° C. for 20 min as described herein. The second polymer compositions and vulcanized polymer compositions (as listed in Table 4 and Table 5) prepared under identical conditions at the same day by the identical operator are identified with the capital letter A. The polymer contained in the vulcanized polymer composition is identified by the polymer number, e.g. 1, 2, etc. . As a result, there is one vulcanized polymer composition series (including compositions 1A, 2A, 3A, 4A and 5A) which can be directly compared with each other.

In accordance with the invention, the combination of the initiator compounds such as I1, I2, I3 or I4 with one or more chain-end modifying compounds such as E1 or E2 and optionally with a coupling agent leads to the formation of the polymers of the invention, which have relatively lower heat build-up under mechanical stress, lower rebound resilience at 0° C. values and lower abrasion resistance when present in vulcanized polymer compositions, compared with polymers in comparative vulcanized polymer compositions not containing polymers made by using polymerization initiator compounds of the invention.

As shown in Table 5, "heat build-up" during dynamic deformation, rebound resilience at 0° C., compound Mooney and DIN abrasion of the vulcanized polymer compositions comprising modified polymers of the invention is reduced. Polymer "heat build-up" reduction is believed to improve the durability of the resulting vulcanized polymer composition, to reduce the vulcanizate hysteresis energy loss, leading to a decreased rolling resistance, to increase overall elasticity and to improve handling characteristics of a tire. A low DIN abrasion value indicates increased vulcanizate durability and abrasion resistance. Decreased rebound resilience at 0° C. of the vulcanized polymer composition compared with vulcanizates comprising reference (non-inventive) polymers indicate improved grip properties on a wet surface. "Compound Mooney" values of non-cured first or second polymer compositions are decreased or at least in a similar range compared with polymer compositions comprising reference polymers; a reduced compound Mooney indicating a reduced polymer composition viscosity and leads to a more economic mixing process (e.g. mixing polymer with fillers and additives). "Tensile Strength" and "Modulus 300" are not or not significantly deteriorated in comparison with the reference polymer, suggesting the formation of a stable polymer network with a higher resistance under mechanical stress. More specific vulcanizates comprising polymers prepared from modified initiator compounds according to the invention in combination with chain-end modifiers (Example 5A, Table 6) leads to an increasing of the values of Tensile strength and Modulus 300, indicating an improved interaction with the silica filler compared with vulcanizates comprising reference polymers (Example 1A, Table 6). Although some "Elongation at Break" values are slightly reduced, they are still very acceptable considering the degree of improvement of the heat build-up and abrasion resistance values.

The effect of SSBR-silica vulcanizates according to the invention is further substantiated as follows. The vulcanizate comprising a polymer made by a combination of the polymerization initiator compound I1, prepared from the precursor P1, n-butyl lithium and TMEDA, in Example 2A of Table 5 has relatively lower heat build-up and DIN abrasion as compared to the counterpart example 1A prepared without the polymerization initiator compound. According to Table 6, the cured (vulcanized) polymer composition of the invention 2A has a lower rebound resilience at 0° C. than the counterpart Example 1A, prepared without the polymerization initiator compound. Furthermore, modified SSBR-silica vulcanizates comprising a polymer made by a combination of the polymerization initiator compound I1, prepared from the precursor P1, n-butyl lithium and TMEDA, with chain end modifying agent E1 in Example 5A of Table 5 has relatively lower heat build-up and DIN abrasion as compared to the counterpart examples prepared without polymerization initiator compound (Example 1A) and prepared with polymerization initiator compound, but without chain end modifying agent (Examples 2A, 3A, 4A). According to Table 6, the vulcanized polymer composition of the invention 5A comprising polymer 5, made by using polymerization initiator I1 and chain end modifying agent E1, has a lower rebound at 0° C., a higher rebound at 60° C. and a higher Modulus 300 compared to the counterpart examples prepared without polymerization initiator compound (Example 1A) and prepared with the polymerization initiator compound, but without chain end modifying agent (Examples 2A, 3A, 4A). Accordingly, the polymerization initiator of the invention in combination with an efficient chain end modifying agent (e.g. E1) improves the specified vulcanized polymer composition properties as compared to other compositions not containing an initiator of the invention or containing an initiator of the invention, but not containing a chain end modifying agent.

The invention claimed is:

1. A method of making a polymer, comprising the step of reacting
   i) a polymerization initiator, represented by the following Formula 1,

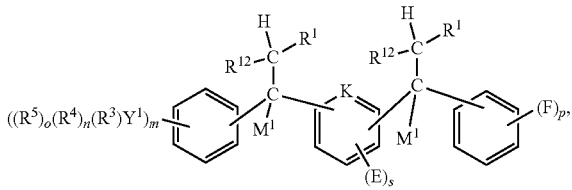

Formula 1 or a Lewis base adduct thereof, and
   ii) at least one type of polymerizable monomers selected from conjugated olefins and aromatic vinyl compounds,
wherein
   each $M^1$ is independently selected from lithium, sodium and potassium;
   each $R^1$ is independently selected from $(C_1\text{-}C_{100})$ alkyl and $(C_2\text{-}C_{100})$ alkenyl, optionally substituted with one or more $(C_6\text{-}C_{12})$ aryl groups and optionally linked to the carbon atom C by up to 25 monomer units selected from conjugated diene monomers and aromatic vinyl compounds, especially butadiene, isoprene and styrene;
   each $R^{12}$ is independently selected from hydrogen, $(C_1\text{-}C_{10})$ alkyl, $(C_6\text{-}C_{12})$ aryl and $(C_7\text{-}C_{18})$ alkylaryl;
   each $Y^1$ is independently selected from a nitrogen atom, a sulfur atom and a silicon atom;
   $R^3$, $R^4$ and $R^5$ are each independently selected from $(C_1\text{-}C_{18})$ alkyl, $di(C_1\text{-}C_6)$ alkyl amine (only when $Y^1$ is a silicon atom), $(C_6\text{-}C_{18})$ aryl, $(C_7\text{-}C_{18})$ alkylaryl and, when $Y^1$ is not a silicon atom, $-SiR^{14}R^{15}R^{16}$, wherein $R^{14}$, $R^{15}$ and $R^{16}$ are each independently selected from $(C_1\text{-}C_{18})$ alkyl, $(C_6\text{-}C_{18})$ aryl and $(C_7\text{-}C_{18})$ alkylaryl; n and o are each an integer selected from 0 and n+o=1 when $Y^1$=N, n=o=0 when $Y^1$=S, and n+o=2 when $Y^1$=Si;
   m is an integer selected from 1, 2 and 3;
   each E is independently selected from $(C_1\text{-}C_{18})$ alkyl, $(C_6\text{-}C_{18})$ aryl, $(C_7\text{-}C_{18})$ alkylaryl and $-Y^3(R^9)(R^{10})_t(R^{11})_u$, wherein
      $Y^3$ is selected from a nitrogen atom, a sulfur atom and a silicon atom; $R^9$, $R^{10}$ and $R^{11}$ are each independently selected from $(C_1\text{-}C_{18})$ alkyl, $di(C_1\text{-}C_6)$ alkyl amine (only when $Y^3$ is a silicon atom), $(C_6\text{-}C_{18})$ aryl, $(C_7\text{-}C_{18})$ alkylaryl and, when $Y^3$ is not a silicon atom, $-SiR^{20}R^{21}R^{22}$, wherein $R^{20}$, $R^{21}$ and $R^{22}$ are each independently selected from $(C_1\text{-}C_{18})$ alkyl, $(C_6\text{-}C_{18})$ aryl and $(C_7\text{-}C_{18})$ alkylaryl; t and u are each an integer selected from 0 and 1; and t+u=1 when $Y^3$=N, t=u=0 when $Y^3$=S, and t+u=2 when $Y^3$=Si;
   s is an integer selected from 0, 1 and 2;
   each F is independently selected from $(C_1\text{-}C_{18})$ alkyl, $(C_6\text{-}C_{18})$ aryl, $(C_7\text{-}C_{18})$ alkylaryl and $-Y^2(R^6)(R^7)_q(R^8)_r$, wherein
      $Y^2$ is selected from a nitrogen atom, a sulfur atom and a silicon atom; $R^6$, $R^7$ and $R^8$ are each independently selected from $(C_1\text{-}C_{18})$ alkyl, $di(C_1\text{-}C_6)$ alkyl amine (only when $Y^2$ is a silicon atom), $(C_6\text{-}C_{18})$ aryl, $(C_7\text{-}C_{18})$ alkylaryl and, when $Y^2$ is not a silicon atom, $-SiR^{17}R^{18}R^{19}$, wherein $R^{17}$, $R^{18}$ and $R^{19}$ are each independently selected from $(C_1\text{-}C_{18})$ alkyl, $(C_6\text{-}C_{18})$ aryl and $(C_7\text{-}C_{18})$ alkylaryl; q and r are each an integer selected from 0 and 1; and q+r=1 when $Y^2$=N, q=r=0 when $Y^2$=S, and q+r=2 when $Y^2$=Si;
   p is an integer selected from 0, 1, 2 and 3;
   K is selected from nitrogen, >C-H and >C-H and $>C\text{-}Y^3(R^9)(R^{10})_t(R^{11})_u$, wherein $Y^3$,$R^9$,$R^{10}$, $R^{11}$, t and u are independently as defined above.

2. The method according to claim 1, wherein the at least one type of polymerizable monomers is selected from 1,3-butadiene, isoprene and styrene.

3. The method according to claim 1, further comprising a step of reacting the polymer with one or more chain end modifying agents so as to provide a chain end-modified polymer.

4. The method according to claim 3, wherein the one or more chain end modifying agents are represented by the following Formulas 8, 9, 10, 11, 12, 13, 14, 15 and 16 and Lewis base adducts thereof:

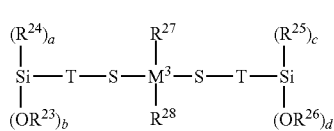

Formula 8 wherein $M^3$ is a silicon atom or a tin atom;
   T is at least divalent and is selected from $(C_6\text{-}C_{18})$ aryl, $(C_7\text{-}C_{18})$ alkylaryl and $(C_1\text{-}C_{18})$ alkyl, wherein each group is optionally substituted with one or more groups selected from $di(C_1\text{-}C_7$ hydrocarbyl)amino, $bis(tri(C_1\text{-}C_{12}$ alkyl)silyl)amino, $tris(C_1\text{-}C_7$ hydrocarbyl)silyl, $(C_7\text{-}C_{18})$ alkylaryl and $(C_6\text{-}C_{18})$ aryl;
   $R^{23}$ and $R^{26}$ are each independently selected from $(C_1\text{-}C_4)$ alkyl;
   $R^{24}$, $R^{25}$, $R^{27}$ and $R^{28}$ are each independently selected from $(C_1\text{-}C_{18})$ alkyl, $(C_6\text{-}C_{18})$ aryl and $(C_7\text{-}C_{18})$ alkylaryl;
   a and c are each independently selected from 0, 1 and 2; b and d are each independently selected from 1, 2 and 3; a+b=3; and c+d=3;

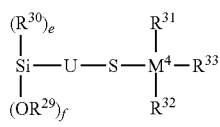

Formula 9 wherein $M^4$ is a silicon atom or a tin atom;
   U is at least divalent and is selected from $(C_6\text{-}C_{18})$ aryl, $(C_7\text{-}C_{18})$ alkylaryl and $(C_1\text{-}C_{18})$ alkyl, wherein each group is optionally substituted with one or more groups selected from di($C_1$-$C_7$ hydrocarbyl)amino, bis(tri($C_1$-$C_{12}$ alkyl)silyl)amino, tris($C_1$-$C_7$ hydrocarbyl)silyl, ($C_7$-$C_{18}$) alkylaryl and ($C_6$-$C_{18}$) aryl;

$R^{29}$ is independently selected from ($C_1$-$C_4$) alkyl, ($C_6$-$C_{18}$) aryl and ($C_7$-$C_{18}$) alkylaryl;

$R^{31}$, $R^{32}$ and $R^{33}$ are each independently selected from ($C_1$-$C_{18}$) alkyl, ($C_1$-$C_{18}$) alkoxy, ($C_6$-$C_{18}$) aryl and ($C_7$-$C_{18}$) alkylaryl;

$R^{30}$ is independently selected from ($C_1$-$C_{18}$) alkyl, ($C_1$-$C_{18}$) alkoxy, ($C_6$-$C_{18}$) aryl, ($C_7$-$C_{18}$) alkylaryl and $R^{34}$—($C_2H_4O$)$_g$—O—, wherein $R^{34}$ is selected from ($C_5$-$C_{23}$) alkyl, ($C_5$-$C_{23}$) alkoxy, ($C_6$-$C_{18}$) aryl and ($C_7$-$C_{25}$) alkylaryl and g is selected from 4, 5 and 6;

e is selected from 0, 1 and 2; f is selected from 1, 2 and 3; and e+f=3;

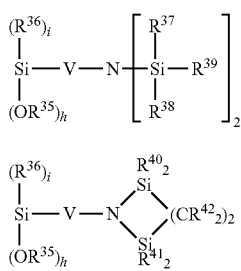

Formula 10

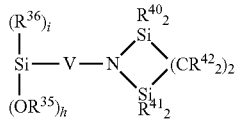

Formula 11 wherein V is at least divalent and is selected from ($C_6$-$C_{18}$) aryl, ($C_7$-$C_{18}$) alkylaryl and ($C_1$-$C_{18}$) alkyl, wherein each group is optionally substituted with one or more groups selected from di($C_1$-$C_7$ hydrocarbyl) amino, bis(tri($C_1$-$C_{12}$ alkyl)silyl)amino, tris($C_1$-$C_7$ hydrocarbyl)silyl, ($C_7$-$C_{18}$) alkylaryl and ($C_6$-$C_{18}$) aryl;

$R^{35}$ is independently selected from ($C_1$-$C_4$) alkyl, ($C_6$-$C_{18}$) aryl and ($C_7$-$C_{18}$) alkylaryl;

$R^{37}$, $R^{38}$, $R^{39}$, $R^{40}$, $R^{41}$ and $R^{42}$ are each independently selected from ($C_1$-$C_{18}$) alkyl, ($C_1$-$C_{18}$) alkoxy, ($C_6$-$C_{18}$) aryl and ($C_7$-$C_{18}$) alkylaryl;

$R^{36}$ is independently selected from ($C_1$-$C_{18}$) alkyl, ($C_1$-$C_{18}$) alkoxy, ($C_6$-$C_{18}$) aryl, ($C_7$-$C_{18}$) alkylaryl and $R^{43}$—($C_2H_4O$)$_j$—O—, wherein $R^{43}$ is selected from ($C_5$-$C_{23}$) alkyl, ($C_5$-$C_{23}$) alkoxy, ($C_6$-$C_{18}$) aryl and ($C_7$-$C_{25}$) alkylaryl; and j is selected from the 4, 5 and 6;

i is selected from 0, 1 and 2; h is selected from 1, 2 and 3; and i+h=3;

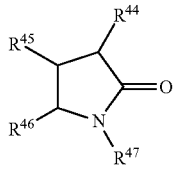

Formula 12

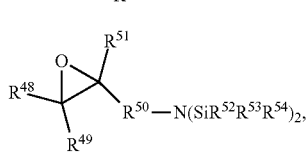

Formula 13 wherein $R^{44}$, $R^{45}$, $R^{46}$, $R^{47}$, $R^{48}$, $R^{49}$, $R^{51}$, $R^{52}$, $R^{53}$ and $R^{54}$ are each independently selected from hydrogen, ($C_1$-$C_{16}$) alkyl, ($C_6$-$C_{16}$) aryl and ($C_7$-$C_{16}$) alkylaryl; and $R^{50}$ is at least divalent and is selected from ($C_6$-$C_{18}$) aryl, ($C_7$-$C_{18}$) alkylaryl and ($C_1$-$C_{18}$) alkyl, wherein each group is optionally substituted with one or more groups selected from di($C_1$-$C_7$ hydrocarbyl)amino, bis(tri($C_1$-$C_{12}$ alkyl)silyl) amino, tris($C_1$-$C_7$ hydrocarbyl)silyl, ($C_7$-$C_{18}$) alkylaryl and ($C_6$-$C_{18}$) aryl;

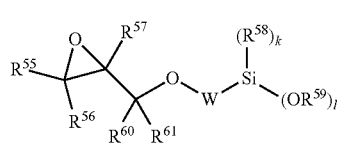

Formula 14

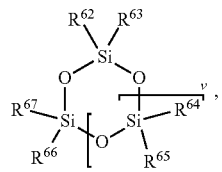

Formula 15

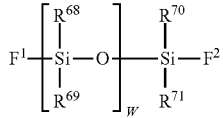

Formula 16 wherein $R^{55}$, $R^{56}$, $R^{57}$, $R^{58}$, $R^{60}$, $R^{61}$, $R^{62}$, $R^{63}$, $R^{64}$, $R^{65}$, $R^{66}$, $R^{67}$, $R^{68}$, $R^{69}$, $R^{70}$ and $R^{71}$ are each independently selected from hydrogen, ($C_1$-$C_{16}$) alkyl, ($C_6$-$C_{16}$) aryl and ($C_7$-$C_{16}$) alkylaryl;

$R^{59}$ is selected from ($C_1$-$C_4$) alkyl, ($C_6$-$C_{18}$) aryl and ($C_7$-$C_{18}$) alkylaryl;

W is at least divalent and is selected from ($C_6$-$C_{18}$) aryl, ($C_7$-$C_{18}$) alkylaryl and ($C_1$-$C_{18}$) alkyl, wherein each group is optionally substituted with one or more groups selected from di($C_1$-$C_7$ hydrocarbyl)amino, bis(tri($C_1$-$C_{12}$ alkyl)silyl) amino, tris($C_1$-$C_7$ hydrocarbyl)silyl, ($C_7$-$C_{18}$) alkylaryl and ($C_6$-$C_{18}$) aryl;

k is selected from 0, 1 and 2; l is selected from 1, 2 and 3; k+l=3; and v is selected from 1 to 20; and $F^1$ and $F^2$ are independently selected from hydrogen, hydroxy, chlorine, bromine, iodine, —$SiR^{52}R^{53}R^{54}$, wherein $R^{52}$, $R^{53}$, and $R^{54}$ are the same or different and are as defined for Formulas 12 and 13, vinyl, ($C_6$-$C_{16}$) aryl, ($C_7$-$C_{16}$) alkylaryl and ($C_1$-$C_{16}$) alkyl, wherein each hydrocarbyl group is optionally substituted with one or more groups selected from hydroxyl, di($C_1$-$C_7$ hydrocarbyl)amino, bis(tri($C_1$-$C_{12}$ alkyl)silyl)amino and an epoxy group.

5. A polymer obtainable by the method as defined in claim 1.

6. A polymer composition comprising the polymer or chain end-modified polymer as defined in claim 5 and one or more further components selected from (i) components which are added to or formed as a result of the polymerization process used for making said polymer and (ii) components which remain after solvent removal from the polymerization process.

7. The polymer composition according to claim 6, comprising one or more components selected from extender oils, stabilizers and further polymers.

8. The polymer composition as defined in claim 6, further comprising one or more fillers.

9. The polymer composition as defined in claim 8, wherein the one or more fillers are selected from carbon black, carbon nanotubes, graphite, graphene, silica, carbon-silica dual-phase filler, clays, calcium carbonate, magnesium carbonate, lignin, glass particle-based fillers, and starch-based fillers.

10. The polymer composition as defined in claim 6, further comprising one or more vulcanizing agents.

11. A vulcanized polymer composition which is obtained by vulcanizing the polymer composition as defined in claim 10.

12. A method of making a vulcanized polymer composition, comprising the step of vulcanizing the polymer composition as defined in claim 10.

13. An article comprising at least one component formed from the vulcanized polymer composition as defined in claim 11.

14. The method of making a polymer according to claim 1 wherein the polymerization initiator is represented by the following Formula 5:

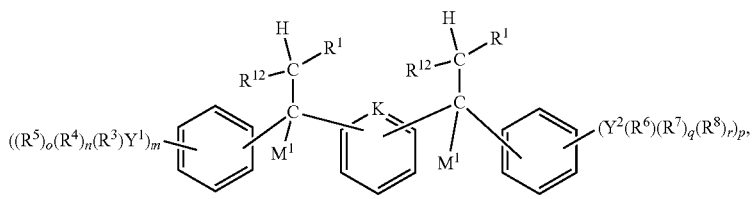

Formula 5 or a Lewis base adduct thereof,
wherein
$M^1$ is lithium;
each $R^1$ is independently selected from $(C_1\text{-}C_{18})$ alkyl;
$R^{12}$ is hydrogen;
$R^3$, $R^4$ and $R^5$ are each independently selected from $(C_1\text{-}C_{10})$ alkyl and, when $Y^1$ is not a silicon atom, $-SiR^{14}R^{15}R^{16}$, wherein $R^{14}$, $R^{15}$ and $R^{16}$ are each independently selected from $(C_1\text{-}C_{16})$ alkyl; and $R^6$, $R^7$ and $R^8$ are each independently selected from $(C_1\text{-}C_{10})$ alkyl and, when $Y^2$ is not a silicon atom, $-SiR^{17}R^{18}R^{19}$, wherein $R^{17}$, $R^{18}$ and $R^{19}$ are each independently selected from $(C_1\text{-}C_{16})$ alkyl.

16. The method of making a polymer according to claim 14,
wherein
each $R^1$ is independently selected from $(C_1\text{-}C_{10})$ alkyl;
$R^{12}$ is hydrogen;
$R^3$, $R^4$ and $R^5$ are each independently selected from $(C_1\text{-}C_{18})$ alkyl and, when $Y^1$ is not a silicon atom, $-SiR^{14}R^{15}R^{16}$, wherein $R^{14}$, $R^{15}$ and $R^{16}$ are each independently selected from $(C_1\text{-}C_{10})$ alkyl;
$R^6$, $R^7$ and $R^8$ are each independently selected from $(C_1\text{-}C_{18})$ alkyl and, when $Y^2$ is not a silicon atom, $-SiR^{17}R^{18}$ and $R^{19}$, wherein $R^{17}$, $R^{18}$ and $R^{19}$ are each independently selected from $(C_1\text{-}C_{10})$ alkyl;

m and p are each independently selected from an integer of 1 and 2.

17. The method of making a polymer according to claim 1, wherein the polymerization initiator is represented by the following Formula 6:

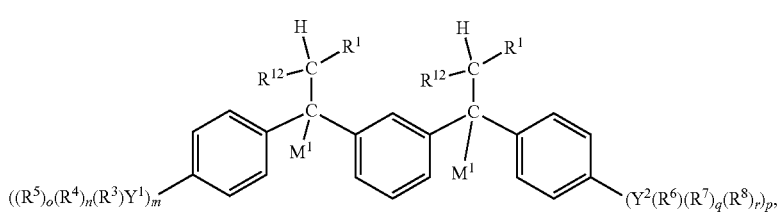

Formula 6 p is an an integer selected from 1, 2 and 3;
K is selected from nitrogen and >C—H; and
all other substituents or groups are as defined for Formula 1 in claim 1.

15. The method of making a polymer according to claim 14,
wherein
each $R^1$ is independently selected from $(C_1\text{-}C_7)$ alkyl;
$R^{12}$ is hydrogen;
$R^3$, $R^4$ and $R^5$ are each independently selected from $(C_1\text{-}C_{10})$ alkyl and, when $Y^1$ is not a silicon atom, $-SiR^{14}R^{15}R^{16}$, wherein $R^{14}$, $R^{15}$ and $R^{16}$ are each independently selected from $(C_1\text{-}C_{16})$ alkyl; and or a Lewis base adduct thereof,
wherein
$M^1$ is lithium;
each $R^1$ is independently selected from $(C_1\text{-}C_{10})$ alkyl;
$R^{12}$ is hydrogen;
$R^3$, $R^4$ and $R^5$ are each independently selected from $(C_1\text{-}C_{18})$ alkyl and, when $Y^1$ is not a silicon atom, $-SiR^{14}R^{15}R^{16}$, wherein $R^{14}$, $R^5$ and $R^{16}$ are each independently selected from $(C_1\text{-}C_{10})$ alkyl;
m and p are each independently an integer selected from 1 and 2;
$R^6$, $R^7$ and $R^8$ are each independently selected from $(C_1\text{-}C_{18})$ alkyl and, when $Y^2$ is not a silicon atom, $-SiR^{17}R^{18}R^{19}$, wherein $R^{17}$, $R^{18}$ and $R^{19}$ are each independently selected from $(C_1\text{-}C_{10})$ alkyl; and
all other substituents or groups are as defined for Formula 1 in claim 1.

18. The method of making a polymer according to claim 17,
wherein
each $R^1$ is independently selected from $(C_1\text{-}C_7)$ alkyl;
$R^{12}$ is hydrogen;
$R^3$, $R^4$ and $R^5$ are each independently selected from $(C_1\text{-}C_{10})$ alkyl and, when $Y^1$ is not a silicon atom, $-SiR^{14}R^{15}R^{16}$, wherein $R^{14}$, $R^{15}$ and $R^{16}$ are selected from $(C_1\text{-}C_{10})$ alkyl; and
$R^6$, $R^7$ and $R^8$ are each independently selected from $(C_1\text{-}C_{10})$ alkyl and, when $Y^2$ is not a silicon atom, $-SiR^{17}R^{18}R^{19}$, wherein $R^{17}$, $R^{18}$ and $R^{19}$ are each independently selected from $(C_1\text{-}C_{10})$ alkyl.

19. The method of making a polymer according to claim 1, wherein the polymerization initiator is represented by the following Formula 17, 18 or 19:

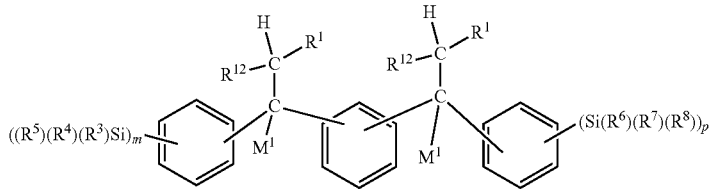

Formula 17

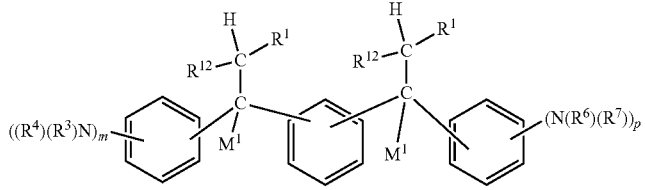

Formula 18

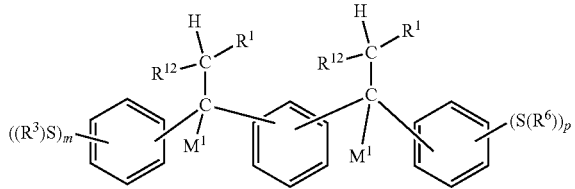

Formula 19 or Lewis base adducts thereof,
wherein
$M^1$ is lithium;
each $R^1$ is independently selected from $(C_1\text{-}C_{18})$ alkyl; and
all other substituents or groups are as defined for Formula 1 in claim 1.

20. The method of making a polymer according to claim 19, wherein
each $R^1$ is independently selected from $(C_1\text{-}C_{10})$ alkyl;
$R^{12}$ is hydrogen;
$R^3$, $R^4$ and $R^5$ are each independently selected from $(C_1\text{-}C_{18})$ alkyl and, when $Y^1$ is not a silicon atom, $-SiR^{14}R^{15}R^{16}$; wherein $R^{14}$, $R^{15}$ and $R^{16}$ are selected from $(C_1\text{-}C_{10})$ alkyl; and
$R^6$, $R^7$ and $R^8$ are each independently selected from $(C_1\text{-}C_{18})$ alkyl and, when $Y^2$ is not a silicon atom, $-SiR^{17}R^{18}R^{19}$, wherein $R^{17}$, $R^{18}$ and $R^{19}$ are each independently selected from $(C_1\text{-}C_{10})$ alkyl.

21. The method of making a polymer according to claim 19, wherein
each $R^1$ is each independently selected from $(C_1\text{-}C_7)$ alkyl;
$R^{12}$ is hydrogen;
$R^3$, $R^4$ and $R^5$ are each independently selected from $(C_1\text{-}C_{10})$ alkyl and, when $Y^1$ is not a silicon atom, $-SiR^{14}R^{15}R^{16}$; wherein $R^{14}$, $R^{15}$ and $R^{16}$ are selected from $(C_1\text{-}C_{10})$ alkyl; and
$R^6$, $R^7$ and $R^8$ are each independently selected from $(C_1\text{-}C_{18})$ alkyl and, when $Y^2$ is not a silicon atom, $-SiR^{17}R^{18}R^{19}$, wherein $R^{17}$, $R^{18}$ and $R^{19}$ are each independently selected from $(C_1\text{-}C_{10})$ alkyl.

* * * * *